United States Patent
Auer et al.

(10) Patent No.: US 12,377,050 B2
(45) Date of Patent: Aug. 5, 2025

(54) METHODS OF FORMING PARTICLES BY CONTINUOUS DROPLET FORMATION AND DEHYDRATION

(71) Applicant: Elektrofi, Inc., Boston, MA (US)

(72) Inventors: Jason G. Auer, Weymouth, MA (US); Paul Brown, Boston, MA (US); Tyler L. Carter, Newburyport, MA (US); Chase Spenser Coffman, Newton, MA (US); Paul F. Herbert, Framingham, MA (US); James W. Ivey, Reading, MA (US); Moin Khwaja, Boston, MA (US); Lisa Liu, Somerville, MA (US); Sadiqua Shadbar, Allston, MA (US); Shankul Vartak, Cambridge, MA (US)

(73) Assignee: Elektrofi, Inc., Boston, MA (US)

( * ) Notice: Subject to any disclaimer, the term of this patent is extended or adjusted under 35 U.S.C. 154(b) by 477 days.

(21) Appl. No.: 17/916,618

(22) PCT Filed: Apr. 16, 2021

(86) PCT No.: PCT/US2021/027755
§ 371 (c)(1),
(2) Date: Oct. 3, 2022

(87) PCT Pub. No.: WO2021/212019
PCT Pub. Date: Oct. 21, 2021

(65) Prior Publication Data
US 2023/0181473 A1 Jun. 15, 2023

Related U.S. Application Data

(60) Provisional application No. 63/011,820, filed on Apr. 17, 2020.

(51) Int. Cl.
| | | |
|---|---|---|
| *A61K 9/16* | (2006.01) | |
| *A61K 38/38* | (2006.01) | |
| *A61K 39/395* | (2006.01) | |
| *A61K 41/17* | (2020.01) | |
| *B01J 13/04* | (2006.01) | |

(52) U.S. Cl.
CPC .......... *A61K 9/1694* (2013.01); *A61K 9/1617* (2013.01); *A61K 9/1623* (2013.01); *A61K 9/1652* (2013.01); *A61K 38/385* (2013.01); *A61K 39/3955* (2013.01); *A61K 41/17* (2020.01); *B01J 13/04* (2013.01)

(58) Field of Classification Search
None
See application file for complete search history.

(56) References Cited

U.S. PATENT DOCUMENTS

| | | |
|---|---|---|
| 3,013,007 A | 12/1961 | Dale et al. |
| 3,882,036 A | 5/1975 | Krezanoski et al. |
| 4,172,896 A | 10/1979 | Uno et al. |
| 4,531,056 A | 7/1985 | Labowsky et al. |
| 5,358,970 A | 10/1994 | Ruff et al. |
| 5,427,798 A | 6/1995 | Ludwig et al. |
| 5,541,231 A | 7/1996 | Ruff et al. |
| 5,595,721 A | 1/1997 | Kaminski et al. |
| 5,612,055 A | 3/1997 | Bedford et al. |
| 5,677,180 A | 10/1997 | Robinson et al. |
| 5,731,000 A | 3/1998 | Ruff et al. |
| 5,736,137 A | 4/1998 | Anderson et al. |
| 5,739,169 A | 4/1998 | Ocain et al. |
| 5,763,493 A | 6/1998 | Ruff et al. |
| 5,801,005 A | 9/1998 | Cheever et al. |
| 5,824,311 A | 10/1998 | Greene et al. |
| 5,830,880 A | 11/1998 | Sedlacek et al. |
| 5,840,731 A | 11/1998 | Mayer et al. |
| 5,846,945 A | 12/1998 | McCormick |
| 6,095,134 A | 8/2000 | Sievers et al. |
| 6,110,973 A | 8/2000 | Young |
| 7,001,888 B2 | 2/2006 | Tidmarsh et al. |
| 8,013,022 B2 | 9/2011 | Deangelo et al. |
| 8,512,754 B2 | 8/2013 | Needham |
| 8,728,525 B2 | 5/2014 | Brown et al. |
| 8,779,094 B2 | 7/2014 | Johnston et al. |
| 8,939,388 B1 | 1/2015 | Beetz et al. |
| 9,259,701 B2 | 2/2016 | Palmer et al. |

(Continued)

FOREIGN PATENT DOCUMENTS

| | | |
|---|---|---|
| CN | 1750811 A | 3/2006 |
| CN | 103908432 A * | 7/2014 |

(Continued)

OTHER PUBLICATIONS

Allahham, D. et al., "Development and application of a microcapillary rheometer for in-vitro evaluation of parenteral injectability," Journal of Pharmacy and Pharmacology, vol. 56; 709-716 (2004).

Aniket et al., "Microglassification TM: A novel technique for protein dehydration," J Pharm Sci. 103(3): 810-820 (2014).

Banerjee et al., "Electrospray ionization mass spectrometry: a technique to access the information beyond the molecular weight of the analyte," Int J Anal Chem. Article 282574 (2012) (40 pages).

Bock et al., "Electrospraying of polymers with therapeutic molecules: state of the art," Prog Polym Sci. 37(11): 1510-1551 (2012) (67 pages).

Bogelein et al., "Cyclone selection influences protein damage during drying in a mini spray-dryer," Int J Pharm. 401 (1-2): 68-71 (2010).

(Continued)

*Primary Examiner* — Susan T Tran
(74) *Attorney, Agent, or Firm* — Hamilton, Brook, Smith & Reynolds, P.C

(57) ABSTRACT

The present disclosure relates to methods that enable the continuous formation of droplets and dehydration of droplets to provide pharmaceutically relevant particles that can be used for therapy. In particular, the methods disclosed herein allow the controlled continuous droplet formation and dehydration that produce circular particles having low internal void spaces comprising bioactive therapeutic biologies.

18 Claims, 10 Drawing Sheets

(56) References Cited

U.S. PATENT DOCUMENTS

| | | |
|---|---|---|
| 9,364,542 B2 | 6/2016 | Chang |
| 9,597,385 B2 | 3/2017 | Caplan |
| 9,643,996 B2 | 5/2017 | Petrel et al. |
| 11,077,059 B2 | 8/2021 | Coffman et al. |
| 11,459,376 B2 | 10/2022 | Brown et al. |
| 11,510,995 B2 | 11/2022 | Sanchez Martin et al. |
| 11,654,112 B2 | 5/2023 | Coffman et al. |
| 11,717,488 B2 | 8/2023 | Brown et al. |
| 11,795,429 B2 | 10/2023 | Bitterfield et al. |
| 12,115,262 B2 | 10/2024 | Coffman et al. |
| 12,178,913 B2 | 12/2024 | Coffman et al. |
| 2001/0031801 A1 | 10/2001 | Lyons et al. |
| 2002/0081732 A1 | 6/2002 | Bowlin et al. |
| 2003/0055010 A1 | 3/2003 | De Haan |
| 2004/0197469 A1 | 10/2004 | Lyons et al. |
| 2005/0013868 A1 | 1/2005 | Brynjelsen et al. |
| 2005/0019410 A1 | 1/2005 | Johnson |
| 2005/0186183 A1 | 8/2005 | DeAngelo et al. |
| 2006/0147400 A1 | 7/2006 | Piot |
| 2006/0292224 A1 | 12/2006 | Moore et al. |
| 2008/0026068 A1 | 1/2008 | Brown et al. |
| 2008/0095849 A1 | 4/2008 | Wu et al. |
| 2009/0035381 A1 | 2/2009 | Stankus et al. |
| 2009/0226530 A1 | 9/2009 | Lassner et al. |
| 2009/0274765 A1 | 11/2009 | Beduneau et al. |
| 2010/0047248 A1 | 2/2010 | Darvari et al. |
| 2010/0092526 A1 | 4/2010 | Baker, Jr. et al. |
| 2010/0092778 A1 | 4/2010 | Watanabe et al. |
| 2010/0305500 A1 | 12/2010 | Lambert et al. |
| 2010/0330169 A1 | 12/2010 | Bunick et al. |
| 2011/0223208 A1 | 9/2011 | Hill et al. |
| 2011/0280864 A1 | 11/2011 | Johnston et al. |
| 2012/0076800 A1 | 3/2012 | Dai et al. |
| 2012/0157591 A1 | 6/2012 | Rufner et al. |
| 2012/0244196 A1 | 9/2012 | Okubo et al. |
| 2013/0256931 A1 | 10/2013 | Palmer et al. |
| 2014/0052020 A1 | 2/2014 | Allen et al. |
| 2014/0262694 A1 | 9/2014 | Knigge |
| 2014/0263694 A1 | 9/2014 | Lin et al. |
| 2014/0271843 A1 | 9/2014 | Ma et al. |
| 2014/0288282 A1 | 9/2014 | Petrel et al. |
| 2014/0303356 A1 | 10/2014 | Gramer et al. |
| 2014/0308270 A1 | 10/2014 | Lobo et al. |
| 2014/0348852 A1 | 11/2014 | Vos et al. |
| 2014/0378370 A1 | 12/2014 | Johnston et al. |
| 2014/0378655 A1 | 12/2014 | Anderson |
| 2015/0079395 A1 | 3/2015 | Cruise et al. |
| 2015/0157576 A1 | 6/2015 | Shum et al. |
| 2016/0128944 A1 | 5/2016 | Chawrai et al. |
| 2016/0250329 A1 | 9/2016 | Bukrinski et al. |
| 2016/0271064 A1 | 9/2016 | Sell et al. |
| 2017/0210554 A1 | 7/2017 | Black et al. |
| 2018/0333493 A1 | 11/2018 | Shenoy |
| 2019/0374470 A1 | 12/2019 | Coffman et al. |
| 2020/0253875 A1 | 8/2020 | Coffman et al. |
| 2021/0220289 A1 | 7/2021 | Coffman et al. |
| 2021/0309724 A1 | 10/2021 | Brown et al. |
| 2021/0315827 A1 | 10/2021 | Brown et al. |
| 2021/0322317 A1 | 10/2021 | Coffman et al. |
| 2021/0403599 A1 | 12/2021 | Badovinac-Crnjevic et al. |
| 2022/0211627 A1 | 7/2022 | Arrighi et al. |
| 2022/0389084 A1 | 12/2022 | Brown et al. |
| 2023/0065628 A1 | 3/2023 | Auer et al. |
| 2023/0094393 A1 | 3/2023 | Charles et al. |
| 2023/0338299 A1 | 10/2023 | Paul et al. |
| 2023/0355530 A1 | 11/2023 | Coffman et al. |
| 2024/0255517 A1 | 8/2024 | Carter et al. |
| 2024/0270864 A1 | 8/2024 | Brown et al. |
| 2024/0293332 A1 | 9/2024 | Brown et al. |
| 2024/0415782 A1 | 12/2024 | Coffman et al. |
| 2025/0025425 A1 | 1/2025 | Brown et al. |
| 2025/0026811 A1 | 1/2025 | Brown et al. |
| 2025/0064744 A1 | 2/2025 | Coffman et al. |

FOREIGN PATENT DOCUMENTS

| | | |
|---|---|---|
| EP | 0 677 332 A2 | 10/1995 |
| EP | 2773330 B1 | 9/2020 |
| JP | 2003-513710 A | 4/2003 |
| JP | 2005-504090 A | 2/2005 |
| JP | 2005-504764 A | 2/2005 |
| JP | 2008-266128 A | 11/2008 |
| JP | 2010-524948 A | 5/2010 |
| JP | 2011-079747 A | 4/2011 |
| JP | 2011-241223 A | 12/2011 |
| JP | 2012-500799 A | 1/2012 |
| JP | 2012-508744 A | 4/2012 |
| JP | 2013-166100 A | 8/2013 |
| JP | 2014-058466 A | 4/2014 |
| JP | 2014-510077 A | 4/2014 |
| JP | 2014-129357 A | 7/2014 |
| JP | 2019-535832 A | 12/2019 |
| WO | 99/11196 A1 | 3/1999 |
| WO | 03/35301 A1 | 5/2003 |
| WO | 2006/087354 A2 | 8/2006 |
| WO | 2007/059782 A1 | 5/2007 |
| WO | 2008/062908 A1 | 5/2008 |
| WO | 2008/092084 A2 | 7/2008 |
| WO | 2010/044867 A1 | 4/2010 |
| WO | 2010/082543 A1 | 7/2010 |
| WO | 2011/131943 A2 | 10/2011 |
| WO | 2012/042274 A1 | 4/2012 |
| WO | 2014/057424 A2 | 4/2014 |
| WO | 2015/085898 A1 | 6/2015 |
| WO | 2015/138844 A1 | 9/2015 |
| WO | 2015/196091 A1 | 12/2015 |
| WO | 2016/014497 A1 | 1/2016 |
| WO | 2016/089309 A1 | 6/2016 |
| WO | 2017/106716 A1 | 6/2017 |
| WO | 2018/098376 A1 | 5/2018 |
| WO | 2018/234489 A1 | 12/2018 |
| WO | 2019/023392 A1 | 1/2019 |
| WO | 2019/226969 A1 | 11/2019 |
| WO | 2020/051307 A1 | 3/2020 |
| WO | 2020/160323 A2 | 8/2020 |
| WO | 2021/050953 A1 | 3/2021 |
| WO | 2021/158959 A2 | 8/2021 |
| WO | 2021/168271 A1 | 8/2021 |
| WO | 2021/212019 A1 | 10/2021 |
| WO | 2022/256840 A2 | 12/2022 |
| WO | 2023/212721 A1 | 11/2023 |
| WO | 2024/177927 A1 | 8/2024 |

OTHER PUBLICATIONS

Capelle, M.A.H et al., "High throughout screening of protein formulation stability: Practical considerations," European Journal of Pharmaceutics and Biopharmaceutics, vol. 65; 131-148 (2007).

Clackson, T. et al., "Making antibody fragments using phage display libraries," Nature vol. 352; 624-628 (1991).

Cloupeau et al., "Electrostatic spraying of liquids: Main functioning modes," J Electrostat. 25(2): 165-184 (1990).

Cloupeau et al., "Electrohydrodynamic spraying functioning modes: a critical review," J Aerosol Sci. 25(6): 1021-1036 (1994).

Dias et al., "Tolerability of High-vol. Subcutaneous Injections of a Viscous Placebo Buffer: A Randomized, Crossover Study in Healthy Subjects," AAPS PharmSciTech. 16(5): 1101-1107 (2015).

Elektrofi, Inc., Redefining the Delivery of Biologics, 11 pages, retrieved from Internet URL: https://www.elektrofi.com/welcome#technology on Nov. 15, 2021.

Fenn et al., "Electrospray ionization for mass spectrometry of large biomolecules," Science. 246(4926):64-71 (Oct. 6, 1989).

Fernandez de la Mora et al., "The current emitted by highly conducting taylor cones," J Fluid Mech. 260: 155-184 (1994).

Fernandez de la Mora et al., "The fluid dynamics of Taylor cones," Annu Rev Fluid Mech. 39: 217-43 (2007) (29 pages).

Forgacs, E. et al., "Direct (Normal)-Phase High-Performance Liquid Chromatography," Chapter II.B. in Molecular Basis of Chromatographic Separation, CRC Press, Baco Raton, FL; 120-131 (1997).

(56) References Cited

OTHER PUBLICATIONS

Frost, G.I., "Recombinant human hyaluronidase (rHuPH20): an enabling platform for subcutaneous drug and fluid administration," Expert Opinion Drug Deliv., vol. 4; No. 4; 427-440 (2007).
Galam et al., "High-throughput assay for the identification of Hsp90 inhibitors based on Hsp90-dependent refolding of firefly luciferase," available in PMC Mar. 1, 2008, published in final edited form as: Bioorg Med Chem. 15(5): 1939-1946 (2007) (16 pages).
Ganan-Calvo et al., "Current and droplet size in the electrospraying of liquids. Scaling laws," J Aerosol Sci. 28(2): 249-275 (1997).
Gapinski et al., "Structure and dimensions of core-shell nanoparticles comparable to the confocal volume studied by means of fluorescence correlation spectroscopy," Langmuir. 32(10): 2482-2491 (Feb. 2016).
Gikanga et al., "Manufacturing of High-Concentration Monoclonal Antibody Formulations via Spray Drying—the Road to Manufacturing Scale," PDA J Pharm Sci Technol. 69(1): 59-73 (2015) (16 pages).
Giugliano et al., "Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study," available in PMC Mar. 3, 2015, published in final edited form as: Lancet. 380(9858): 2007-17 (2012) (20 pages).
Gulfam, M. et al., "Anticancer Drug-Loaded Gliadin Nanoparticles Induce Apoptosis in Breast Cancer Cells," American Chemical Society, Langmuir, vol. 28; 8216-8223 (2012).
Haggag et al., "Evaluation of nano spray drying as a method for drying and formulation of therapeutic peptides and proteins," Front Pharmacol. 6:140 (2015) (5 pages).
Hickey, J.W. et al., "Biologically Inspired Design of Nanoparticle Artificial Antigen-Presenting Cells for Immunomodulation," Nano Letters, vol. 17; 7045-7054 )2017).
Hui et al., "Progress in preparation of peptide protein drug microspheres," The medicine herald, Issue 10, 2007, pp. 1-32. (Concise explanation met by attached English Translation of CN Search report).
Imamura, K. et al., "Evaluation of Hydration States of Protein in Freeze-Dried Amorphous Sugar Matrix," J. Pharm. Sci., vol. 90; 1955-1963 (2001).
Imamura, K., "Sugar-Protein Interaction and Stabilization of Protein in Amorphous Sugar Matrix," Cryobiology and Cryotechnology, vol. 51; No. 1; 31-35 (2005). English Abstract included.
Janssen Biotech Inc., "Highlights of prescribing information," <http://www.janssenlabels.com/package-inserl/product-monograph/prescribinginformation/DARZALEX-pi.pdl>, dated Jul. 2019, retrieved on Aug. 22, 2019 (13 pages).
Jones, A.U.S., "Analysis of Polypeptides and Proteins," Advanced Drug Delivery Reviews, vol. 10; 29-90 (1993).
Jun, L., "Guizho Science and Technology Press", Agricultural building materials, Aug. 31, 1999, 4 pages (Concise explanation met by the attached English Translation of CN Appl 202080064558 office action).
Kaltashov et al., "Estimates of Protein Surface Areas in Solution by Electrospray Ionization Mass Spectrometry," available in PMC Jan. 27, 2009, published in final edited form as: Anal Chem. 77(16): 5370-5379 (2005).
Kim et al., "Controlled production of emulsion drops using an electric field in a flow-focusing microfluidic device," Appl Phys Lett. 91: 133106 (2007) (3 Pages).
Ku et al., "Electrospray characteristics of highly viscous liquids," J Aerosol Sci. 33(10): 1361-1378 (2002).
Lal et al., "Clean western blot signals from immunoprecipitated samples," available in PMC Jan. 25, 2006, published in final edited form as: Mol Cell Probes. 19(6): 385-388 (2005) (5 pages).
Lavorini et al., "New inhaler devices—the good, the bad and the ugly," Respiration. 88(1): 3-15 (2014).
Lee et al., "Solid-state stabilization of a Chymotrypsin and catalase with carbohydrates," Ind Eng Chem Res. 45(14): 5134-5147 (2006).

Li et al., "Effects of pulsed electric fields and heat treatment on stability and secondary structure of bovine immunoglobulin G," J Agric Food Chem. 53(3): 663-670 (2005).
Longman et al., "Identifying differences in solution Conformations of two chimeric IgG3 antibodies through triple detection SEC," LCGC North America. 18(21): (2005) (10 pages).
Lopez-Herrera et al., "Coaxial jets generated from eleclified Taylor cones. Scaling laws," J Aerosol Sci. 34(5): 535-552 (2003).
Loscertales et al., "Micro/nano encapsulation via electrified coaxial liquid jets," Science. 295(5560): 1695-8 (2002).
Makadia et al., "Poly lactic-co-glycolic acid (PLGA) as biodegradable controlled drug delivery carrier," Polymers (Basel). 3(3): 1377-1397 (2011).
Mardles. E. W. J., "Viscosity of Suspensions and the Einstein Equation," Nature. 145: 970 (Jun. 22, 1940).
Miller et al., "Antibody nanoparticle dispersions formed with mixtures of crowding molecules retain activity and in vivo bioavailability," available in PMC Oct. 1, 2013, published in final edited form as: J Pharm Sci. 101(10): 3763-3778 (2012) (25 pages).
Miller et al., "Low viscosity highly concentrated injectable nonaqueous suspensions of lysozyme microparticles," available in PMC Feb. 17, 2011, published in final edited form as: Langmuir. 26(2): 1067-1074 (2010) (22 pages).
Moghadam et al., "Electro-spray of high viscous liquids for producing mono-sized spherical alginate beads," Particuology. 6(4): 271-275 (2008).
Morales-Cruz et al., "Two-step nanoprecipitation for the production of protein-loaded PLGA nanospheres," Results Pharma Sci. 2: 79-85 (2012).
Mueller et al., "The rheology of suspensions of solid particles," Proc R Soc A. 466: 1201-1228 (2010).
Naqvi et al., "Living cell factories—electrosprayed microcapsules and microcarriers for minimally invasive delivery," Adv Maler. 28(27): 5662-71 (2016)(10 pages).
Nema et al., Pharmaceutical Dosage Forms: Parenteral Medications, Third Edition, vol. 3: Requlations, Validation and the Future. Informa Healthcare, vii-304 (2010) (328 pages).
Nguyen et al., "Pharmaceutical applications of electrospraying," J Pharm Sci. 105(9): 2601-2620 (2016).
Papir, Y.S. and Krieger, I.M., "Rheological Studies on Dispersions of Uniform Colloidal Spheres," Journal of Colloid and Interface Science, vol. 34; No. 1; 126-130 (1970).
Park et al., "One step immobilization of protein encapsulated core/shell particles onto nanofibers," Macromol Maler Eng. 295(6): 544-550 (2010).
Patel et al., "Poloxamers: a pharmaceutical excipients with therapeutic behaviors," International Journal of PharmTech Research. 1(2):299-303 (2009).
Pearlman, R. and Nguyen, T.H., "Analysis of Protein Drugs," Peptide and Protein Drug Delivery, Vincent Lee Ed., Marcel Dekker, Inc., New York, NY, pp. 247-301 (1991).
Persic, L. et al., "An integrated vector system for the eukaryotic expression of antibodies or their fragments after selection from phage display libraries," Gene; 9-18 (1997).
Pivnik, A.V., "Use of rituximab for treatment of HIV-infected patients with hematological disorders," Genotekhnologiya Medical Center, Moscow, 7 pages; English Abstract Only (2013).
Plückthun, A., "Antibodies from *Escherichia coli*," In: The pharmacology of monoclonal antibodies, M. Rosenberg and G. P. Moore, Eds. (Springer Verlag, Berlin, 1994), vol. 113, pp. 269-315.
Press, O.W. et al., "Monoclonal Antibody 1F5 (Anti-CD20) Serotherapy of Human B Cell Lymphoma," Blood, vol. 69; No. 2; 584-591 (1987).
Reichardt, C., "Solvatochromic Dyes as Solvent Polarity Indicators," Chem. Rev., vol. 94; 2319-2358 (1994).
Richardson, H. et al., "Influence of the glass transition on solvent loss from spin-cast glassy polymer thin films," Eur. Phys. J. E, vol. 12; 021; S87-S91 (2003).
Saglam et al., "Preparation of high protein micro-particles using two-step emulsification," Food Hydrocolloids. 25 (5):1139-48 (2011).
Sblattero, D. and Bradbury, A., "Exploiting recombination in single bacteria to make large phage antibody libraries," Nature Biotechnology, vol. 18; 75-80 (2000).

(56) References Cited

OTHER PUBLICATIONS

Serra-Peinado, C., et al., "Expression of CD20 after viral reactivation renders HIV-reservoir cells susceptible to Rituximab," Nature Communications, vol. 10; 15 pages (2019).
Shire et al., "Challenges in the development of high protein concentration formulations," J Pharm Sci. 93(6): 1390-402 (2004).
Sridhar, R. and Ramakrishna, S., "Electrosprayed nanoparticles for drug delivery and pharmaceutical applications," Biomatter, vol. 3; No. 3; e24281-1; 14 pages (2013).
Takats et al., "Electrosonic spray ionization. A gentle technique for generating folded proteins and protein complexes in the gas phase and for studying ion-molecule reactions at atmospheric pressure," Anal Chem. 76(14): 4050-58 (2004).
Torchilin, "Multifunctional nanocarriers," Adv Drug Deliv Rev. 58(14): 1532-55 (2006).
U.S. Department of Health and Human Services, "Q3C—Tables and List: Guidance for Industry," Aug. 2018 (10 pages).
Vanhoff, Sebastian, Thesis: "The Influence of Atomization Conditions on Protein Secondary and Tertiary Structure During Microparticle Formation by Spray-Freezing-Drying ," Doktorgrades Dr. rer. nat, Der Naturwissenschaftlichen Fakultat, der Friedrich-Alexander Universitat Erlangen-Nurnberg, 2010 (195 pages).
Vehring, "Pharmaceutical particle engineering via spray drying," Pharm Res. 25(5): 999-1022 (2008).
Vehring, R. et al., "Particle formation in spray drying," Aerosol Science, vol. 38; 728-746 (2007).
Wang et al., "FDA's regulatory science program for generic PLA/PLGA-based drug products," Am Pharm Rev. <https://www.americanpharmaceuticalreview.com/Featured-Articles/188841-FDAs-Regulatory-Science-Program-for-Generic-PLA-PLGA-Based-Drug-Products/>, dated Jun. 15, 2016, retrieved on Aug. 22, 2019 (5 pages).
Wanning et al., "Pharmaceutical spray freeze drying," Int J Pharm. 488(1-2): 136-53 (2015).
Xie et al., "Encapsulation of protein drugs in biodegradable microparticles by co-axial electrospray," J Colloid Interface Sci. 317(2): 469-76 (2008).
Yuan et al., "Coaxial electrospray of curcumin-loaded microparticles for sustained drug release," PLoS One. 10(7): e0132609 (2015) (15 pages).
Yuan et al., "One-step fabrication of triple-layered microcapsules by a tri-axial flow focusing device for microencapsulation of soluble drugs and imaging agents," Proc SPIE vol. 9711, Imaging, Manipulation, and Analysis of Biomolecules, Cells, and Tissues IX (2016) (12 pages).
Zhang et al., "Coaxial electrospray of microparticles and nanoparticles for biomedical applications," Expert Rev Med Devices. 9(6): 595-612 (2012).
Zhang et al., "Coaxial electrospray of ranibizumab-loaded microparticles for sustained release of anti-VEGF therapies," PloS One. 10(8):e0135608 (2015) (16 pages).
Zhang, J. et al., "Fundamentals and applications of inertial microfluidics: a review," Lab Chip, vol. 16; 10-34 (2016).
Zhiqi, L., et al., "Functional Emulsifiers and Emulsions", China Light Industry Press, Apr. 30, 2000, 2 pages. (Concise explanation met by English Translation of Search report attached).
Ziabicki, A. and Jarecki, L., "Crystal Nucleation in an Electric Field," Macromol. Symp., vol. 104; 65-87 (1996).
Notification of Transmittal of the International Search Report and Written Opinion for PCT/US2021/027755, mailed Aug. 13, 2021.

\* cited by examiner

METHODS OF FORMING PARTICLES BY CONTINUOUS DROPLET FORMATION AND DEHYDRATION

RELATED APPLICATION(S)

This application is the U.S. National Stage of International Application No. PCT/US2021/027755, filed Apr. 16, 2021, published in English, which claims the benefit of U.S. Provisional Application No. 63/011,820, filed on Apr. 17, 2020. The entire teachings of the above applications are incorporated herein by reference.

GOVERNMENT SUPPORT

This invention was made with government support under Grant No. 1831212 awarded by the National Science Foundation. The government has certain rights in the invention.

TECHNICAL FIELD

The present disclosure relates to methods that enable the formation of pharmaceutically relevant particles that can be used for therapy. In particular, the methods disclosed herein allow large-scale continuous droplet formation and dehydration that produce circular particles having low internal void spaces comprising therapeutic biologics.

BACKGROUND

Materials science and the application of nanotechnology calls for more efficient, reproducible and innovative technologies to synthesize novel functional particles. Recent advances in synthesis and the controlled assembly of bioactive particles have enabled their applications for use in therapy. Current efforts have been directed to developing new synthetic approaches for non-circular microparticles that often exhibit physical properties unobtainable by simply tuning the size and form of the particles. However, the application of these techniques to circular particles have been limited due to the lack of sufficient control over size uniformity, shape selectivity, surface functionality and density of the particles which are often difficult to obtain. Therefore, a highly robust and controlled method for particle preparation is needed.

SUMMARY

Provided herein are methods allowing the continuous droplet formation and dehydration of aqueous liquid droplets comprising a therapeutic biologic that produce circular particles having low internal void spaces.

In one aspect, the disclosure provides a method of forming particles, the method comprising:
a) providing an aqueous first liquid comprising a therapeutic biologic;
b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic;
c) dehydrating the aqueous liquid droplets in the mixture; and
d) removing the aqueous first liquid and organic second liquid from the mixture,
thereby forming particles comprising the therapeutic biologic, wherein the particles comprise less than about 10% internal void spaces and the circularity of the particles is from about 0.80 to about 1.00 after removing the aqueous first liquid and organic second liquid from the mixture.

The present disclosure also provides herein, a method of controlling the morphology of particles.

In another aspect, the disclosure provides a method of controlling the morphology of particles, the method comprising:
a) providing an aqueous first liquid comprising a therapeutic biologic;
b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic, wherein the Peclet number of the mixture determines the morphology of the particles;
c) dehydrating the aqueous liquid droplets in the mixture; and
d) removing the aqueous first liquid and organic second liquid from the mixture,
thereby forming particles comprising the therapeutic biologic, wherein the particles comprise less than about 10% internal void spaces and the circularity of the particles is from about 0.80 to about 1.00 after removing the aqueous first liquid and organic second liquid from the mixture.

The present methods may be useful for the formation of pharmaceutically relevant particles that can be used for therapy. In preferred embodiments, the methods disclosed herein allows the continuous formation of droplets comprising a therapeutic biologic and the dehydration of the droplets that produce circular particles having low internal void spaces.

BRIEF DESCRIPTION OF THE DRAWINGS

The foregoing will be apparent from the following more particular description of example embodiments, as illustrated in the accompanying drawings in which like reference characters, refer to the same parts throughout the different views. The drawings are not necessarily to scale, emphasis instead being placed upon illustrating embodiments.

DETAILED DESCRIPTION

Figure 1:
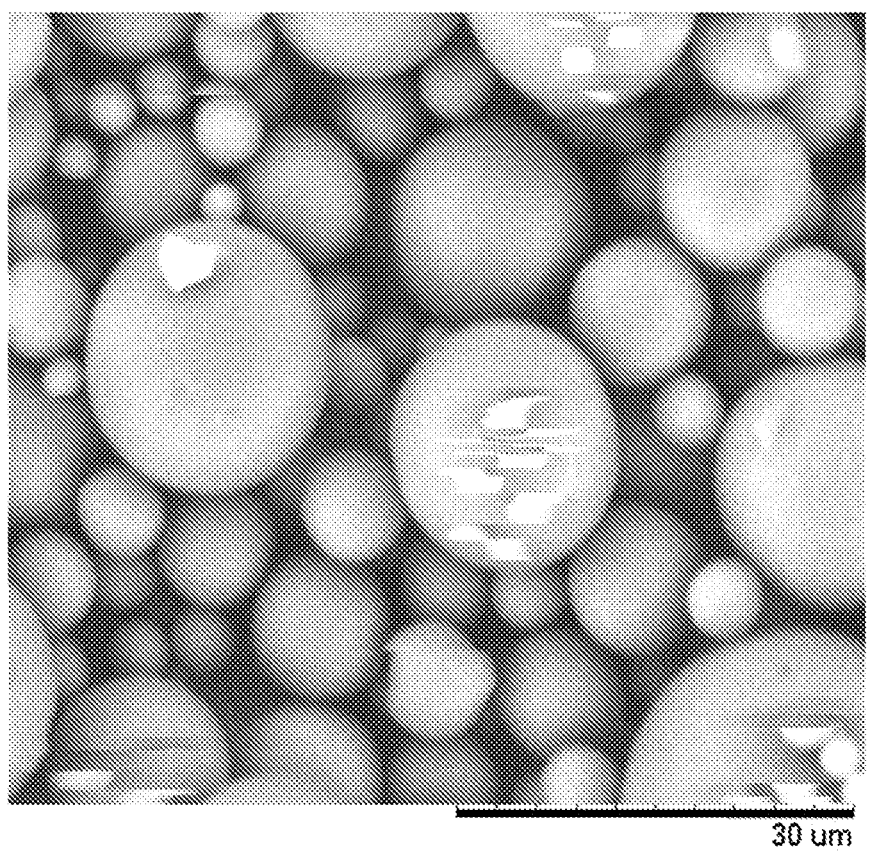
FIG. 1 shows an image of particles containing human IgG and excipients with controlled particle size formed through static mixing. Scale bar is 30 μm.
Figure 2:
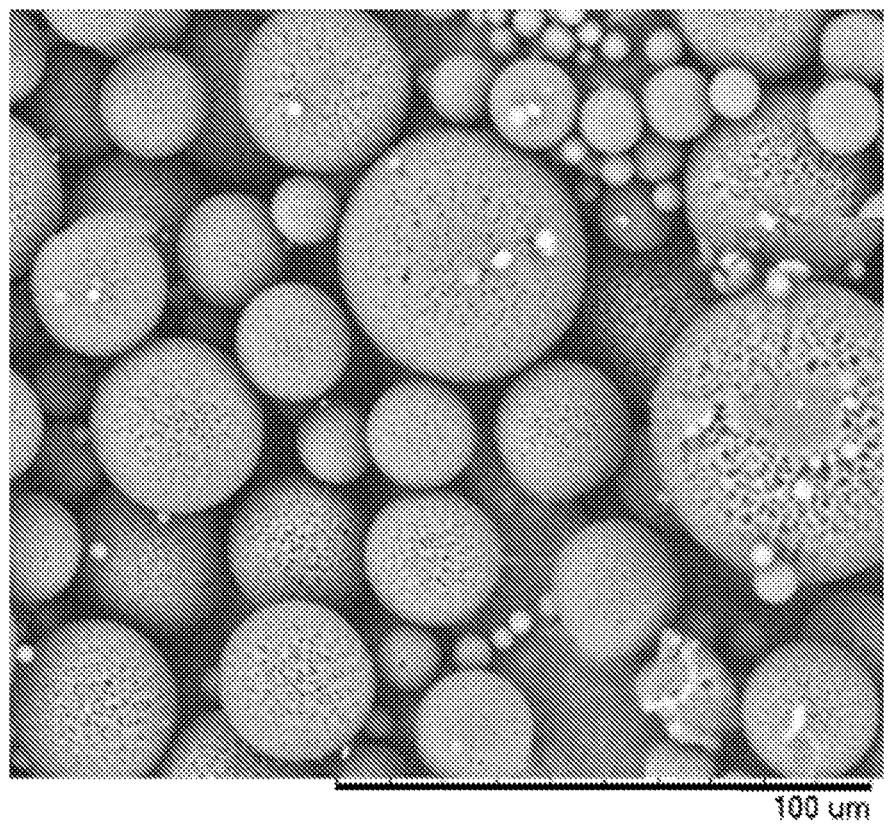
FIG. 2 shows an image of particles comprising BSA and excipients that were obtained by static mixing using methods of the disclosure. Scale bar is 100 μm.

Particles have been produced using various techniques. For example, the generation of particles can be accomplished by producing a liquid droplet comprising an active agent dissolved in an aqueous liquid. The aqueous liquid can then be extracted from the liquid droplets by depositing the droplets into a second liquid in which the aqueous liquid, but not the active agent is soluble leaving behind a solid particle. Isolation of the particles occurs following removal of the liquids. However, the application of these techniques to form functional circular particles have been limited due to the lack of sufficient control over size uniformity, shape selectivity, surface functionality and density of the particles which are often difficult to obtain. The present disclosure seeks to mitigate the control issues that are associated with forming functional particles by providing a robust and controlled method for particle preparation.

The present disclosure generally relates to methods of forming particles, the method comprising: a) providing an aqueous first liquid comprising a therapeutic biologic; b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic; c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture.

In certain aspects, the disclosure generally relates to a method of controlling the morphology of particles, the method comprising: a) providing an aqueous first liquid comprising a therapeutic biologic; b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic, wherein the Peclet number of the mixture determines the morphology of the particles; c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture.

As described herein, the disclosure provides methods for the preparation of particles comprising a therapeutic biologic, e.g., an antibody, bovine serum albumin (BSA), or human serum albumin (HSA). In preferred embodiments, the therapeutic biologic is an antibody, antibody fragment, bovine serum albumin (BSA), or human serum albumin (HSA). The generation of particles can be accomplished by providing aqueous liquid droplets comprising a therapeutic biologic and an aqueous first liquid. The aqueous liquid droplets can then be contacted with an organic second liquid by a continuous process. The aqueous first liquid can then be removed from the aqueous liquid droplets by contacting the aqueous liquid droplets comprising the therapeutic biologic with an organic second liquid by a continuous process in which the aqueous first liquid, but not the therapeutic biologic, is soluble leaving behind a solid particle. Isolation of the particles occurs following removal of the aqueous first liquid and organic second liquid from the mixture. The process of continuously forming and dehydrating the aqueous liquid droplets as described herein, can significantly alter the structure and morphology of the particles and can enhance the stability of the therapeutic biologic. These particles may be used to generate stabilized pharmaceutical compositions, pharmaceutical suspension formulations, pharmaceutical powder formulations (e.g., inhalable powders, injectable powders), creams or other topical pastes, nutraceuticals, or cosmetics. The term "pharmaceutical composition" as used herein, denotes a composition in which a therapeutic biologic retains, or partially retains, its intended biological activity or functional form, and in which only pharmaceutically acceptable components are included.

It will be readily understood that the aspects and embodiments, as generally described herein, are exemplary. The following more detailed description of various aspects and embodiments are not intended to limit the scope of the present disclosure, but is merely representative of various aspects and embodiments. Moreover, the methods disclosed herein may be changed by those skilled in the art without departing from the scope of the present disclosure. Unless defined otherwise, all technical and scientific terms used herein have the same meaning as is commonly understood by one of skill in the art to which this disclosure belongs. All publications and patents referred to herein are incorporated by reference.

Definitions

For purposes of the present disclosure, the following definitions will be used unless expressly stated otherwise:

The terms "a", "an", "the" and similar referents used in the context of describing the present disclosure are to be construed to cover both the singular and the plural, unless otherwise indicated herein or clearly contradicted by context. All methods described herein, can be performed in any suitable order unless otherwise indicated herein or otherwise clearly contradicted by context. The use of any and all examples, or exemplary language (e.g., "such as") provided herein, is intended merely to better illuminate the present disclosure and does not pose a limitation on the scope of the disclosure otherwise claimed. No language in the present specification should be construed as indicating any unclaimed element is essential to the practice of the disclosure.

The term "about" in relation to a given numerical value, such as for temperature and period of time, is meant to include numerical values within 10% of the specified value.

As used herein, an "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, iso-butyl, sec-butyl, tert-butyl, n-pentyl, tert-pentyl, neo-pentyl, iso-pentyl, sec-pentyl, 3-pentyl, sec-iso-pentyl, active-pentyl, hexyl, heptyl, octyl, ethylhexyl, and the like. A $C_{1-8}$ straight chained or branched alkyl group is also referred to as a "lower alkyl" group. An alkyl group with two open valences is sometimes referred to as an alkylene group, such as methylene, ethylene, propylene and the like. Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, an alkyl, a halogen, a hydroxyl, a carbonyl (such as a carboxyl, and alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN and the like. In other embodiments, the term "alkyl" can mean "cycloalkyl" which refers to a non-aromatic carbocyclic ring having 3 to 10 carbon ring atoms, which are carbon atoms bound together to form the ring. The ring may be saturated or have one or more carbon-carbon double bonds. Examples of cycloalkyl include, but not limited to cyclopropyl, cyclobutyl, cyclopentyl, cyclopentenyl, cyclohexyl, cyclohexenyl, and cycloheptyl, as well as bridged and caged saturated ring groups such as norbornyl and adamantyl. As described herein, organic solvents include, but are not limited to aliphatic hydrocarbon solvents, aromatic hydrocarbon solvents, alcohols or alkylalcohols, alkylethers, sulfoxides, alkylketones, alkylacetates, trialkylamines, alkylformates, trialkylamines, or a combination thereof. Aliphatic hydrocarbon solvents can be pentane, hexane, heptane, octane, cyclohexane, and the like or a combination thereof. Aromatic hydrocarbon solvents can be benzene, toluene, and the like or a combination thereof. Alcohols or alkylalcohols include, for example, methanol, ethanol, propanol, butanol, pentanol, hexanol, heptanol, octanol, decanol, amylalcohol, or a combination thereof. Alkylethers include methyl, ethyl, propyl, butyl, and the like, e.g., diethylether, diisopropylether or a combination thereof. Sulfoxides include dimethyl sulfoxide (DMSO), decylmethyl sulfoxide, tetradecylmethyl sulfoxide, and the like or a combination thereof. The term "alkylketone" refers to a ketone substituted with an alkyl group, e.g., acetone, ethylmethylketone, and the like or a combination thereof. The term "alkylacetate" refers to an acetate substituted with an alkyl group, e.g., ethylacetate, propylacetate (n-propylacetate, iso-propylacetate), butylacetate (n-butylacetate, iso-butylacetate, sec-butylacetate, tert-butylacetate), amylacetate (n-pentylacetate, tert-pentylacetate, neo-pentylacetate, iso-pentylacetate, sec-pentylacetate, 3-pentylacetate, sec-iso-pentylacetate, active-pentylacetate), 2-ethylhexylacetate, and the like or a combination thereof. The term "alkylformate" refers to a formate substituted with an alkyl group, e.g., methylformate, ethylformate, propylformate, butylformate, and the like or a combination thereof. The term "trialkylamine" refers to an amino group substituted with three alkyl groups, e.g., triethylamine.

As used herein, an "amino acid" or "residue" refers to any naturally or non-naturally occurring amino acid, any amino acid derivative or any amino acid mimic known in the art. Included are the L- as well as the D-forms of the respective amino acids, although the L-forms are usually preferred. In some embodiments, the term relates to any one of the 20 naturally occurring amino acids: glycine (Gly), alanine (Ala), valine (Val), leucine (Leu), isoleucine (Ile), proline (Pro), cysteine (Cys), methionine (Met), serine (Ser), threonine (Thr), glutamine (Gln), asparagine (Asn), glutamic acid (Glu), aspartic acid (Asp), lysine (Lys), histidine (His), arginine (Arg), phenylalanine (Phe), tryptophan (Trp), and tyrosine (Tyr) in their L-form. In certain embodiments, the amino acid side-chain may be a side-chain of Gly, Ala, Val, Leu, Ile, Met, Cys, Ser, Thr, Trp, Phe, Lys, Arg, His, Tyr, Asn, Gln, Asp, Glu, or Pro.

As used herein, except where the context requires otherwise, the term "comprise" and variations of the term, such as "comprising", "comprises" and "comprised", are not intended to exclude further additives, components, integers or steps. The terms "including" and "comprising" may be used interchangeably. As used herein, the phrases "selected from the group consisting of", "chosen from", and the like, include mixtures of the specified materials. Where a numerical limit or range is stated herein, the endpoints are included. Also, all values and subranges within a numerical limit or range are specifically included as if explicitly written herein. References to an element in the singular is not intended to mean "one and only one" unless specifically stated, but rather "one or more". Unless specifically stated otherwise, terms such as "some" refer to one or more, and singular terms such as "a", "an" and "the" refer to one or more.

As used herein, "continuous process" means a process in which droplet formation and dehydration proceed in succession and without interruption for a period of time (e.g., about 1 to about 60 seconds, about 1 minute to about 60 minutes, about 1 hour to about 24 hours, about 1 day to about 7 days, and about 1 week to about 4 weeks). The particles produced by the continuous process are then passed on for further processing, such as, for example, solid liquid separation and/or secondary dehydration. As used herein, the phrase "semi-continuous process" means a process in which droplet formation and dehydration proceed with interruption (e.g., one or more interruptions) of the process, for example, the process is stopped for a period of time to stop droplet formation and/or to complete the dehydration process. For example, in any of the exemplary continuous or semi-continuous process methods described herein, an aqueous first liquid comprising a therapeutic biologic, and an organic second liquid are continuously or semi-continuously mixed to facilitate droplet formation and dehydration in part of the system, resulting in the formation of particles comprising at least one therapeutic biologic. In some embodiments, the disclosure provides a method of contacting the aqueous first liquid comprising the therapeutic biologic with an organic second liquid by a continuous process, thereby forming a mixture comprising aqueous liquid droplets, wherein the aqueous liquid droplets comprising the therapeutic biologic are dehydrated to form particles comprising at least one therapeutic biologic.

Oligopeptides described herein, are typically comprised of about two to about forty amino acid residues. Oligopeptides include dipeptides (two amino acids), tripeptides (three amino acids), tetrapeptides (four amino acids), pentapeptides (five amino acids), hexapeptides (six amino acids), heptapeptides (seven amino acids), octapeptides (eight amino acids), nonapeptides (nine amino acids), decapeptides (ten amino acids), undecapeptides (eleven amino acids), dodecapeptides (twelve amino acids), icosapeptides (twenty amino acids), tricontapeptides (thirty amino acids), tetracontapeptides (forty amino acids), and the like. Oligopeptides may also be classified according to molecular structure: aeruginosins, cyanopeptolins, microcystins, microviridins, microginins, anabaenopeptins and cyclamides, and the like. Homo-oligopeptides are oligopeptides comprising the same amino acid. In preferred embodiments, homo-oligopeptides comprise 10 amino acid poly-valine, poly-alanine, and polyglycine hexamers.

The meaning of the term "peptides" are defined as small proteins of two or more amino acids linked by the carboxyl group of one to the amino group of another. Accordingly, at its basic level, peptide synthesis of whatever type comprises the repeated steps of adding amino acid or peptide molecules to one another or to an existing peptide chain. The term "peptide" generally has from about 2 to about 100 amino acids, whereas a polypeptide or protein has about 100 or more amino acids, up to a full length sequence which may be translated from a gene. Additionally, as used herein, a peptide can be a subsequence or a portion of a polypeptide or protein. In certain embodiments, the peptide consists of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In preferred embodiments, the peptide is from about 30 to about 100 amino acids in length. In some embodiments, the peptide is from about 40 to about 100 amino acids in length.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

As used herein, the term "prodrug" is intended to encompass therapeutic biologics which, under physiologic conditions, are converted into the therapeutically active biologics of the present disclosure. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. In certain embodiments, some or all of the molecules in a composition represented above can be replaced with the corresponding suitable prodrug, e.g., wherein a hydroxyl in the parent molecule is presented as an ester or a carbonate or carboxylic acid present in the parent therapeutic biologic is presented as an ester.

The meaning of the term "protein" is defined as a linear polymer built from about 20 different amino acids. The type and the sequence of amino acids in a protein are specified by the DNA that produces them. In certain embodiments, the sequences can be natural and unnatural. The sequence of amino acids determines the overall structure and function of a protein. In some embodiments, proteins can contain 50 or more residues. In preferred embodiments, proteins can contain greater than about 101 residues in length. A protein's net charge can be determined by two factors: 1) the total count of acidic amino acids vs. basic amino acids; and 2) the specific solvent pH surroundings, which expose positive or negative residues. As used herein, "net positively or net negatively charged proteins" are proteins that, under non-denaturing pH surroundings, have a net positive or net negative electric charge. In general, those skilled in the art will recognize that all proteins may be considered "net negatively charged proteins", regardless of their amino acid composition, depending on their pH and/or solvent surroundings. For example, different solvents can expose negative or positive side chains depending on the solvent pH. Proteins or peptides are preferably selected from any type of enzyme or antibodies or fragments thereof showing substantially the same activity as the corresponding enzyme or antibody. Proteins or peptides may serve as a structural material (e.g. keratin), as enzymes, as hormones, as transporters (e.g. hemoglobin), as antibodies, or as regulators of gene expression. Proteins or peptides are required for the structure, function, and regulation of cells, tissues, and organs.

The term "substantially" as used herein, refers to a majority of, or mostly, as in at least about 50%, 60%, 70%, 80%, 90%, 95%, 96%, 97%, 98%, 99%, 99.5%, 99.9%, 99.99%, or at least about 99.999% or more.

It is understood that the specific order or hierarchy of steps in the methods or processes disclosed is an illustration of exemplary approaches. Based upon design preferences, it is understood that the specific order or hierarchy of steps in the methods or processes may be rearranged. Some of the steps may be performed simultaneously. The accompanying methods claims present elements of the various steps in a sample order, and are not meant to be limited to a specific hierarchy or order presented. A phrase such as "embodiment" does not imply that such embodiment applies to all configurations of the subject technology. A disclosure relating to an embodiment may apply to all embodiments, or one or more embodiments. A phrase such as an embodiment may refer to one or more embodiments and vice-versa.

Particles

Unless otherwise defined, all terms of art, notations and other scientific terminology used herein, are intended to have the meanings commonly understood by those of skill in the art to which this disclosure pertains. In some cases, terms with commonly understood meanings are defined herein, for clarity and/or for ready reference, and the inclusion of such definitions herein, should not necessarily be construed to represent a substantial difference over what is generally understood in the art. The techniques and procedures described or referenced herein, are generally well understood and commonly employed using conventional methodology by those skilled in the art. As appropriate, procedures involving the use of commercially available kits and reagents are generally carried out in accordance with manufacturer defined protocols and/or parameters unless otherwise noted. As used herein, the phrase "and/or" when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The terms "particle" or "particles" or "microparticle" or "microparticles" are used herein, interchangeably in the broadest sense, refers to a discrete body or bodies. The particles described herein, are circular, spheroidal and of controlled dispersity with a characteristic size from sub-micrometers to tens of micrometers, in contrast to, e.g., a porous monolithic "cake", which is typically produced during conventional lyophilization. This morphology allows for a flowable powder (as described by low Hausner ratios) without post-processing. In some embodiments, the term "particle" refers to a quantity of a therapeutic biologic or therapeutic biologics which is either in a state of matter that is substantially solid as compared to a liquid droplet or in a gel form. The term "proto-particle" refers to a stage of particle formation in which one or more of the components comprising the particle are in an at least a partial state of desiccation. The total liquid content of the proto-particle is less than that of the droplet and greater than that of the formed particle. Similarly, the average concentration of the solutes is higher than that of the drop but typically less than that of the formed particle. In certain embodiments of the disclosure, proto-particles are formed in step c). The term "encapsulant" refers to a substance that can be dried or gelled around a particle core to form a shell.

As disclosed herein, a therapeutic biologic, also known as a biologic medical product, or biopharmaceutical, is any pharmaceutical drug product manufactured in, extracted from, or semisynthesized from biological sources. Therapeutic biologics can include a wide range of products such as vaccines, blood and blood components, allergenics, somatic cells, gene therapy, tissues, and recombinant therapeutic proteins. In some embodiments, the biologics can be composed of sugars, proteins, or nucleic acids or complex combinations of these substances, or may be living entities such as cells and tissues. Biologics can be isolated from a variety of natural sources, e.g., a human, animal, or microorganism, and may be produced by biotechnology methods or other technologies. Gene-based and cellular biologics, for example, are often used to treat a variety of medical conditions for which no other treatments are available. In certain embodiments of the disclosure, the therapeutic biologic is an antibody or fragment thereof, bovine serum albumin (BSA), or human serum albumin (HSA). In certain embodiments, the antibody is a human antibody, e.g., human IgG, or a monoclonal antibody (mAb). In certain other embodiments, the antibody is Rituximab or Trastuzumab. In still other embodiments, the antibody is a fragment of an antibody.

The terms "antibody" and "immunoglobulin" are used interchangeably in the broadest sense and include monoclonal antibodies, polyclonal antibodies, multivalent antibodies, and multispecific antibodies, regardless of how they are produced (i.e., using immunization, recombinant, synthetic methodologies). Antibodies can be gamma globulin proteins that are found in blood, or other bodily fluids of vertebrates that function in the immune system to bind antigen, hence identifying and/or neutralizing foreign objects. Antibodies can be assigned to different classes or isotypes. There are five classes of immunoglobulins: IgA, IgD, IgE, IgG, and IgM, having heavy chains designated alpha, delta, epsilon, gamma, and mu, respectively. The gamma class is further divided into subclasses based on the differences in sequences and function, e.g., humans express the following subclasses: IgG1, IgG2, IgG3, IgG4, IgA1, and IgA2. In certain embodiments of the disclosure, the IgG antibody is a human antibody. The L chain from any vertebrate species can be assigned to one of two clearly distinct types, e.g., kappa and lambda, based on the amino acid sequences of their constant domains.

The recognized immunoglobulin genes include the kappa, lambda, alpha, gamma, delta, epsilon and mu constant region genes, as well as the myriad immunoglobulin variable region genes. In some embodiments, light chains are classified as either kappa or lambda. In other embodiments, heavy chains are classified as gamma, mu, alpha, delta, or epsilon, which in turn define the immunoglobulin classes, IgG, IgM, IgA, IgD and IgE, respectively. In preferred embodiments of the disclosure, the antibody is an IgG antibody.

An exemplary antibody (immunoglobulin) structural unit comprises a tetramer. Each tetramer is composed of two identical pairs of polypeptide chains, each pair having one "light" (about sss25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "VL" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment. Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intra-chain disulfide bridges. H and L chains define specific Ig domains. In particular, each H chain has at the N-terminus, a variable domain (VH) followed by three constant domains (CH) for each of the alpha and gamma chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CHL). The constant domain includes the Fc portion which comprises the carboxy-terminal portions of both H chains held together by disulfides. The effector functions of antibodies such as ADCC are determined by sequences in the Fc region, which is also the part recognized by Fc receptors (FcR) found on certain types of cells.

As disclosed herein, the pairing of a VH and VL together form a "variable region" or "variable domain" including the amino-terminal domains of the heavy or light chain of the antibody. The variable domain of the heavy chain may be referred to as "VH". The variable domain of the light chain may be referred to as "VL". The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a β-sheet configuration and the hypervariable regions form loops connecting, and in some cases forming part of, the β-sheet structure. In certain embodiments, the "hypervariable region" refers to the regions of an antibody variable domain which are hypervariable in sequence and/or form structurally defined loops. Generally, antibodies comprise six hypervariable regions; three in the VH (H1, H2, H3), and three in the VL (L1, L2, L3). "Framework" or "FR" residues are those variable domain residues other than the hypervariable region residues defined herein.

The terms "full length antibody", "intact antibody" and "whole antibody" are used herein, interchangeably, to refer to an antibody in its substantially intact form, not as antibody fragments as defined above. The terms particularly refer to an antibody with heavy chains that contain the Fc region. A full length antibody can be a native sequence antibody or an antibody variant. In certain embodiments, an "intact" or "whole" antibody is one which comprises an antigen-binding site as well as a CL and at least heavy chain constant domains, CH1, CH2 and CH3. The constant domains may be native sequence constant domains (e.g. human native sequence constant domains) or amino acid sequence variants thereof.

As disclosed herein, "whole antibody fragments including a variable domain" include Fab, Fab', F(ab')$_2$, and Fv fragments; diabodies; linear antibodies, single-chain antibody molecules; and multispecific antibodies formed from antibody fragments. The "Fab fragment" consists of an entire L chain along with the variable region domain of the H chain (VH), and the first constant domain of one heavy chain (CHI). Each Fab fragment is monovalent with respect to antigen binding, i.e., it has a single antigen-binding site. A "Fab' fragment" differs from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. A "F(ab')$_2$ fragment" roughly corresponds to two disulfide linked Fab fragments having divalent antigen-binding activity and is still capable of cross-linking antigen. An "Fv" is the minimum antibody fragment which contains a complete antigen-recognition and binding site. This fragment consists of a dimer of one heavy and one light chain variable region domain in tight, non-covalent association. In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. "Single-chain Fv" also abbreviated as "sFv" or "scFv" are antibody fragments that comprise the VH and VL antibody domains connected to form a single polypeptide chain. In preferred embodiments, the scFv polypeptide further comprises a polypeptide linker between the VH and VL domains which enables the scFv to form the desired structure for antigen binding. In some embodiments, a "single variable domain" is half of an Fv (comprising only three CDRs specific for an antigen) that has the ability to recognize and bind antigen, although at a lower affinity than the entire binding site.

In some embodiments, "diabodies" refer to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. In other embodiments, diabodies may be bivalent or bispecific. In certain embodiments, bispecific diabodies are heterodimers of two "crossover" sFv fragments in which the VH and VL domains of the two antibodies are present on different polypeptide chains. Triabodies and tetrabodies are also generally known in the art.

"Antigen binding fragments" of antibodies as described herein, comprise only a portion of an intact antibody, generally including an antigen binding site of the intact antibody and thus retaining the ability to bind antigen. Exemplary examples of antibody fragments encompassed by the present definition include but are not limited to: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd, segments (VH-CH1-VH-CH1) which, together with complementary light chain polypeptides, form a pair of antigen binding regions. In some embodiments, an "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')$_2$ or scFv) in a method described herein. In some embodiments, an antigen-binding fragment competes with intact antibody, e.g., with the intact antibody from which the fragment was derived, for antigen binding.

The term "fragment" refers to a part or portion of an antibody or antibody chain comprising fewer amino acid residues than an intact or complete antibody or antibody chain. As used herein, the term "fragment" of an antibody includes Fc fragments and antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, or any antigen-binding molecule formed by combination, assembly or conjugation of such antigen binding fragments. In particular embodiments, the fragment is an Fc fragment.

In certain embodiments, the term "single-chain Fv" or "scFv" or "single chain" antibody can refer to antibody fragments comprising the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies (mAbs) are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The monoclonal antibodies may also be isolated from phage antibody libraries using molecular engineering techniques. The monoclonal antibodies of the disclosure may be generated by recombinant DNA methods, and are sometimes referred to as "recombinant antibodies" or "recombinant monoclonal antibodies" as described herein. In some embodiments, a monoclonal antibody is a single species of antibody wherein every antibody molecule recognizes the same epitope because all antibody producing cells are derived from a single B-lymphocyte cell line. The methods for generating monoclonal antibodies (mAbs) generally begin along the same lines as those for preparing polyclonal antibodies. In other embodiments, rodents such as mice and rats are used in generating monoclonal antibodies. In certain embodiments, rabbit, sheep, or frog cells are used in generating monoclonal antibodies. The use of rats is well known and may provide certain advantages. Mice (e.g., BALB/c mice) are routinely used and generally give a high percentage of stable fusions. In still other embodiments of the disclosure, the antibody is a monoclonal antibody. In preferred embodiments of the disclosure, the IgG antibody is monoclonal.

In other embodiments, recombinant antibody fragments may be isolated from phage antibody libraries using techniques well known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

An "isolated antibody" is one that has been identified and separated and/or recovered from a component of its preexisting environment. Contaminant components are materials that would interfere with therapeutic uses for the antibody, and may include enzymes, hormones, and other proteinaceous or nonproteinaceous solutes.

As used herein, a "human antibody" refers to an antibody that possesses an amino acid sequence that corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci has been disabled. "Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

An "affinity matured" antibody is one with one or more alterations in one or more hypervariable region thereof that result in an improvement in the affinity of the antibody for antigen, compared to a parent antibody that does not possess those alterations. In some embodiments, affinity matured antibodies can have micromolar affinities for the target antigen. In other embodiments, affinity matured antibodies can have nanomolar or even picomolar affinities for the target antigen. Affinity matured antibodies are produced by procedures known in the art.

A "blocking" antibody or an "antagonist" antibody is one that inhibits or reduces biological activity of the antigen it binds. In some embodiments, blocking antibodies or antagonist antibodies substantially or completely inhibit the biological activity of the antigen. An "agonist antibody", as used herein, is an antibody, which mimics at least one of the functional activities of a polypeptide of interest.

"Binding affinity" generally refers to the strength of the sum total of noncovalent interactions between a single binding site of a molecule, e.g., an antibody, and its binding partner, e.g., an antigen. Unless indicated otherwise, as used herein, "binding affinity" refers to intrinsic binding affinity, which reflects a 1:1 interaction between members of a binding pair, e.g., antibody and antigen. The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. "Epitope" generally refers to that part of an antigen that is bound by the antigen binding site of an antibody. In some embodiments, an epitope may be "linear" in the sense that the hypervariable loops of the antibody CDRs that form the antigen binding site bind to a sequence of amino acids as in a primary protein structure. In other embodiments, the epitope is a "conformational epitope", i.e. one in which the hypervariable loops of the CDRs bind to residues as they are presented in the tertiary or quaternary protein structure.

In some embodiments of the foregoing methods, the therapeutic biologic is an antibody. In other embodiments, the antibody includes but are not limited to 3F8, Abagovomab, Abatacept, Abciximab, Abituzumab, Abrezekimab, Abrilumab, Acritumomab, Actoxumab, Abituzumab, Adalimumab-adbm, Adalimumab-atto, Adalimumab-bwwb, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab, Ansuvimab, Apolizumab, Aprutumab ixadotin, Arcitumomab, Ascrinvacumab, Aselizumab, Atezolizumab, Atidortoxumab, Atinumab, Atlizumab, Atoltivimab, Atorolimumab, Avelumab, Azintuxizumab vedotin, Bapineuzumab, Basiliximab, Bavituximab, BCD-100, Bectumomab, Begelomab, Belantamab mafodotin, Belatacept, Belimumab, Bemarituzumab, Benralizumab, Bermekimab, Bersanlimab, Bertilimumab, Besilesomab, Bevacizumab, Bevacizumab-awwb, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumumab, Dectrekumab, Demcizumab, Denileukin diftitox, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotumab, Dupilumab, Durvalumab, Dusigitumab, Duvortuxizumab, Ecromeximab, Eculizumab, Edobacomab, Edrecolomab, Efalizumab, Efgartigimod, Efungumab, Eldelumab, Elezanumab, Elgemtumab, Elotuzumab, Elsilimomab, Emactuzumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Etaracizumab, Etigilimab, Etrolizumab, Evinacumab, Evolocumab, Exbivirumab, Factor VIII Fc fusion protein, Factor IX Fc fusion protein, Fanolesomab, Faralimomab, Faricimab, Farletuzumab, Fasinumab, Felvizumab, Fezakinumab, Fibatuzumab, Ficlatuzumab, Figitumumab, Filgrastim, Filgrastim-sndz, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Infliximab-abda, Infliximab-dyyb, Infliximab-qbtx, Intetumab, Inolimomab, Inotuzumab ozogamicin, Ipilimumab, Iomab-B, Iratumumab, Isatuximab, Isatuximab-irfe, Iscalimab, Istiratumab, Itolizumab, Ixekizumab, Kelixumab, Labetuzumab, Lacnotuzumab, Ladiratuzumab vedotin, Lambrolizumab, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Maftivimab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odesivimab, Odesivimab-ebgn, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pegfilgrastim-jmdb, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilonacept, Rilotumumab, Rinucumab, Risankizumab, Rituximab, Rituximab-abbs, Rituximab-arrx, Rituximab-pvvr, Rivabazumab pegol, Rivabazumab pegol, Robatumumab, Rmab, Roledumab, Romilkimab, Romiplostim, Romosozumab, Rontalizumab, Rosmantuzumab, Rovalpituzumab tesirine, Rovalpituzumab tesirine, Rovelizumab, Rozanolixizumab, Ruplizumab, Sacituzumab govitecan, Samalizumab, Samrotamab vedotin, Sapelizumab, Sarilumab, Satralizumab (SA237), Satumomab pendetide, Secukinumab, Selicrelumab, Seribantumab, Setoxaximab, Setrusumab, Sevirumab, Sibrotuzumab, SGN-CD19A, SGN-CD33A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Tafasitamab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Ticilimumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab-anns, Trastuzumab-dkst, Trastuzumab-dttb, Trastuzumab emtansine, Trastuzumab-pkrb, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Xentuzumab, XMAB-5574, Zalutumumab, Zanolimumab, Zatuximab, Zenocutuzumab, Ziralimumab, Zolbetuximab (IMAB362, Claudiximab), Ziv-aflibercept, or Zolimomab aritox.

In other embodiments of the foregoing methods, the antibody is monoclonal. In certain embodiments, the monoclonal antibody includes but are not limited to 3F8, 8H9, Abatacept, Abagovomab, Abciximab, Abituzumab, Adalimumab-adbm, Adalimumab-atto, Adalimumab-bwwb, Abrilumab, Actoxumab, Abituzumab, Abrezekimab, Abrilumab, Actoxumab, Adalimumab, Adecatumumab, Ado-trastuzumab emtansine, Aducanumab, Afasevikumab, Afelimomab, Aflibercept, Afutuzumab, Alacizumab pegol, ALD518, Alefacept, Alemtuzumab, Alirocumab, Altumomab pentetate, Amatuximab, Anatumomab mafenatox, Andecaliximab, Anetumab ravtansine, Anifrolumab, Anrukinzumab (IMA-638), Ansuvimab, Apolizumab, Arcitumomab, Ascrinvacumab, Aselizumab, Atezolizumab, Atidortoxumab, Atinumab, Atlizumab (tocilizumab), Atoltivimab, Atorolimumab, Avelumab, Bapineuzumab, Basiliximab, Bevacizumab, Bevacizumab-awwb, BCD-100, Bectumomab, Begelomab, Belatacept, Belimumab, Bemarituzumab, Benralizumab, Bermekimab, Bersanlimab, Bertilimumab, Besilesomab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camrelizumab, Canakinumab, Cantuzumab mertansine, Cantuzumab ravtansine, Caplacizumab, Capromab pendetide, Carlumab, Carotuximab, Catumaxomab, Cedelizumab, Cemiplimab, Certolizumab pegol, Cetrelimab, Cetuximab, Cibisatamab, Cirmtuzumab, Ch. 14.18, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, CR6261, Crizanlizumab, Crotedumab, Cusatuzumab, Dacetuzumab, Daclizumab, Dalotuzumab, Dapirolizumab pegol, Daratumumab, Dectrekumab, Demcizumab, Denileukin diftitox, Denintuzumab mafodotin, Denosumab, Derlotuximab biotin, Detumomab, Dezamizumab, Dinutuximab, Diridavumab, Domagrozumab, Dorlimomab aritox, Dostarlimab, Drozitumab, Duligotumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epoetin-alfa, Epoetin-alfa-epbx, Epratuzumab, Eptinezumab, Erenumab, Erlizumab, Ertumaxomab, Etanercept, Etanercept-szzs, Etaracizumab, Etigilimab, Etrolizumab, Evinacumab, Evolocumab, Exbivirumab, Factor VIII Fc fusion protein, Factor IX Fc fusion protein, Fanolesomab, Faralimomab, Faricimab, Farletuzumab, Fasinumab, FBTA05, Felvizumab, Fezakinumab, Fibatuzumab, Ficlatuzumab, Figitumumab, Filgrastim, Filgrastim-sndz, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ibalizumab, IBI308, Ibritumomab tiuxetan, Icrucumab, Idarucizumab, Ifabotuzumab, Igovomab, IMAB362, Imalumab, Imaprelimab, Imciromab, Imgatuzumab, Inclacumab, Indatuximab ravtansine, Indusatumab vedotin, Inebilizumab, Infliximab, Infliximab-abda, Infliximab-dyyb, Infliximab-qbtx, Intetumumab, Inolimomab, Inotuzumab ozogamicin, Ipilimumab, Iratumumab, Isatuximab, Isatuximab-irfe, Iscalimab, Istiratumab, Itolizumab, Ixekizumab, Keliximab, Labetuzumab, Lacnotuzumab, Lambrolizumab, Lampalizumab, Lanadelumab, Landogrozumab, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lutikizumab, Maftivimab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odesivimab, Odesivimab-ebgn, Odulimomab, Ofatumumab, Olaratumab, Olecumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pegfilgrastim-jmdb, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Tetulomab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilonacept, Rilotumumab, Rinucumab, Risankizumab-rzaa, Rituximab, Rituximab-abbs, Rituximab-arrx, Rituximab-pvvr, Robatumumab, Rmab, Roledumab, Romilkimab, Romiplostim, Romosozumab, Rontalizumab, Rosmantuzumab, Rovelizumab, Rozanolixizumab, Ruplizumab, Sacituzumab govitecan, Samalizumab, Sarilumab, Satralizumab (SA237), Satumomab pendetide, Secukinumab, Selicrelumab, Seribantumab, Setoxaximab, Setrusumab, Sevirumab, Sibrotuzumab, SGN-CD19A, SGN-CD33A, SHP647, Sifalimumab, Siltuximab, Simtuzumab, Siplizumab, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Tafasitamab, Talacotuzumab, Talizumab, Tamtuvetmab, Tanezumab, Taplitumomab paptox, Tarextumab, Tavolimab, Tefibazumab, Telimomab aritox, Tenatumomab, Teneliximab, Teplizumab, Tepoditamab, Teprotumumab, Tesidolumab, Tetulomab (lilotomab), Tezepelumab, TGN1412, Tibulizumab, Ticilimumab (tremelimumab), Tildrakizumab, Tigatuzumab, Timigutuzumab, Timolumab, Tiragotumab, Tislelizumab, TNX-650, Tocilizumab (atlizumab), Tomuzotuximab, Toralizumab, Tosatoxumab, Tositumomab, Tovetumab, Tralokinumab, Trastuzumab, Trastuzumab-anns, Trastuzumab-dkst, Trastuzumab-dttb, Trastuzumab emtansine, Trastuzumab-pkrb, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Xentuzumab, XMAB-5574, Zalutumumab, Zanolimumab, Zatuximab, Zenocutuzumab, Ziralimumab, Zolbetuximab (IMAB362, Claudiximab), Ziv-aflibercept, Zolimomab aritox or the corresponding anti-drug antibody in a sample from a human patient. In some embodiments, the monoclonal antibody is Atoltivimab, Maftivimab, Odesivimab-ebgn, or a combination thereof. In preferred embodiments, the monoclonal antibody is Rituximab, Rituximab-abbs, Rituximab-arrx, or Rituximab-pvvr.

In some embodiments, the monoclonal antibody is a biosimilar. In other embodiments, the biosimilar includes but are not limited to Adalimumab-adbm, Adalimumab-atto, Adalimumab-bwwb, Bevacizumab-awwb, Epoetin alfa-epbx, Etanercept-szzs, Infliximab-abda, Infliximab-dyyb, Infliximab-qbtx, Isatuximab-irfc, Filgrastim-sndz, Odesivimab-ebgn, Pegfilgrastim-jmdb, Pegfilgrastim-bmez, Risankizumab-rzaa, Rituximab-abbs, Rituximab-arrx, Rituximab-pvvr, Trastuzumab-anns, Trastuzumab-dttb, Trastuzumab-pkrb, or Trastuzumab-dkst. In certain embodiments, the active biosimilar substance is Adalimumab, Bevacizumab, Enoxaparin sodium, Epoetin alfa, Epoetin zeta, Etanercept, Filgrastim, Follitropin alfa, Infliximab, Insulin glargine, Insulin lispro, Isatuximab-irfc, Pegfilgrastim, Risankizumab, Rituximab, Rituximab-abbs, Rituximab-arrx, Rituximab-pvvr, Somatropin, Teriparatide, or Trastuzumab. In preferred embodiments, the biosimilar is Rituximab, Rituximab-abbs, Rituximab-arrx, or Rituximab-pvvr.

In other embodiments, the targeting moiety is an antibody from an intact polyclonal antibody, an intact monoclonal antibody, an antibody fragment, a single chain Fv (scFv) mutant, a multispecific antibody, a bispecific antibody, a chimeric antibody, a humanized antibody, a human antibody, a fusion protein comprising an antigenic determinant portion of an antibody, or other modified immunoglobulin molecules comprising antigen recognition sites.

In some embodiments, the therapeutic biologic is an immunotherapy. In other embodiments, the immunotherapy is an anti-CD20 antibody. In certain embodiments, the anti-CD20 antibody is rituximab. In certain other embodiments, the therapeutic biologic is an anti-CD20 antibody. As described herein, any antibody capable of binding the CD20 antigen may be used in the methods of the instant disclosure. Antibodies which bind the CD20 antigen include, for example: C2B8 (rituximab; RITUXAN®) (U.S. Pat. No. 5,736,137, expressly incorporated herein by reference); the yttrium-[90]-labeled 2138 murine antibody designated Y2B8 (U.S. Pat. No. 5,736,137, expressly incorporated herein by reference); murine IgG2a 131 optionally labeled with 131 1 to generate the 131 1-B1 antibody (BEXXAR®) (U.S. Pat. No. 5,595,721, expressly incorporated herein by reference); murine monoclonal antibody 1F5 (Press et al. Blood 69(2): 584-591 (1987)); chimeric 2H7 antibody (U.S. Pat. No. 5,677,180 expressly incorporated herein by reference); and monoclonal antibodies L27, G28-2, 93-1 133, B-Cl or NU-B2 available from the International Leukocyte Typing Workshop (Valentine et al., In: Leukocyte TypingIII (McMichael, Ed., p. 440, Oxford University Press (1987)).

In certain embodiments of the disclosure, the anti-CD20 antibody is rituximab. Rituximab is a genetically engineered chimeric murine/human monoclonal antibody. Rituximab is an IgG, kappa immunoglobulin containing murine light and heavy chain variable region sequences and human constant region sequences. Rituximab has a binding affinity for the CD20 antigen of approximately 8.0 nM and is commercially available, e.g., from Genentech (South San Francisco, Calif.).

In some embodiments, the therapeutic biologic is an immunotherapeutic. In other embodiments, the immunotherapeutic is a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In still other embodiments, the immunotherapeutic is a PD-1 inhibitor (e.g., nivolumab, pembrolizumab, pidilizumab, BMS 936559, and MPDL3280A). In some embodiments, the immunotherapy is a PD-L1 inhibitor (e.g., atezolizumab and MEDI4736). In some embodiments, the immunotherapeutic is a CTLA-4 inhibitor (e.g., ipilimumab). In certain other embodiments, the immunotherapeutic is a CSF-1R inhibitor (e.g., pexidartinib and AZD6495). In certain embodiments, the immunotherapeutic is an IDO inhibitor (e.g., norharmane, rosmarinic acid, and alpha-methyl-tryptophan). In some embodiments, the immunotherapeutic is an A1 adenosine inhibitor (e.g., 8-cyclopentyl-1,3-dimethylxanthine, 8-cyclopentyl-1,3-dipropylxanthine, 8-phenyl-1,3-dipropylxanthine, bamifylline, BG-9719, BG-9928, FK-453, FK-838, rolofylline, or N-0861). In other embodiments, the immunotherapeutic is an A2A adenosine inhibitor (e.g., ATL-4444, istradefylline, MSX-3, preladenant, SCH-58261, SCH-412,348, SCH-442,416, ST-1535, VER-6623, VER-6947, VER-7835, viadenant, or ZM-241,385). In still other embodiments, the immunotherapeutic is an A2B adenosine inhibitor (e.g., ATL-801, CVT-6883, MRS-1706, MRS-1754, OSIP-339,391, PSB-603, PSB-0788, or PSB-1115). In certain other embodiments, the immunotherapeutic is an A3A adenosine inhibitor (e.g., KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421). In certain embodiments, the immunotherapeutic is an arginase inhibitor (e.g., an arginase antibody, (2s)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapeutic is an HDAC inhibitor (e.g., valproic acid, SAHA, or romidepsin). In other embodiments, the immunotherapeutic is a toll-like receptor activator. In still other embodiments, the immunotherapy is a RIG-I-like receptor activator. In certain other embodiments, the immunotherapeutic is a stimulator of interferon genes (STING) pathway activator. In certain embodiments, the immunotherapeutic is an Interleukin-1 receptor agonist, e.g., an IL-R1 antagonist. In some embodiments, the immunotherapeutic is a PTEN inhibitor, e.g., a bisperoxovanadium compound. In other embodiments, the immunotherapeutic is a tumor necrosis factor receptor (TNFR), e.g., TNFR-1 or TNFR-2 inhibitor. In certain embodiments, the immunotherapeutic is a Lymphocyte-activation gene 3 (LAG-3) inhibitor, e.g., GSK2831781.

In other embodiments, the therapeutic biologic is ledipasvir/sofosbuvir, insulin glargine, lenalidomide, pneumococcal 13-valent conjugate vaccine, fluticasone/salmeterol, elvitegravir/cobicistat/emtricitabine/tenofovir alafenamide, emtricitabine, rilpivirine and tenofovir alafenamide, emtricitabine/tenofovir alafenamide, grazoprevir/elbasvir, coagulation factor VIIa recombinant, epoetin alfa, Aflibercept or etanercept.

In some embodiments, the therapeutic biologic is Abatacept, AbobotulinumtoxinA, Agalsidase beta, Albiglutide, Aldesleukin, Alglucosidase alfa, Alteplase (cathflo activase), Anakinra, Asfotase alfa, Asparaginase, *Asparaginase Erwinia chrysanthemi*, Becaplermin, Belatacept, Collagenase, Collagenase *Clostridium histolyticum*, Darbepoetin alfa, Denileukin diftitox, Dornase alfa, Dulaglutide, Ecallantide, Elosulfase alfa, Etanercept-szzs, Filgrastim, Filgrastim-sndz, Galsulfase, Glucarpidase, Idursulfase, IncobotulinumtoxinA, Interferon alfa-2b, Interferon alfa-n3, Interferon beta-1a, Interferon beta-1b, Interferon gamma-1b, Laronidase, Methoxy polyethylene glycol-epoetin beta, Metreleptin, Ocriplasmin, OnabotulinumtoxinA, Oprelvekin, Palifermin, Parathyroid hormone, Pegaspargase, Pegfilgrastim, Peginterferon alfa-2a, Peginterferon alfa-2a co-packaged with ribavirin, Peginterferon alfa-2b, Peginterferon beta-1a, Pegloticase, Rasburicase, Reteplase, Rilonacept, RimabotulinumtoxinB, Romiplostim, Sargramostim, Sebelipase alfa, Tbo-filgrastim, Tenecteplase, or Ziv-aflibercept.

The therapeutic biologic in the particles may have an activity per unit of about 0.5 to about 1.0, about 0.75 to about 1.0 activity per unit, or about 0.9 to about 1.0 activity per unit. Activity is measured relative to the same therapeutic biologic prior to particle formation. In preferred embodiments, the therapeutic biologic has an activity per unit of about 0.5 to about 1.0. The term "activity" refers to the ratio of a functional or structural aspect of a therapeutic biologic, e.g., an antibody, antibody fragment, bovine serum albumin (BSA), or human serum albumin (HSA), at two points in time. The denominator of the ratio corresponds to a measure of the functional or structural aspect of the therapeutic biologic in the feed solution, immediately in advance of droplet formation. The numerator of the ratio corresponds to the same measure of a functional or structural aspect of the therapeutic biologic at a later point in time, e.g., immediately after particle formation.

In some embodiments, the particles have less than about 25% internal void spaces, e.g., less than about 24, 20, 15, 10, 9, 8, 7, 6, 5, 4, 3, 2, 1, or 0.5% internal void spaces after removing the aqueous first liquid and organic second liquid from the mixture. In certain embodiments, the particle includes less than about 10% internal void spaces, less than about 5% internal void spaces, less than about 1% internal void spaces, or less than about 0.5% internal void spaces, after removing the aqueous first liquid and organic second liquid from the mixture. In preferred embodiments, the particle is substantially free from any internal void spaces after removing the aqueous first liquid and organic second liquid from the mixture. Suitable methods for determining internal void space can be performed using Focused Ion Beam Scanning Electron Microscopy (FIB-SEM), which can be used to visualize "accessible" and "inaccessible" void spaces, or gas displacement pycnometry (Micromeritics Instrument Corporation of Norcross, Ga.), which can determine "accessible" voids (void spaces accessible from the surface rather than those resembling a core-shell structure that are "unaccessible form the surface"). Gas pycnometry is a common analytical technique that uses a gas displacement method to measure volume. Inert gases, such as helium or nitrogen, are used as the displacement medium. True volume is total volume minus volume accessible to the gas. Density is calculated by dividing sample weight with true volume. The sample is sealed in the instrument compartment of a known volume, the appropriate inert gas is admitted, and then expanded into another precision internal volume. The pressure before and after expansion is measured and used to compute the sample volume. Dividing this volume into the sample weight gives the gas displacement density. Cross-sections of typical particles of the disclosure indicate an absence of pores (substantially free from any internal void spaces) and low particle porosity as shown by FIB-SEM or by gas pycnometry using helium at temperatures at about 22° C. to provide densities typically averaging about 1.3 g/cm$^3$ with standard deviations at about 0.0005 g/cm$^3$. For example, internal void space can be calculated using the following formula: internal void space=$A_v/A_p$, where $A_v$ is the total area of void spaces and $A_p$ is the total area of the particle.

In other embodiments, the particles may exhibit a porosity from about 0 to about 50% after removing the aqueous first liquid and organic second liquid from the mixture, e.g., from about 0 to about 10%, from about 0 to about 5%, from about 0 to about 1%, from about 0 to about 0.5%, from about 0 to about 0.1%, or from about 0 to about 0.01% after removing the aqueous first liquid and organic second liquid from the mixture. Exemplary pore size measurements include scanning electron microscopy (SEM), transmission electron microscopy (TEM), and confocal laser scanning microscopy analysis. A gallium focused ion beam (FIB) was used to cut one of the particles in half to reveal a cross-section of the particle interior. The specific surface area of porous micro- and nanospheres may also be investigated by nitrogen adsorption/desorption analysis and a Brunauer-Emmett-Teller adsorption model. In certain embodiments where the pore sizes are sufficiently large, mercury-intrusion porosimetry may be employed.

The particles according to the disclosure are circular. Circularity can serve as an indicator of the shape of the particle. The particles described herein, can have a characteristic circularity, e.g., have a relative shape, that is substantially circular. This characteristic describes and defines the form of a particle on the basis of its circularity. The circularity is 1.0 when the particle has a completely circular structure. Particles as described herein, have a circularity of about 0.8, 0.9, 0.95, 0.96, 0.97, 0.98, or 0.99 after removing the aqueous first liquid and organic second liquid from the mixture; greater than about 0.80, greater than about 0.90, greater than about 0.95, or greater than about 0.98 after removing the aqueous first liquid and organic second liquid from the mixture. In some embodiments, the circularity of the particles is greater than about 0.88 after removing the aqueous first liquid and organic second liquid from the mixture. In other embodiments, the circularity of the particles is greater than about 0.90 after removing the aqueous first liquid and organic second liquid from the mixture. In certain embodiments, the circularity of the particles is greater than about 0.93 after removing the aqueous first liquid and organic second liquid from the mixture. In preferred embodiments, the circularity of the particles is greater than about 0.97 after removing the aqueous first liquid and organic second liquid from the mixture. The diameter and the circularity of the particles can be determined by the image processing of an image observed under an electron microscope or the like or a flow-type particle image analyzer. The circularity can also be determined by subjecting particles to circularity measurement and averaging the resulting values. For example, circularity (circ) can be calculated using the following formula:

$$circ = 4 * \pi * \frac{\text{Area}}{\text{Perimeter}^2}. \quad \text{Eq. 1}$$

The term "perimeter", as used herein, refers to the boundary of a closed plane figure or the sum of all borders of a two-dimensional image. As used herein, the term "area", refers to the crossectional area of a two-dimensional image of a particle. The circularity of a particle can also be described as the ratio of the smallest dimension of the particle to its largest diameter. For a perfect circle, the ratio is 1. The percentage circularity can be calculated by multiplying the circularity by 100. The circularity can be calculated, for example, by measuring the aspect ratio using any software adapted to deal with images, for example, images obtained by microscopy, in particular, scanning electron microscopy (SEM) or transmission electron microscopy (TEM). In some embodiments, the circularity of the particles is at least about 10% after removing the aqueous first liquid and organic second liquid from the mixture, e.g., at least about 20, 30, 40, 50, 55, 60, 65, 70, 75, 80, 85, 90, 91, 92, 93, 94, 95, 96, 97, 98, 99, or about 100% after removing the aqueous first liquid and organic second liquid from the mixture. In other embodiments, the circularity of the particles is at least about 88% after removing the aqueous first liquid and organic second liquid from the mixture. In certain embodiments, the circularity of the particles is at least about 90% after removing the aqueous first liquid and organic second liquid from the mixture. In still other embodiments, the circularity of the particles is at least about 93% after removing the aqueous first liquid and organic second liquid from the mixture. In preferred embodiments, the circularity of the particles is at least about 97% after removing the aqueous first liquid and organic second liquid from the mixture.

In some embodiments, the circularity of the particles is from about 0.10 to about 1.00 after removing the aqueous first liquid and organic second liquid from the mixture, e.g., from about 0.20, 0.30, 0.40, 0.50. 0.60, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99 to about 1.00 after removing the aqueous first liquid and organic second liquid from the mixture. In certain embodiments, the circularity of the particle is from about 0.88 to about 1.00 after removing the aqueous first liquid and organic second liquid from the mixture. In still other embodiments, the circularity of the particles is from about 0.90 to about 1.00 after removing the aqueous first liquid and organic second liquid from the mixture. In certain other embodiments, the circularity of the particles is from about 0.93 to about 1.00 after removing the aqueous first liquid and organic second liquid from the mixture. In preferred embodiments, the circularity of the particles is from about 0.97 to about 1.00 after removing the aqueous first liquid and organic second liquid from the mixture. In other embodiments, methods of measuring particle circularity include image analysis of scanning electron micrographs of the particles in which the average roundness is calculated on the basis of the cross-sectional shapes of the particles projected onto the plane of the image. Such roundness factors can be extended to identify the corresponding circularity.

In other embodiments of the disclosure, the drying operation may be controlled to provide particles having particular characteristics, such as particles having a substantially smooth surface. "Surface roughness", as used herein, means a particle having numerous wrinkles or creases, e.g., being ridged or wrinkled. The term "pit", as used herein, refers to an indentation or crevice in the particle, either an indentation or crevice in the two-dimensional image or an indentation or crevice in an object. The term "spike", as used herein, refers to a projection pointing outward from the centroid of a particle, a projection pointing outward from the centroid of a two-dimensional image or a sharp projection pointing outward from an object.

In preferred embodiments of the disclosure, the particles as described herein, have a surface morphology that is smooth rather than ridged or wrinkled. The surface roughness of the particles may be decreased by controlling the formulation and/or process to form the particles as described herein. In certain embodiments, the drying conditions can be selected to control the particle morphology in order to enhance the smoothness of the particle's surface. In particular, the drying conditions can be selected to provide particles having a substantially smooth surface. In certain preferred embodiments, the particles have a substantially smooth surface after removing the aqueous first liquid and organic second liquid from the mixture. A person of ordinary skill in the field of this disclosure can readily assess the surface morphology of the disclosed particles using routine and standard techniques.

In some embodiments, the particle has a diameter of about 0.1 to about 1000 µm after removing the aqueous first liquid and organic second liquid from the mixture, e.g., about 0.1 to about 900, 800, 700, 600, 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, or about 0.2 µm after removing the aqueous first liquid and organic second liquid from the mixture. In certain embodiments, the particle has a diameter of about 1 to about 100 µm after removing the aqueous first liquid and organic second liquid from the mixture, e.g., about 2, 3, 4, 5, 6, 7, 8, 9, 10, 11, 12, 13, 14, 15, 16, 17, 18, 19, 20, 25, 30, 35, 40, 45, or 50 to about 100 µm after removing the aqueous first liquid and organic second liquid from the mixture. In still other embodiments, the particle has a diameter of about 4 to about 100 µm after removing the aqueous first liquid and organic second liquid from the mixture. In certain other embodiments, the particle has a diameter of about 10 to about 100 μm after removing the aqueous first liquid and organic second liquid from the mixture. In preferred embodiments, the particle has a diameter of about 20 to about 50 μm after removing the aqueous first liquid and organic second liquid from the mixture. In certain preferred embodiments, the particle is intentionally controlled in its diameter. In other embodiments, the particles have diameters from about 0.1 to about 1000 μm after removing the aqueous first liquid and organic second liquid from the mixture, e.g., about 1 to about 400 μm, about 1 to about 200 μm, about 1 to about 100 μm, about 1 to about 50 μm, about 1 to about 25 μm, about 1 to about 10 μm, about 10 to about 100 μm, about 50 to about 100 μm, about 50 to about 75 μm, or about 75 to about 100 μm after removing the aqueous first liquid and organic second liquid from the mixture. In some embodiments, the particles have diameters from about 1 to about 100 μm after removing the aqueous first liquid and organic second liquid from the mixture, e.g., from about 4 to about 100 μm, from about 10 to about 100 μm, or from about 20 to about 50 μm after removing the aqueous first liquid and organic second liquid from the mixture.

In certain embodiments, the particle has a diameter of about 0.1 to about 1000 μm after removing the aqueous first liquid and organic second liquid from the mixture. In certain other embodiments, the particle has a diameter of about 1 to about 100 μm after removing the aqueous first liquid and organic second liquid from the mixture. In still other embodiments, the particle has a diameter of about 5 to about 100 μm after removing the aqueous first liquid and organic second liquid from the mixture. In certain preferred embodiments, the particle has a diameter of about 5 to about 50 μm after removing the aqueous first liquid and organic second liquid from the mixture. In preferred embodiments, the particle has a diameter of about 5 to about 20 μm after removing the aqueous first liquid and organic second liquid from the mixture.

In other embodiments, the particles exhibit a skeletal density from about 1.00 to about 6.00 g/cm$^3$ after removing the aqueous first liquid and organic second liquid from the mixture, e.g., from about 1.00 to about 5.00 g/cm$^3$, from about 1.00 to about 3.00 g/cm$^3$, from about 1.00 to about 2.00 g/cm$^3$, from about 1.00 to about 1.50 g/cm$^3$, from about 1.30 to about 1.50 g/cm$^3$, from about 1.30 to about 1.50 g/cm$^3$, or from about 1.10 to about 1.40 g/cm$^3$ after removing the aqueous first liquid and organic second liquid from the mixture. In some embodiments, the particles exhibit a skeletal density from about 0.10 to about 5.00 g/cm$^3$ after removing the aqueous first liquid and organic second liquid from the mixture, e.g., from about 0.10 to about 2.50 g/cm$^3$, from about 0.10 to about 1.40 g/cm$^3$, from about 0.50 to about 1.40 g/cm$^3$, or from about 1.00 to about 1.40 g/cm$^3$ after removing the aqueous first liquid and organic second liquid from the mixture. In certain embodiments, the particle has a skeletal density of about 0.90 to about 1.60 g/cm$^3$ after removing the aqueous first liquid and organic second liquid from the mixture. In still other embodiments, the particle has a skeletal density of about 1.30 to about 1.58 g/cm$^3$ after removing the aqueous first liquid and organic second liquid from the mixture. In preferred embodiments, the particle has a skeletal density of about 1.30 to about 1.50 g/cm$^3$ after removing the aqueous first liquid and organic second liquid from the mixture. The terms "skeletal density", "envelope density" and "density" may be used interchangeably. The terms "skeletal density", "envelope density" or "density" as used throughout the specification, examples, and claims is intended to show pore volume and internal void space of the particles. Exemplary methods of skeletal density measurements include gas displacement pycnometry and/or mercury intrusion.

In certain embodiments, the particles have a skeletal density of about 1000 mg/mL to about 1500 mg/mL, about 1050 mg/mL to about 1500 mg/mL, about 1100 mg/mL to about 1500 mg/mL, about 1150 mg/mL to about 1500 mg/mL, about 1200 mg/mL to about 1500 mg/mL, about 1250 mg/mL to about 1500 mg/mL, about 1300 mg/mL to about 1500 mg/mL, about 1310 mg/mL to about 1500 mg/mL, about 1320 mg/mL to about 1500 mg/mL, about 1330 mg/mL to about 1500 mg/mL, about 1340 mg/mL to about 1500 mg/mL, about 1350 mg/mL to about 1500 mg/mL, about 1360 mg/mL to about 1500 mg/mL, about 1370 mg/mL to about 1500 mg/mL, about 1380 mg/mL to about 1500 mg/mL, about 1390 mg/mL to about 1500 mg/mL, about 1400 mg/mL to about 1500 mg/mL, about 1410 mg/mL to about 1500 mg/mL, about 1420 mg/mL to about 1500 mg/mL, about 1430 mg/mL to about 1500 mg/mL, about 1440 mg/mL to about 1500 mg/mL, about 1450 mg/mL to about 1500 mg/mL, about 1460 mg/mL to about 1500 mg/mL, about 1470 mg/mL to about 1500 mg/mL, about 1480 mg/mL to about 1500 mg/mL, about 1490 mg/mL to about 1500 mg/mL, or about 1200 mg/mL to about 1350 mg/mL after removing the aqueous first liquid and organic second liquid from the mixture. In certain other embodiments, the particles have a skeletal density of greater than about 1000 mg/mL, about 1050 mg/mL, about 1100 mg/mL, about 1150 mg/mL, about 1200 mg/mL, about 1250 mg/mL, about 1300 mg/mL, about 1310 mg/mL, about 1320 mg/mL, about 1330 mg/mL, about 1340 mg/mL, about 1350 mg/mL, about 1360 mg/mL, about 1370 mg/mL, about 1380 mg/mL, about 1390 mg/mL, about 1400 mg/mL, about 1410 mg/mL, about 1420 mg/mL, about 1430 mg/mL, about 1440 mg/mL, about 1450 mg/mL, about 1460 mg/mL, about 1470 mg/mL, about 1480 mg/mL, about 1490 mg/mL, or about 1500 mg/mL after removing the aqueous first liquid and organic second liquid from the mixture.

In some embodiments, the particles can be characterized by a glass transition temperature of about 0° C. to about 250° C. after removing the aqueous first liquid and organic second liquid from the mixture, e.g., of about 34° C. to about 200° C., of about 60° C. to about 170° C., of about 90° C. to about 170° C., of about 100 to about 170° C., of about 130 to about 170° C., of about 150 to about 170° C., or of about 160 to about 170° C. after removing the aqueous first liquid and organic second liquid from the mixture. The term "glass transition" as used herein, refers to a thermodynamic transition of an amorphous material characterized by step changes in specific heat capacity and modulus. In preferred embodiments, the particles that are produced by the methods described herein are amorphous. At temperatures above the glass transition temperature, molecular mobility is increased as are the rates of physical and chemical changes. Exemplary analytical methods for the determination of the glass transition temperature include differential scanning calorimetry and dynamic mobility analysis. In other embodiments, the particle has a glass transition temperature of about 60 to about 170° C. after removing the aqueous first liquid and organic second liquid from the mixture. In still other embodiments, the particle has a glass transition temperature of about 60 to about 100° C. after removing the aqueous first liquid and organic second liquid from the mixture. In certain embodiments, the particle has a glass transition temperature of about 75 to about 80° C. after removing the aqueous first liquid and organic second liquid from the mixture. In some embodiments, the particle has a glass transition temperature of about 60 to about 120° C. after removing the aqueous first liquid and organic second liquid from the mixture.

In certain embodiments, the particle has a glass transition temperature that is higher than about 50° C. after removing the aqueous first liquid and organic second liquid from the mixture. In certain other embodiments, the particle has a glass transition temperature that is higher than about 90° C. after removing the aqueous first liquid and organic second liquid from the mixture. In still other embodiments, the particle has a glass transition temperature that is higher than about 100° C. after removing the aqueous first liquid and organic second liquid from the mixture. In certain preferred embodiments, the particle has a glass transition temperature that is higher than about 160° C. after removing the aqueous first liquid and organic second liquid from the mixture. In preferred embodiments, the particle has a glass transition temperature that is higher than about 170° C. after removing the aqueous first liquid and organic second liquid from the mixture. In some embodiments, the particles have a glass transition temperature of about 60 to about 100° C. after removing the aqueous first liquid and organic second liquid from the mixture. In other embodiments, the particles have a glass transition temperature of about 75 to about 80° C. after removing the aqueous first liquid and organic second liquid from the mixture.

In some embodiments, the particles further comprise a carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, a surfactant, or a combination thereof.

In other embodiments, the carbohydrate may be from the families of monosaccharides, disaccharides, oligosaccharides, or polysaccharides. In some embodiments, the carbohydrate is dextran, trehalose, sucrose, agarose, mannitol, lactose, sorbitol, maltose, starch, alginates, xanthan, galactomanin, agar, agarose, or a combination thereof. In certain embodiments, the carbohydrate is dextran, trehalose, sucrose, agarose, mannitol, lactose, sorbitol, maltose, hydroxypropyl beta-cyclodextrin, sulfobutylether beta-cyclodextrin, or a combination thereof. In preferred embodiments, the carbohydrate is trehalose, cyclodextrins, hydroxypropyl beta-cyclodextrin, sulfobutylether beta-cyclodextrin, sucrose, or a combination thereof. In certain preferred embodiments, the carbohydrate is trehalose. Cyclodextrins are available in three different forms α, β, and γ based on the number of number of glucose monomers. The number of glucose monomers in α, β, and γ cyclodextrin can be 6, 7, or 8, respectively.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is citrate, histidine, phosphate, succinate, or a combination thereof. In certain other embodiments, the pH is about 4.5 to about 7.5. In preferred embodiments, the pH is about 5.5 to about 6.5.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, magnesium chloride, potassium nitrate, or a combination thereof. In preferred embodiments, the salt is sodium chloride.

In some embodiments, the chelator is disodium edetate, ethylenediaminetetraacetic acid, pentetic acid, or a combination thereof. In other embodiments, the mineral is calcium, zinc, titanium dioxide, or a combination thereof. In certain embodiments, the polymer is propyleneglycol, glucose star polymer, silicone polymer, polydimethylsiloxane, polyethylene glycol, carboxymethylcellulose, poly(glycolic acid), poly(lactic-co-glycolic acid), polylactic acid, polycaprolactone (PCL), polyvinylpyrrolidone (PVP), ficoll, dextran, or a combination thereof.

In other embodiments, the protein stabilizer is acetyltryptophanate, caprylate, N-acetyltryptophan, trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, or a combination thereof. In certain embodiments, the protein stabilizer is trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, cyclodextrin, hydroxypropyl beta-cyclodextrin, sulfobutylether beta-cyclodextrin, pentetic acid, or a combination thereof. In preferred embodiments, the protein stabilizer is trehalose, cyclodextrin, hydroxypropyl beta-cyclodextrin, sulfobutylether beta-cyclodextrin, pentetic acid, or a combination thereof. In certain preferred embodiments, the PEG is PEG 200, PEG 300, PEG 3350, PEG 8000, PEG 10000, PEG 20000, or a combination thereof. The stabilizers, used synonymously with the term "stabilizing agent", as described herein, can be a salt, a carbohydrate, saccharides or amino acids, preferably a carbohydrate or saccharide admitted by the authorities as a suitable additive or excipient in pharmaceutical compositions. The term "stabilizer" refers to an excipient or a mixture of excipients which stabilizes the physical and/or chemical properties of a therapeutic biologic, e.g., an antibody. In some embodiments, stabilizers prevent, e.g., degradation of the therapeutic biologic during droplet formation, desiccation, and/or storage of the particulate matter. Exemplary stabilizers include, but are not limited to, sugars, salts, hydrophobic salts, detergents, reducing agents, cyclodextrins, polyols, carboxylic acids, and amino acids. A "stable" formulation as described herein, refers to a formulation in which the therapeutic biologic retains an acceptable portion of its essential physical, chemical, or biological properties over an acceptable period of time. In the case of proteins, e.g., exemplary methods of assessing stability are reviewed in (i) Peptide and Protein Drug Delivery, 247-301, Vincent Lee Ed., Marcel Dekker, Inc., New York, NY, 1991, and (ii) Jones, A., Adv. Drug Delivery Rev. 10: 29-90 (1993). In certain embodiments, chemical stability of a protein is assessed by measuring the size distribution of the sample at several stages. These include, e.g., before particle formation (assessment of the feed solution), immediately after particle formation, and again after a period of storage, where storage takes place either within or in the absence of a suspension formulation carrier medium. In certain other embodiments, the size distribution is assessed by size exclusion chromatography (SEC-HPLC). The term "excipient" refers to an additive to a preparation or formulation, which may be useful in achieving a desired modification to the characteristics of the preparation or formulation. Such modifications include, but are not limited to, physical stability, chemical stability, and therapeutic efficacy. Exemplary excipients include, but are not limited to a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, and/or nutrient media.

Examples of emulsifiers suitable for use in the particles include, but are not limited to, lipophilic agents having an HLB of less than 15, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan ester including sorbitan monostearate, sorbitan sesquioleate; fatty acids and their soaps including stearic acid, palmitic acid, and oleic acid; phospholipids; or a combination thereof. In some embodiments, the emulsifier is polysorbate 80, polysorbate 60, polysorbate 20, e.g., Tween 80, Tween 60, Tween 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the fatty acid ester of sorbitol is a sorbitan ester, e.g., span 20, span 40, span 60, or span 80. In certain preferred embodiments, the emulsifier is polysorbate 80, sorbitan monooleate, or a combination thereof. In other embodiments, the antiseptic is phenol, m-cresol, benzyl alcohol, 2-phenyloxyethanol, chlorobutanol, neomycin, benzethonium chloride, gluteraldehyde, beta-propiolactone, or a combination thereof.

In certain embodiments, the amino acid is alanine, aspartic acid, cysteine, isoleucine, glutamic acid, leucine, phenylalanine, pyrrolysine, serine, selenocysteine, threonine, tryptophan, tyrosine, valine, asparagine, arginine, histidine, glycine, glutamine, proline, methionine, or various salts thereof (arginine hydrochloride, arginine glutamate, and the like) or a combination thereof. In certain other embodiments, the amino acid is alanine, aspartic acid, cysteine, isoleucine, glutamic acid, leucine, phenylalanine, pyrrolysine, serine, selenocysteine, threonine, tryptophan, tyrosine, valine, asparagine, arginine, histidine, glycine, glutamine, proline, methionine, or a combination thereof. In certain preferred embodiments, the amino acid is arginine, histidine, proline, asparagine, or a combination thereof. In preferred embodiments, the amino acid is histidine.

In some embodiments, the antioxidant is glutathione, ascorbic acid, cysteine, N-acetyl-L-tryptophanate, tocopherol, histidine, methionine, or a combination thereof. In certain preferred embodiments, the antioxidant is methionine. In other embodiments, the protein is protamine, protamine sulfate, gelatin, or a combination thereof. In certain embodiments, the organic solvent is dimethyl sulfoxide, N-methyl-2-pyrrolidone, or a combination thereof. The paraben can be a parahydroxybenzoate. In still other embodiments, the bactericide is benzalkonium chloride (cationic surfactants), hypochlorites, peroxides, alcohols, phenolic compounds (e.g. carbolic acid), benzyl benzoate, or a combination thereof. In preferred embodiments, the bactericide is benzyl benzoate.

In other embodiments, the fungicide is acibenzolar, 2-phenylphenol, anilazine, carvone, natamycin, potassium azide, or a combination thereof. In preferred embodiments, the fungicide is benzyl benzoate. In certain embodiments, the vitamin is thiamine, riboflavin, niacin, pantothenic acid, biotin, vitamin $B_6$, vitamin $B_{12}$, folate, niacin, ascorbic acid, calciferols, retinols, quinones, or a combination thereof. In still other embodiments, the preservative is sodium nitrate, sulfur dioxide, potassium sorbate, sodium sorbate, sodium benzoate, benzoic acid, methyl hydroxybenzoate, thimerosal, parabens, formaldehyde, castor oil, or a combination thereof. In preferred embodiments, the preservative is methyl hydroxybenzoate, thimerosal, a paraben, formaldehyde, castor oil, or a combination thereof.

A number of nutrient media, preferably serum free, alone or in combination, may be used in the present disclosure, including commercially available media or other media well known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME—with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E—with Earle's salt base), Medium M199 (M199H—with Hank's salt base), Minimum Essential Medium Eagle (MEM-E- with Earle's salt base), Minimum Essential Medium Eagle (MEM-H—with Hank's salt base) and Minimum Essential Medium Eagle (MEM-NAA- with non-essential amino acids), among numerous others. In addition, serum-containing nutrient media may also be used in compositions according to the present disclosure, but the use of serum-containing media is less preferred because of the possibility that the serum may be contaminated with microbial agents and because the patient may develop immunological reactions to certain antigenic components contained in the serum.

In some embodiments, the oligopeptide is trileucine. In other embodiments, the biologic excipient are nucleic acids, oligonucleotides, antibodies or fragment thereof, amino acids, polyamino acids, peptides, proteins, cells, bacteria, gene therapeutics, genome engineering therapeutics, epigenome engineering therapeutics, hormones, nucleoproteins, glycoproteins, lipoproteins, exosomes, outer membrane vesicles, vaccines, viruses, bacteriophages, organelles, nutrient media, or a combination thereof. In certain embodiments, the chemical excipient are chemical drugs, contrast agents, dyes, magnetic particles, polymer beads, metal nanoparticles, metal microparticles, quantum dots, antioxidants, antibiotic agents, steroids, analgesics, local anesthetics, anti-inflammatory agents, parabens, anti-microbial agents, chemotherapeutic agents, vitamins, minerals, bactericides, antiseptics, or a combination thereof.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, sodium laureth sulfate, lecithin, or a combination thereof. In some embodiments, the surfactant includes, but is not limited to: (i) cationic surfactants such as; cetyltrimethylammonium chloride, hexadecyltrimethylammonium chloride, benzalkonium chloride, benzethonium chloride, dioctadecyldimethylammonium bromide; (ii) anionic surfactants such as magnesium stearate, sodium dodecyl sulfate, dioctyl sodium sulfosuccinate, sodium myreth sulfate, perfluorooctanesulfonate, alkyl ether phosphates; (iii) non-ionic surfactants such as alkylphenol ethoxylates (TritonX-100), fatty alcohol ethoxylates (octaethylene glycol monododecyl ether, cocamide diethanolamine, poloxamers, glycerolmonostearate, fatty acid esters of sorbitol (sorbitan monolaurate, Tween 80, Tween 20; and (iv) zwitterionic surfactants such as cocamidopropyl hydroxysultaine, and 3-[(3-Cholamidopropyl)dimethylammonio]-1-propanesulfonate (CHAPS). In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, phosphatidylcholine, polyglycerol polyricinoleate, siloxanes, cetyl polyethylene glycol/polypropylene glycol-10/1 dimethicone triglyceride, bis-polyethylene glycol/polypropylene glycol-14/14 dimethicone, bis-(glyceryl/lauryl) glyceryl lauryl dimethicone and caprylic/capric triglyceride, cetyl polyethylene glycol/polypropylene glycol-10/1 dimethicone, phospholipids, or a combination thereof. In certain embodiments, the surfactant is polysorbate, docusate, lecithin, sorbitan ester, or a combination thereof. In certain other embodiments, the surfactant is polysorbate 20, polysorbate 60, or polysorbate 80, e.g., Tween 20, Tween 60, Tween 80. In still other embodiments, the surfactant is polysorbate 20 or polysorbate 80. In certain preferred embodiments, the fatty acid ester of sorbitol is a sorbitan ester, e.g., span 20, span 40, span 60, or span 80. In other preferred embodiments, the surfactant is an ionic surfactant. In preferred embodiments, the surfactant is polysorbate 80.

In some embodiments, the particles have greater than about 60% therapeutic biologic by weight after removing the aqueous first liquid and organic second liquid from the mixture, e.g., greater than about 65, 70, 75, 80, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% therapeutic biologic by weight after removing the aqueous first liquid and organic second liquid from the mixture. In certain other embodiments, the particles have greater than about 80% therapeutic biologic by weight after removing the aqueous first liquid and organic second liquid from the mixture. In other embodiments, the particles have greater than about 90% therapeutic biologic by weight after removing the aqueous first liquid and organic second liquid from the mixture. In certain embodiments, the particles have greater than about 95% therapeutic biologic by weight after removing the aqueous first liquid and organic second liquid from the mixture. In still other embodiments, the particles have greater than about 98% therapeutic biologic by weight after removing the aqueous first liquid and organic second liquid from the mixture. In certain preferred embodiments, the particles have greater than about 99% therapeutic biologic by weight after removing the aqueous first liquid and organic second liquid from the mixture.

In certain embodiments, the particles include a loading of therapeutic biologic from about 1 to about 100 wt % after removing the aqueous first liquid and organic second liquid from the mixture, e.g., from about 50 to about 100 wt %, from about 75 to about 100 wt %, from about 90 to about 100 wt %, from about 95 to about 100 wt %, from about 99 to about 100 wt %, or from about 99.9 to about 100 wt % after removing the aqueous first liquid and organic second liquid from the mixture. At these loadings the therapeutic biologic retains from about 0.5 to about 1.0 activity during particle formation, e.g., from about 0.75 to about 1.0 activity, from about 0.9 to about 1.0 activity, from about 0.95 to about 1.0 activity, from about 0.99 to about 1.0 activity, or from about 0.999 to about 1.0 activity. This includes the activity retained through primary desiccation and, in some cases, secondary desiccation post processing.

In other embodiments, the particles have less than 10% aggregation or less than 10% fragmentation of the therapeutic biologic after removing the aqueous first liquid and organic second liquid from the mixture, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% of the therapeutic biologic after removing the aqueous first liquid and organic second liquid from the mixture. In certain embodiments, the particles have about 3% to about 1% aggregation of the therapeutic biologic after removing the aqueous first liquid and organic second liquid from the mixture. In certain other embodiments, the particles have about 1% to about 0.5% aggregation of the therapeutic biologic after removing the aqueous first liquid and organic second liquid from the mixture. In preferred embodiments, the particles are substantially free from any aggregation of the therapeutic biologic after removing the aqueous first liquid and organic second liquid from the mixture. In still other embodiments, the particles have less than about 3%, about 1%, or about 0.5% fragmentation of the therapeutic biologic after removing the aqueous first liquid and organic second liquid from the mixture. In certain preferred embodiments, the particles are substantially free from any fragmentation of the therapeutic biologic after removing the aqueous first liquid and organic second liquid from the mixture. Suitable methods for measuring aggregation and fragmentation of a biologic can be accomplished by using size-exclusion chromatography (SEC).

In some embodiments, the process of particle formation provides less than a 50% change in charge variants in the population of a therapeutic biologic after removing the aqueous first liquid and organic second liquid from the mixture, e.g., an antibody, (e.g., less than 40, 30, 25, 20, 15, 10, 8, 5, 4, 3, 1, or 0.5% after removing the aqueous first liquid and organic second liquid from the mixture) as compared to the therapeutic biologic prior to particle formation. Charge variants may be acidic, basic, or neutral, and the variation may be caused post-translation modifications at terminal amino acids, such as asparagine deamidation or lysine glycation. For example, charge variants include the loss of a positive charge by the loss of a C-terminal lysine residue, covalent bonding of the amine portions of two lysine residues by reducing sugars, or the conversion of an N-terminal amine to a neutral amide by the cyclization of N-terminal glutamines. Negative charges on proteins, e.g., antibodies, can appear by the conversion of asparagine residues to aspartic acid and/or isoaspartic residues via a deamidation reaction. Exemplary methods of measuring charge variants include cation exchange chromatography (CIEX), where the variants are quantified by dividing the area under the peak corresponding to the variant, e.g., acidic, basic, or neutral population by the cumulative area contained beneath all peaks in the sample spectrum. Changes in charge variant population percentage between two samples, e.g., Sample A and Sample B, are computed as the numerical difference in the respective population variant percentages, i.e., by subtracting the specific variant, e.g., acidic, percentage of Sample B from the specific variant, e.g., acidic, percentage of Sample A, or vice versa. In certain embodiments, the analysis may be extended similarly for all variants within a population.

In certain embodiments, the particles have less than about 50% change in charge variants of the therapeutic biologic after removing the aqueous first liquid and organic second liquid from the mixture, e.g., less than about 45, 40, 35, 30, 25, 20, 15, 10, 9, 8, 7, 6, 5, 4, 3, 2, 1, 0.5, 0.1% after removing the aqueous first liquid and organic second liquid from the mixture, compared to the starting biologic prior to particle formation. In preferred embodiments, the particles are substantially free from any change in charge variants of the therapeutic biologic after removing the aqueous first liquid and organic second liquid from the mixture, compared to the starting biologic prior to particle formation. Suitable methods for measuring a change in charge variants of a biologic can be accomplished by using cation exchange chromatography (CIEX).

In some embodiments, the particles have a surfactant content of less than about 10% by mass after removing the aqueous first liquid and organic second liquid from the mixture, e.g., less than about 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001% by mass after removing the aqueous first liquid and organic second liquid from the mixture. In other embodiments, the particles have a surfactant content of less than about 5% by mass after removing the aqueous first liquid and organic second liquid from the mixture. In certain embodiments, the particles have a surfactant content of less than about 3% by mass after removing the aqueous first liquid and organic second liquid from the mixture. In still other embodiments, the particles have a surfactant content of less than about 1% by mass after removing the aqueous first liquid and organic second liquid from the mixture. In certain other embodiments, the particles have a surfactant content of less than about 0.1% by mass after removing the aqueous first liquid and organic second liquid from the mixture. In some embodiments, the particles have a surfactant content of less than about 0.01% by mass after removing the aqueous first liquid and organic second liquid from the mixture. In other embodiments, the particles have a surfactant content of less than about 0.001% by mass after removing the aqueous first liquid and organic second liquid from the mixture. In preferred embodiments, the particles are substantially free from any surfactant content after removing the aqueous first liquid and organic second liquid from the mixture.

In other embodiments, the surfactant content of the particles is from 0 to 10 wt % after removing the aqueous first liquid and organic second liquid from the mixture, e.g., from 0 to 5 wt %, from 0 to 3 wt %, from 0 to 2 wt %, from 0 to 1 wt %, from 0 to 0.5 wt %, from 0 to 0.2 wt %, from 0 to 0.1 wt %, from 0 to 0.01 wt %, or from 0 to 0.001 wt % after removing the aqueous first liquid and organic second liquid from the mixture. Exemplary methods of measuring the surfactant content include reconstitution of the particles in an appropriate medium, e.g., deionized water, and subsequent analysis of the reconstituted solution through liquid chromatography. The chromatographic technique may include the use of a charged aerosol detector (CAD) or an evaporative light scattering detector (ELSD).

In some embodiments, the aqueous first liquid content remaining in the particles are less than about 10% by mass after removing the aqueous first liquid, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by mass remaining after removing the aqueous first liquid and organic second liquid from the mixture. In other embodiments, the particles have less than about 5% of residual aqueous first liquid by mass remaining after removing the aqueous first liquid and organic second liquid from the mixture. In still other embodiments, the particles have less than about 3% of residual aqueous first liquid by mass remaining after removing the aqueous first liquid and organic second liquid from the mixture. In certain embodiments, the particles have less than about 1% of residual aqueous first liquid by mass remaining after removing the aqueous first liquid and organic second liquid from the mixture. In preferred embodiments, the particles are substantially free from any residual aqueous first liquid by mass after removing the aqueous first liquid and organic second liquid from the mixture.

In other embodiments, the particles have about 1% to about 7% of residual aqueous first liquid by mass remaining after removing the aqueous first liquid and organic second liquid from the mixture. In still other embodiments, the particles have about 1% to about 5% of residual aqueous first liquid by mass remaining after removing the aqueous first liquid and organic second liquid from the mixture. In certain embodiments, the particles have about 1% to about 3% of residual aqueous first liquid by mass remaining after removing the aqueous first liquid and organic second liquid from the mixture. In preferred embodiments, the particles are substantially free from any residual aqueous first liquid by mass after removing the aqueous first liquid and organic second liquid from the mixture. Exemplary methods for the measurement of residual aqueous first liquid and/or organic second liquid content include chemical titration methods, e.g., Karl Fischer titration involving an oven. A variety of solvents, including water, may also be measured using weight loss methods involving thermal excitation. Exemplary methods include Thermogravimetric Analysis with Infrared Spectroscopy (TGA-IR) or Gas Chromatography Flame Ionization Detector Mass Spectrometry (GC-FID/MS).

As used herein, the terms "moisture content" and "water content" are used interchangeably. In some embodiments, the moisture, e.g., water, content of the particle is less than about 10% by mass after removing the aqueous first liquid and organic second liquid from the mixture, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by mass after removing the aqueous first liquid and organic second liquid from the mixture. In other embodiments, the particle has less than about 5% residual moisture by mass after removing the aqueous first liquid and organic second liquid from the mixture. In still other embodiments, the particle has less than about 3% residual moisture by mass after removing the aqueous first liquid and organic second liquid from the mixture. In certain embodiments, the particle has less than about 2% residual moisture by mass after removing the aqueous first liquid and organic second liquid from the mixture. In preferred embodiments, the particle has less than about 1% residual moisture by mass after removing the aqueous first liquid and organic second liquid from the mixture. In certain preferred embodiments, the particles are substantially free from any residual moisture by mass after removing the aqueous first liquid and organic second liquid from the mixture. In some embodiments, the particles have less than about 0.1% of residual moisture by mass after removing the aqueous first liquid and organic second liquid from the mixture. In some embodiments, the particles have less than about 0.01% of residual moisture by mass after removing the aqueous first liquid and organic second liquid from the mixture. Exemplary methods for the measurement of moisture content include chemical titration methods, e.g., Karl Fischer titration involving an oven. A variety of solvents, including water, may also be measured using weight loss methods involving thermal excitation. Exemplary methods include Thermogravimetric Analysis with Infrared Spectroscopy (TGA-IR) or Gas Chromatography Flame Ionization Detector Mass Spectrometry (GC-FID/MS).

In some embodiments, the organic second liquid content remaining in the particles is less than about 10% by mass after removing the aqueous first liquid, e.g., less than about 9, 8, 7, 6, 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1% by mass remaining after removing the aqueous first liquid and organic second liquid from the mixture. In other embodiments, the particles have less than about 5% of residual organic second liquid by mass remaining after removing the aqueous first liquid and organic second liquid from the mixture. In still other embodiments, the particles have less than about 3% of residual organic second liquid by mass remaining after removing the aqueous first liquid and organic second liquid from the mixture. In certain embodiments, the particles have less than about 1% of residual organic second liquid by mass remaining after removing the aqueous first liquid and organic second liquid from the mixture. In preferred embodiments, the particles are substantially free from any residual organic second liquid by mass after removing the aqueous first liquid and organic second liquid from the mixture.

In other embodiments, the particle has about 1% to about 7% residual moisture by mass after removing the aqueous first liquid and organic second liquid from the mixture. In still some embodiments, the particle has about 1% to about 5% residual moisture by mass after removing the aqueous first liquid and organic second liquid from the mixture. In certain embodiments, the particle has about 1% to about 3% residual moisture by mass after removing the aqueous first liquid and organic second liquid from the mixture. In preferred embodiments, the particle is substantially free from any residual moisture by mass after removing the aqueous first liquid and organic second liquid from the mixture. In other embodiments, the particles are stable for at least one month. In some embodiments, the particles are stable for at least two months. In certain embodiments, the particles are stable for at least three months. In certain other embodiments, the particles are stable for at least three months at 40° C.

As used herein, the term "dispersity index" (DI) is a parameter characterizing the degree of non-uniformity of a size distribution of particles. The polydispersity index (PDI), "population dispersity" or "span", e.g., D10, D50, D90, is a value that can indicate the breadth of the particle size distribution. Particle size distribution are reported by D10, D50, D90, and the mean particle size in µm, with the values representing the percentage of particles that are smaller than the indicated D-number, e.g. the D10 particle size is the particle diameter at which 10% of the mass is composed of particles with a diameter less than this value, the D50 particle size is the particle diameter at which 50% of the mass is composed of particles with a diameter less than this value and the D90 particle size is the particle diameter at which 90% of the mass is composed of particles with a diameter less than this value. The D10, D50, and D90 particle size distribution can be measured using a laser light scattering particle sizer.

In other embodiments described herein, the particles have a polydispersity index from about 0.002 to about 1.000, e.g., from about 0.003, 0.004, 0.005, 0.006, 0.007, 0.008, 0.009, 0.010, 0.020, 0.030, 0.040, 0.050, 0.060, 0.070, 0.080, 0.090, 0.100, 0.200, 0.300, 0.400, 0.500, 0.600, 0.700, 0.800, 0.900 to about 1.000. In certain embodiments, the particles have a polydispersity index from about 0.002 to about 0.900. In certain preferred embodiments, the particles have a polydispersity index from about 0.100 to about 0.300.

In certain embodiments, the particles may include one or more therapeutic biologics. In other embodiments, the particles can have diameters from about 0.1 to about 1000 µm after removing the aqueous first liquid and organic second liquid from the mixture, e.g., about 0.1 to about 90 µm, about 90 to about 230 µm, or about 0.1 to about 1 µm after removing the aqueous first liquid and organic second liquid from the mixture. In still other embodiments, the particles can have a size dispersity from about 0 to about 0.9 after removing the aqueous first liquid and organic second liquid from the mixture, e.g., from about 0 to about 0.7, from about 0 to about 0.5, or from about 0 to about 0.2 after removing the aqueous first liquid and organic second liquid from the mixture. Methods of measuring the particle size and distribution include imaging flow cytometry, laser diffraction, and image analysis of scanning electron micrographs of the particles in which an average spherical radius or diameter can be calculated on the basis of the cross-sectional areas of the particles projected onto the plane of the image. In certain other embodiments of the disclosure, the particle may have a diameter of about 0.1 to about 1000 µm, and a glass transition temperature of about 0 to about 250° C., after removing the aqueous first liquid and organic second liquid from the mixture.

The particles comprising at least one therapeutic biologic described herein, can be prepared in a number of ways, as well as any methods of forming the particles disclosed in, for example, in International Appliction Nos. PCT/US2017/063150 (Pub. No. WO 2018/098376), PCT/US2018/043774 (Pub. No. WO 2019/023392), PCT/US2019/033875 (Pub. No. WO 2019/226969), PCT/US2020/15957 (Pub. No. WO 2020/160323), PCT/US2020/050508 (Pub. No. WO 2021/050953), PCT/US2021/16878, and PCT/US2021/018806, the contents of each of which are hereby incorporated by reference in their entireties.

While each of the elements of the present disclosure is described herein, as containing multiple embodiments, it should be understood that, unless indicated otherwise, each of the embodiments of a given element of the present disclosure is capable of being used with each of the embodiments of the other elements of the present disclosure and each such use is intended to form a distinct embodiment of the present disclosure.

It will be understood by one of ordinary skill in the relevant arts that other suitable modifications and adaptations to the compositions and methods described herein are readily apparent from the description of the disclosure contained herein, in view of information known to the ordinarily skilled artisan and may be made without departing from the scope of the disclosure or any embodiment thereof.

Pharmaceutical Compositions

In certain embodiments according to the disclosure as described herein, a composition comprising a plurality of particles can have improved stability of the therapeutic biologic compared to an aqueous composition comprising the therapeutic biologic in monomeric form.

In other embodiments, the disclosure provides a composition containing a plurality of particles that include a therapeutic biologic, e.g., an antibody, antibody fragment, bovine serum albumin (BSA), or human serum albumin (HSA), where the storage stability of the therapeutic biologic in the particles is improved with respect to the storage stability of the therapeutic biologic in the feed solution. In some embodiments, storage conditions are defined by time (e.g., more than about 2 years, more than about 1 year, more than about 6 months, more than about 3 months, more than about 1 month, or more than about 1 week) and temperature (e.g., about −80° C. to about 100° C., about −80° C. to about 60° C., about −20° C. to about 60° C., about 4 to about 60° C.), among potentially other variables. In still other embodiments, the storage time is about 3 days, about 7 days, about 30 days, about 90 days, about 180 days, about 1 year, or about 2 years. In certain embodiments, this temperature is about −80° C., about −40° C., about −20° C., about 4° C., about 25° C., about 40° C., or about 40 to about 60° C.

The phrase "pharmaceutically acceptable" is employed herein, to refer to those therapeutic biologics, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically acceptable" can refer to particles and compositions comprising a plurality of particles that do not produce an adverse, allergic, or other untoward reaction when administered to a mammal, such as a human, as appropriate. The preparation of a pharmaceutical composition comprising an antibody or additional active ingredient will be known to those of skill in the art in light of the present disclosure. Moreover, for mammal (e.g., human) administration, it will be understood that preparations should meet sterility, pyrogenicity, general safety, and purity standards as required by FDA Office of Biological Standards.

The phrase "pharmaceutically acceptable liquid" includes any and all aqueous solvents (e.g., water, alcoholic/aqueous solutions, saline solutions, parenteral vehicles, such as sodium chloride, Ringer's dextrose, and the like), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. In certain preferred embodiments, the plurality of particles is suspended in a pharmaceutically acceptable liquid. In preferred embodiments, the liquid is a pharmaceutically acceptable liquid.

A pharmaceutical composition (formulation) as described herein, can be administered to a subject by any of a number of routes of administration including, for example, parenterally (including intramuscularly, intravenously, subcutaneously or intrathecally as, for example, a sterile solution or suspension); intraperitoneally; or subcutaneously. In certain embodiments, a composition may be simply suspended in a non-aqueous liquid carrier. Details of appropriate routes of administration and compositions suitable for same can be found in, for example, U.S. Pat. Nos. 6,110,973; 5,763,493; 5,731,000; 5,541,231; 5,427,798; 5,358,970 and 4,172,896, as well as in patents cited therein. The term "suspension formulation" refers to a liquid formulation including solid particles disposed within a carrier liquid in which they are not soluble on an appropriate timescale. The particles may settle over time, i.e., the physical stability of the suspension is not indefinite, but may be re-suspended using a form of agitation or excitation.

A "therapeutic amount" refers to an amount of a therapeutic biologic required to produce the desired effect. As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

In some embodiments, insoluble particulate matter with characteristic sizes greater than or equal to about 100 μm that persist upon dissolution in an aqueous liquid are referred to as Visible Particles (VP). In preferred embodiments of the disclosure described herein, the composition is substantially free of Visible Particles (VP). In certain preferred embodiments, the aqueous liquid is water, aqueous buffer or a physiologically relevant aqueous liquid. In other embodiments, insoluble particulate matter which is visible to the naked eye under prescribed lighting conditions persist upon reconstitution of the particles of the disclosure into a liquid pharmaceutical composition. Insoluble particulates of this type, is sometimes referred to as Visible Particles (VPs), and are typically greater than about 100 μm in size. VPs are present in quantities from about 0 to about 1 per about 1 mL, e.g., from about 0 to about 0.01 per about 1 mL, from about 0 to about 0.001 per about 1 mL, or about 0 to about 0.0001 per about 1 mL. Exemplary methods of measuring VPs include analysis of the therapeutic biologic by visual inspection against and black and white background for 5 seconds under illumination of about 2000 and about 3750 lux in accordance with USP <790> after reconstitution and dilution of the therapeutic biologic to a standard concentration, e.g., about 100 mg/mL or about 1 mg/mL. In some embodiments, fewer than 65 samples in 10,000 (0.65%) are rejected on the basis of USP <790>. Alternate inspection strategies light-obscuration, automated optical imaging systems, or X-ray imaging in accordance with USP <1790>.

In other embodiments, insoluble particulate matter with characteristic sizes from about 1 μm to about 100 μm that persist upon dissolution in an aqueous liquid are referred to as Subvisible Particles (SvPs). SvPs are present in quantities from about 0 to 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In other embodiments, the count of particles with characteristic size greater than or equal to 10 μm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per about 1 mL, from about 0 to about 3 per about 1 mL, or from about 0 to about 1 per about 1 mL. In certain embodiments, the count of particles with characteristic size greater than or equal to 25 μm is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. Exemplary methods of measuring SvPs include analysis of the therapeutic biologic with a Coulter Counter, HIAC Royco, or micro-flow imaging system after reconstitution and dilution of the therapeutic biologic to a standard concentration, e.g., about 100 mg/mL or about 1 mg/mL. In still other embodiments, the composition has a concentration of insoluble subvisible particles of about 0 per about 1 mL to about 100,000,000 per about 1 mL of greater than about 10 μm particles upon dissolution in an aqueous liquid. In certain embodiments, the composition has a concentration of insoluble subvisible particles of about 0 per about 1 mL to about 6000 per about 1 mL of greater than about 10 μm particles upon dissolution in an aqueous liquid. In preferred embodiments, the composition has a concentration of insoluble subvisible particles of about 0 per about 1 mL to about 600 per about 1 mL of greater than about 25 μm particles upon dissolution in an aqueous liquid. In certain preferred embodiments, the composition is substantially free of insoluble subvisible particles upon dissolution in an aqueous liquid. In preferred embodiments, the aqueous liquid is water, aqueous buffer or a physiologically relevant aqueous liquid.

In some embodiments, insoluble particulate matter with characteristic sizes from about 100 nm to about 1 μm that persist upon dissolution in an aqueous liquid are referred to as submicron particles (SMP) and sometimes known as nanoparticles. Quantitatively, SMPs are present in quantities from about 0 to $5 \times 10^{12}$ per about 1 mL, e.g., from about 0 to about $0.5 \times 10^{12}$ per about 1 mL, from about 0 to about $50 \times 10^9$ per about 1 mL, from about 0 to about $10 \times 10^9$ per about 1 mL, from about 0 to about $5 \times 10^9$ per about 1 mL, from about 0 to about $0.5 \times 10^9$ per about 1 mL, from about 0 to about $50 \times 10^6$ per about 1 mL, from about 0 to about $1 \times 10^6$ per about 1 mL, from about 0 to about 500,000 per about 1 mL, from about 0 to about 200,000 per about 1 mL, from about 0 to about 100,000 per about 1 mL, from about 0 to about 10,000 per about 1 mL, from about 0 to about 5000 per about 1 mL, or from about 0 to about 1000 per about 1 mL. Exemplary methods of measuring SMPs quantitatively include analysis of the therapeutic biologic with a NanoSight, asymmetric field flow fractionation coupled to a multi-angle laser light scattering (AF4 MALS), Dynamic Light Scattering (DLS), or any other nano-particle tracking device known in the art, after reconstitution and dilution of the therapeutic biologic to a standard concentration, e.g., about 100 mg/mL, about 1 mg/mL, or about 1 μg/mL. Qualitatively, SMPs are within a range comparable to the starting monomeric therapeutic biologic solution. In preferred embodiments, the composition is substantially free of submicron particles (SMP) upon dissolution in an aqueous liquid. In certain preferred embodiments, the aqueous liquid is water, aqueous buffer or a physiologically relevant aqueous liquid. Qualitatively, as described herein, SMPs are within a range comparable to the feed solution.

In certain embodiments, the pharmaceutical composition (formulation) includes insoluble particulate matter smaller than or equal to 1 m. The pharmaceutical composition can have a concentration of insoluble particles with a characteristic size greater than or equal to about 100 nm is about 1 to $5 \times 10^{12}$ per about 1 mL in suspension, or have a concentration of insoluble particles with a characteristic size less than or equal to about 1 μm is about 1 to $5 \times 10^{12}$ per about 1 mL in suspension. In still other embodiments, the pharmaceutical composition of particles may include insoluble particulate matter larger than or equal to about 1 μm in size. In certain other embodiments, the number of insoluble particles is from about 0 to about 100,000,000 per about 1 mL, e.g., less than about 10,000,000, 1,000,000, 100,000, 10,000, 1000, 100, 10, or about 1 per about 1 mL. For example, the number of insoluble particles greater than about 10 μm is from about 0 to about 6,000 per about 1 mL, e.g., less than about 5,000, about 4,000, about 3,000, about 2,000, about 1,000, about 500, about 100, about 10, or about 1 per about 1 mL, and/or the number of insoluble particles greater than about 25 μm is from about 0 to about 600 per about 1 mL, e.g., less than about 500, about 400, about 300, about 200, about 100, about 50, about 10, or about 1 about 1 per about 1 mL.

In some embodiments, the disclosure provides a pharmaceutical composition, e.g., a suspension or dried form, containing a plurality of particles that include a therapeutic biologic, e.g., an antibody. The composition preferably has a concentration of insoluble particles, e.g., SvPs, of about 0 and about 100,000,000 per about 1 mL in suspension or upon reconstitution. In other embodiments, the concentration of insoluble particles is of about 0 and about 1,000,000 per about 1 mL in suspension or upon reconstitution. In still other embodiments, the concentration of insoluble particles is of about 0 and about 10,000 per about 1 mL in suspension or upon reconstitution. In certain other embodiments, the concentration of insoluble particles with a characteristic size greater than or equal to about 10 μm is of about 0 to about 6,000 per about 1 mL in suspension or upon reconstitution. In certain embodiments, the concentration of insoluble particles with a characteristic size greater than or equal to about 25 μm is of about 0 to about 600 per about 1 mL in suspension or upon reconstitution.

In other embodiments, after dissolution or reconstitution of the particles following storage, SvPs are present in quantities from about 0 to about 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In some embodiments, the count of particles with characteristic size greater than or equal to about 10 μm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per about 1 mL, from about 0 to about 3 per about 1 mL, or from about 0 to about 1 per about 1 mL. In certain embodiments, the count of particles with characteristic size greater than or equal to about 25 μm is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. In still other embodiments, after dissolution or reconstitution of the particles following storage, the therapeutic biologic retains from about 0.5 to about 1.0 activity, e.g., from about 0.75 to about 1.0 activity, from about 0.9 to about 1.0 activity, from about 0.95 to about 1.0 activity, from about 0.99 to about 1.0 activity, or from about 0.999 to about 1.0 activity. In certain other embodiments, dissolution or reconstitution of the particles following storage provides less than about a 10% increase in aggregates of the therapeutic biologic, e.g., an antibody, antibody fragment, bovine serum albumin (BSA), or human serum albumin (HSA), (e.g., less than about 8%, less than about 5%, less than about 4%, less than about 3%, less than about 1%, less than about 0.5%, or less than about 0.1%) as compared to the therapeutic biologic in the aqueous first liquid prior to processing. In certain embodiments, the dissolution or reconstitution of the particles after storage provides less than about a 10% increase in fragments of the therapeutic biologic, e.g., an antibody, antibody fragment, bovine serum albumin (BSA), or human serum albumin (HSA), (e.g., less than about 8%, less than about 5%, less than about 4%, less than about 3%, less than about 1%, less than about 0.5%, or less than about 0.1%) as compared to the therapeutic biologic in the aqueous first liquid prior to processing. In some embodiments, the dissolution or reconstitution of the particles following storage provides less than about a 50% change in charge variants in the population of the therapeutic biologic, e.g., an antibody or an antibody fragment, (e.g., less than about 40, 30, 20, 10, 8, 5, 4, 3, or about 1%) as compared to therapeutic biologic prior to particle formation.

In some embodiments, after dissolution or reconstitution of the particles following storage, SvPs are present in quantities from about 0 to about 100,000,000 per about 1 mL, e.g., from about 0 to about 10,000,000 per about 1 mL, from about 0 to about 1,000,000 per about 1 mL, from about 0 to about 500,000 per about 1 mL, from about 0 to about 100,000 per about 1 mL, from about 0 to about 50,000 per about 1 mL, from about 0 to about 10,000 per about 1 mL, from about 0 to about 6,000 per about 1 mL, from about 0 to about 1,000 per about 1 mL, from about 0 to about 600 per about 1 mL, from about 0 to about 250 per about 1 mL, from about 0 to about 100 per about 1 mL, from about 0 to about 60 per about 1 mL, or from about 0 to about 10 per about 1 mL. In certain embodiments, the count of particles with characteristic size greater than or equal to about 10 μm is from about 0 to about 6,000 per about 1 mL, e.g., from about 0 to about 1,000 per about 1 mL, from about 0 to about 100 per about 1 mL, from about 0 to about 10 per about 1 mL, from about 0 to about 5 per 1 mL, from about 0 to about 3 per about 1 mL, or from about 0 to about 1 per about 1 mL. In certain other embodiments, the count of particles with characteristic size greater than or equal to about 25 μm is from about 0 to about 600 per about 1 mL, e.g., from about 0 to about 100 per about 1 mL, from about 0 to about 10 per about 1 mL, from about 0 to about 3 per about 1 mL, from about 0 to about 1 per about 1 mL, from about 0 to about 0.5 per about 1 mL, or from about 0 to about 0.1 per about 1 mL. In some embodiments, dissolution or reconstitution of the particles following storage provides less than about a 10% increase in aggregates of the therapeutic biologic, e.g., an antibody, antibody fragment, bovine serum albumin (BSA), or human serum albumin (HSA), (e.g., less than about 8%, less than about 5%, less than about 4%, less than about 3%, less than about 1%, less than about 0.5%, or less than about 0.1%) as compared to the therapeutic biologic in the aqueous first liquid prior to processing. In other embodiments, the dissolution or reconstitution of the particles after storage provides less than about a 10% increase in fragments of the therapeutic biologic, e.g., an antibody, antibody fragment, bovine serum albumin (BSA), or human serum albumin (HSA), (e.g., less than about 8%, less than about 5%, less than about 4%, less than about 3%, less than about 1%, less than about 0.5%, or less than about 0.1%) as compared to the therapeutic biologic in the aqueous first liquid prior to processing. In certain other embodiments, the dissolution or reconstitution of the particles following storage provides less than about 50% change in charge variants in the population of a therapeutic biologic, e.g., an antibody, antibody fragment, bovine serum albumin (BSA), or human serum albumin (HSA), e.g., less than about 40, about 30, about 20, about 10, about 8, about 5, about 4, about 3, or about 1%, as compared to the therapeutic biologic prior to particle formation.

In certain embodiments, the present disclosure includes concentrated particles comprising at least one therapeutic biologic, wherein the particles upon dissolution in water, buffers or other physiologically relevant aqueous liquids, e.g., biological fluids in the patients' body, have a substantially similar turbidity compared to a composition comprising the therapeutic biologic in the aqueous first liquid. The term "turbidity" means the cloudiness or haziness of a fluid caused by individual particles that remain insoluble after dissolution at the desired concentration in water, buffer or other physiologically relevant aqueous liquids, e.g., biological fluids in the patients' body. As used herein, "physiologically relevant" conditions as may be encountered inside a mammal or human, can apply. The skilled person will be able to determine the set of conditions most appropriate for testing in accordance with the ultimate application of the compositions described herein. In some embodiments, the particles upon dissolution in the aqueous first liquid has a substantially similar turbidity compared to a composition comprising the therapeutic biologic in the first aqueous liquid. In preferred embodiments, the particles upon dissolution in the aqueous first liquid is substantially free of turbidity. In certain preferred embodiments, the aqueous first liquid is water, aqueous buffer or a physiologically relevant aqueous liquid.

In some embodiments, the particles of the disclosure can be reconstituted into a liquid pharmaceutical composition to assess the turbidity or turbidance (USP <855>). Turbidity may be measured in units of FTU (Formazin Turbidity Units). This is achieved by comparing the turbidity of a sample with that of a formazine suspension. Turbidity may also be measured as Nephelometric Turbidity Units (NTU) where 1 NTU=1 FTU. In other embodiments, when 10 mg of particles are dissolved in 1 mL of liquid, turbidity can be of about 0 to about 4000 FTU, about 0 to about 1000 FTU, about 0 to about 500 FTU, about 0 to about 50 FTU, about 0 to about 20 FTU, about 0 to about 10 FTU, about 0 to about 5 FTU, about 0 to about 1 FTU, about 0 to about 0.1 FTU, or about 0 to about 0.01 FTU. In certain embodiments, the pharmaceutical composition has a turbidity of about 0 to about 4000 Formazin Turbidity Units (FTU). In certain other embodiments, the pharmaceutical composition upon dissolution in an aqueous liquid has a substantially similar turbidity compared to an aqueous composition comprising the therapeutic biologic in monomeric form. In preferred embodiments, the pharmaceutical composition upon dissolution in an aqueous liquid is substantially free of turbidity. In certain preferred embodiments, the aqueous liquid is water, aqueous buffer or a physiologically relevant aqueous liquid.

In other embodiments, the disclosure concerns highly concentrated compositions of low turbidity comprising a carbohydrate, a pH adjusting agent, a salt, a surfactant, a protein stabilizer, an emulsifier, an amino acid, and a plurality of particles comprising a therapeutic biologic, in a non-aqueous liquid carrier. In preferred embodiments, the disclosure concerns highly concentrated pharmaceutical compositions of low turbidity comprising trehalose, arginine hydrochloride, sodium succinate, succinic acid, citric acid, sodium citrate, histidine, histidine hydrochloride, sodium chloride, hydroxypropyl beta-cyclodextrin, polysorbate, or sorbitan monooleate, and a plurality of particles comprising an antibody, in ethyl oleate. In certain preferred embodiments, the pharmaceutical composition upon dissolution in water, aqueous buffer or any physiologically relevant aqueous liquid is substantially free of turbidity.

The particles comprising at least one therapeutic biologic described herein, can be used in a number of ways, as well as any methods for the delivery of the particles disclosed in, for example, in International Appliction Nos. PCT/US2017/063150 (Pub. No. WO 2018/098376), PCT/US2018/043774 (Pub. No. WO 2019/023392), PCT/US2019/033875 (Pub. No. WO 2019/226969), PCT/US2020/15957 (Pub. No. WO 2020/160323), PCT/US2020/050508 (Pub. No. WO 2021/050953), PCT/US2021/16878, and PCT/US2021/018806, the contents of each of which are hereby incorporated by reference in their entireties.

Methods of the Disclosure

The methods described herein, are generally provided for forming particles, the method comprising: a) providing an aqueous first liquid comprising a therapeutic biologic; b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic; c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture. As disclosed herein, the therapeutic biologic is an antibody, antibody fragment, bovine serum albumin (BSA), or human serum albumin (HSA). In certain embodiments, the therapeutic biologic has an activity per unit of about 0.5 to about 1.0. In certain preferred embodiments, the therapeutic biologic is an antibody, antibody fragment, bovine serum albumin (BSA), or human serum albumin (HSA). In preferred embodiments, the therapeutic biologic in the particles has an activity per unit of about 0.8 to about 1.0.

In certain embodiments, the particle includes less than about 10% internal void spaces, less than about 5% internal void spaces, less than about 1% internal void spaces, or less than about 0.5% internal void spaces after removing the aqueous first liquid and organic second liquid from the mixture. In preferred embodiments, the particle is substantially free from any internal void spaces after removing the aqueous first liquid and organic second liquid from the mixture.

In some embodiments, the circularity of the particle is from about 0.85 to about 1.00 after removing the aqueous first liquid and organic second liquid from the mixture. In other embodiments, the circularity of the particle is from about 0.90 to about 1.00 after removing the aqueous first liquid and organic second liquid from the mixture. In certain embodiments, the circularity of the particle is from about 0.95 to about 1.00 after removing the aqueous first liquid and organic second liquid from the mixture. In preferred embodiments, the circularity of the particle is from about 0.98 to about 1.00 after removing the aqueous first liquid and organic second liquid from the mixture. In certain preferred embodiments, the circularity of the particle is about 1.00 after removing the aqueous first liquid and organic second liquid from the mixture.

Droplets

Droplets as described herein, can be formed through any of several continuous process techniques as disclosed herein. These include continuous membrane emulsification, continuous homogenization, continuous mechanical stirring, continuous mechanical shaking, continuous impinging jet mixing, continuous ultra-sound, continuous sonication, continuous micro-channel emulsification, continuous micro-sieve emulsification, continuous capillary extrusion, continuous static mixing, or a combination thereof. In certain embodiments, the continuous micro-channel emulsification is accomplished using a microfluidic chip based device. The terms "mixer" and "homogenizer" are used herein, interchangeably in the broadest sense. The term "droplet" or "droplets" or "drops" refer to a material that has a liquid outer surface. In some embodiments, the aqueous liquid droplets of step a) are formed by continuous membrane emulsification, continuous homogenization, continuous mechanical stirring, continuous mechanical shaking, continuous impinging jet mixing, continuous ultra-sound, continuous sonication, continuous micro-channel emulsification, continuous microsieve emulsification, continuous capillary extrusion, continuous static mixing, or a combination thereof. In certain embodiments, the continuous micro-channel emulsification is accomplished using a microfluidic chip based device. In other embodiments, the aqueous liquid droplets of step a) are formed through continuous membrane emulsification, continuous homogenization, continuous impinging jet mixing, continuous static mixing, or a combination thereof. In certain embodiments, the continuous membrane emulsification is conducted by rotating membrane emulsification, cross-flow membrane emulsification, or a combination thereof. In still other embodiments, the continuous homogenization includes but are not limited to high shear mixing, high pressure microorifice homogenization, or a combination thereof. A person of ordinary skill in the field of this disclosure can readily assess the shear homogenization or pressure homogenization of the disclosed methods using routine and standard techniques for high or how shear homogenization, or high or low pressure homogenization. In certain other embodiments, the continuous mechanical stirring is conducted by a turbulent stirred vessel, a magnetic stirring device, a mechanical stirring device, or a combination thereof. In certain preferred embodiments, the continuous static mixing comprises laminar flow, turbulent flow, transition flow, or a combination thereof.

As used herein, the term dispersion refers to a mixture of droplets within a second liquid where the typical inter-droplet spacing and droplet number concentration are fairly uniform on the timescale of the dehydration process. Such dispersions may be stable due to the presence of components having both hydrophilic and hydrophobic sites, e.g., as in a surfactant or emulsifier. The terms "dispersed phase" (DP) and "continuous phase" (CP) are related to a dispersion system, in which an aqueous first liquid is dispersed within an organic second liquid. In such a dispersion system, the term "dispersed phase" (DP) or "feed solution" refers to a preparation of the therapeutic biologic in the aqueous first liquid, either as a solution, a slurry, or some other liquid form, e.g., aqueous liquid droplets, dispersed in the continuous phase. The term "continuous phase" (CP) refers to an organic second liquid surrounding the aqueous first liquid, e.g., dispersed phase. As used herein, the term "emulsion" refers to a heterogeneous system consisting of a continuous phase and a non-continuous phase, e.g., the dispersed phase, capable of forming droplets in the continuous phase (CP). The term "emulsifier" refers to an agent that can reduce and/or eliminate the surface and the interfacial tension in a two-phase system. The emulsifier agent may possess both hydrophilic and lipophilic groups. The emulsifier may be considered to be either in the continuous phase (CP), dispersed phase (DP), or both. In some embodiments, the preparation contains excipients. In other embodiments, the preparation further contains a buffer. In certain embodiments, the preparation further contains a surfactant.

As described herein, in liquid-liquid or solid-liquid dispersions (emulsions or suspensions, respectively), the dispersed phase (DP) is present as discrete droplets or particles which are distributed throughout the continuous phase (CP).

In some embodiments, the aqueous first liquid is water, 0.9% saline, lactated Ringer's solution, a buffer, dextrose 5%, or a combination thereof. In preferred embodiments, the aqueous first liquid is water. In other embodiments, the buffer is acetate buffer, histidine buffer, succinate buffer, HEPES buffer, tris buffer, carbonate buffer, citrate buffer, phosphate buffer, phosphate-buffered saline, glycine buffer, barbital buffer, cacodylate buffer, ammonium formate buffer, urea solution, or a combination thereof.

In other embodiments, the aqueous first liquid further comprises a carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, a surfactant, or a combination thereof.

In certain embodiments, the carbohydrate is dextran, trehalose, sucrose, agarose, mannitol, lactose, sorbitol, maltose, or a combination thereof. In preferred embodiments, the carbohydrate is trehalose, cyclodextrins, hydroxypropyl beta-cyclodextrin, sucrose, sulfobutylether beta-cyclodextrin, or a combination thereof.

In some embodiments, the pH adjusting agent is acetate, citrate, glutamate, glycinate, histidine, lactate, maleate, phosphate, succinate, tartrate, bicarbonate, aluminum hydroxide, phosphoric acid, hydrochloric acid, DL-lactic/glycolic acids, phosphorylethanolamine, tromethamine, imidazole, glyclyglycine, monosodium glutamate, sodium hydroxide, potassium hydroxide, or a combination thereof. In other embodiments, the pH adjusting agent is citrate, histidine, phosphate, succinate, sodium hydroxide, potassium hydroxide, or a combination thereof. In certain embodiments, the pH adjusting agent is hydrochloric acid or citric acid.

In other embodiments, the salt is sodium chloride, calcium chloride, potassium chloride, sodium hydroxide, stannous chloride, magnesium sulfate, sodium glucoheptonate, sodium pertechnetate, guanidine hydrochloride, potassium hydroxide, magnesium chloride, potassium nitrate, or a combination thereof. In preferred embodiments, the salt is sodium chloride.

In certain embodiments, the protein stabilizer is trehalose, polyethylene glycol (PEG), polyoxamers, polyvinylpyrrolidone, polyacrylic acids, poly(vinyl) polymers, polyesters, polyaldehydes, tert-polymers, polyamino acids, hydroxyethylstarch, N-methyl-2-pyrrolidone, sorbitol, sucrose, mannitol, cyclodextrin, hydroxypropyl beta-cyclodextrin, sulfobutylether beta-cyclodextrin, pentetic acid, or a combination thereof. In preferred embodiments, the protein stabilizer is trehalose, cyclodextrin, hydroxypropyl beta-cyclodextrin, sulfobutylether beta-cyclodextrin, pentetic acid, or a combination thereof. In certain preferred embodiments, the PEG is PEG 200, PEG 300, PEG 3350, PEG 8000, PEG 10000, PEG 20000, or a combination thereof.

In some embodiments, the emulsifier is polysorbate 80, polysorbate 60, polysorbate 20, sorbitan monooleate, ethanolamine, polyoxyl 35 castor oil, poloxyl 40 hydrogenated castor oil, carbomer 1342, a corn oil-mono-di-triglyceride, a polyoxyethylated oleic glyceride, a poloxamer, or a combination thereof. In preferred embodiments, the fatty acid ester of sorbitol is a sorbitan ester, e.g., span 20, span 40, span 60, or span 80. In certain preferred embodiments, the emulsifier is polysorbate 80, sorbitan monooleate, or a combination thereof.

In other embodiments, the amino acid is alanine, aspartic acid, cysteine, isoleucine, glutamic acid, leucine, phenylalanine, pyrrolysine, serine, selenocysteine, threonine, tryptophan, tyrosine, valine, asparagine, arginine, histidine, glycine, glutamine, proline, methionine, or a combination thereof. In certain embodiments, the amino acid is arginine, histidine, proline, asparagine, or a combination thereof. In preferred embodiments, the amino acid is histidine.

In some embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, phosphatidylcholine, polyglycerol polyricinoleate, siloxanes, cetyl polyethylene glycol/polypropylene glycol-10/1 dimethicone triglyceride, bis-polyethylene glycol/polypropylene glycol-14/14 dimethicone, bis-(glyceryl/lauryl) glyceryl lauryl dimethicone and caprylic/capric triglyceride, cetyl polyethylene glycol/polypropylene glycol-10/1 dimethicone, phospholipids, or a combination thereof. In other embodiments, the surfactant is polysorbate, docusate or lecithin. In certain embodiments, the surfactant is polysorbate 20, polysorbate 60, or polysorbate 80, e.g., Tween 20, Tween 60, Tween 80. In still other embodiments, the surfactant is polysorbate 20 or polysorbate 80. In certain preferred embodiments, the fatty acid ester of sorbitol is a sorbitan ester, e.g., span 20, span 40, span 60, or span 80. In other preferred embodiments, the surfactant is an ionic surfactant. In preferred embodiments, the surfactant is polysorbate 80.

In other embodiments, the concentration of the therapeutic biologic in the aqueous first liquid as described herein, is about 10 mg/mL to about 650 mg/mL, e.g., about 20, 30, 50, 75, 100, 125, 150, 175, 200, 225, 250, 275, 300, 325, 350, 375, 400, 425, 450, 475, 500, 525, 550, 575, 600, 625 mg/mL to about 650 mg/mL; about 20 mg/mL to about 625 mg/mL, e.g., about 20, 30, 50, 75, 100, 125, 150, 175, 200, 225, 250, 275, 300, 325, 350, 375, 400, 425, 450, 475, 500, 525, 550, 575, 600 mg/mL to about 625 mg/mL; about 20 mg/mL to about 600 mg/mL, e.g., about 20, 30, 50, 75, 100, 125, 150, 175, 200, 225, 250, 275, 300, 325, 350, 375, 400, 425, 450, 475, 500, 525, 550, 575 mg/mL to about 600 mg/mL; about 20 mg/mL to about 575 mg/mL, e.g., about 20, 30, 50, 75, 100, 125, 150, 175, 200, 225, 250, 275, 300, 325, 350, 375, 400, 425, 450, 475, 500, 525, 550 mg/mL to about 575 mg/mL; about 20 mg/mL to about 550 mg/mL, e.g., about 20, 30, 50, 75, 100, 125, 150, 175, 200, 225, 250, 275, 300, 325, 350, 375, 400, 425, 450, 475, 500, 525 mg/mL to about 550 mg/mL; about 20 mg/mL to about 525 mg/mL, e.g., about 20, 30, 50, 75, 100, 125, 150, 175, 200, 225, 250, 275, 300, 325, 350, 375, 400, 425, 450, 475, 500 mg/mL to about 525 mg/mL; about 20 mg/mL to about 500 mg/mL, e.g., about 20, 30, 50, 75, 100, 125, 150, 175, 200, 225, 250, 275, 300, 325, 350, 375, 400, 425, 450, 475 mg/mL to about 500 mg/mL; about 20 mg/mL to about 475 mg/mL, e.g., about 20, 30, 50, 75, 100, 125, 150, 175, 200, 225, 250, 275, 300, 325, 350, 375, 400, 425, 450 mg/mL to about 475 mg/mL; about 20 mg/mL to about 450 mg/mL, e.g., about 20, 30, 50, 75, 100, 125, 150, 175, 200, 225, 250, 275, 300, 325, 350, 375, 400, 425 mg/mL to about 450 mg/mL; about 20 mg/mL to about 425 mg/mL, e.g., about 20, 30, 50, 75, 100, 125, 150, 175, 200, 225, 250, 275, 300, 325, 350, 375, 400 mg/mL to about 425 mg/mL; about 20 mg/mL to about 400 mg/mL, e.g., about 20, 30, 50, 75, 100, 125, 150, 175, 200, 225, 250, 275, 300, 325, 350, 375 mg/mL to about 400 mg/mL; about 20 mg/mL to about 375 mg/mL, e.g., about 20, 30, 50, 75, 100, 125, 150, 175, 200, 225, 250, 275, 300, 325, 350 mg/mL to about 375 mg/mL; about 20 mg/mL to about 350 mg/mL, e.g., about 20, 30, 50, 75, 100, 125, 150, 175, 200, 225, 250, 275, 300, 325 mg/mL to about 350 mg/mL; about 20 mg/mL to about 325 mg/mL, e.g., about 20, 30, 50, 75, 100, 125, 150, 175, 200, 225, 250, 275, 300 mg/mL to about 325 mg/mL; or about 20 mg/mL to about 300 mg/mL, e.g., about 20, 30, 50, 75, 100, 125, 150, 175, 200, 225, 250, 275 mg/mL to about 300 mg/mL.

In certain embodiments of the disclosure, the concentration of the therapeutic biologic in the aqueous first liquid is from about 0.0001 mg/mL to about 1000 mg/mL, e.g., about 100 to about 800, about 200 to about 700, about 200 to about 600, or about 300 mg/mL to about 700 mg/mL. In other embodiments, the concentration of the therapeutic biologic in the aqueous first liquid is about 10 mg/mL to about 500 mg/mL. In still other embodiments, the concentration of the therapeutic biologic in the aqueous first liquid is about 10 mg/mL to about 100 mg/mL. In preferred embodiments, the concentration of the therapeutic biologic in the aqueous first liquid is about 20 mg/mL to about 100 mg/mL. In some embodiments, the particles have a mass loading of the therapeutic biologic from about 1% to about 100%.

In other embodiments, the aqueous first liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, or less than about 0.5 mPa·s (one millipascal-second). The term "viscosity" is used to describe the property of a fluid acting to resist shearing flow. For the purposes of the present disclosure, viscosity can be determined using a rheometer, e.g., AR-G2 Rheometer (TA Instruments, USA), fitted with a cone and plate (2°/40 mm) at 25° C. at a specified shear rate. In certain embodiments, the viscosity is measured at a shear rate in the Newtonian regime. The term "Newtonian regime" means a range of shear rates which are linearly proportional or nearly linearly proportional to the local strain rate at every point. In some embodiments, the viscosity is measured at a shear rate of about 100 s$^{-1}$ or greater, e.g., at about 1000 s$^{-1}$ or greater than about 1000 s$^{-1}$. Methods of controlling viscosity include temperature regulation and viscosity modifying additives. Mixtures of liquids may also be used to control viscosity. The units "mPa·s" and "cP" are used herein, interchangeably in the broadest sense.

In some embodiments, the aqueous first liquid has a viscosity of less than about 100 mPa·s. In other embodiments, the aqueous first liquid has a viscosity of less than about 10 mPa·s. In certain other embodiments, the aqueous first liquid has a viscosity of less than about 3 mPa·s. In still other embodiments, the aqueous first liquid has a viscosity of less than about 0.9 mPa·s. In preferred embodiments, the aqueous first liquid has a viscosity of less than about 0.5 mPa·s.

In preferred embodiments, the organic second liquid is an organic solvent.

In some embodiments, the organic solvent is acetone, acetonitrile, acyclic alkanes (e.g., hexanes, heptane, pentane), amyl acetate, butanol, butyl acetate, chlorobenzene, chloroform, cumene, cyclohexane, 1,2-dichloroethene, dichloromethane, diethyl ether, dimethoxyethane, dimethylacetamide, dimethylformamide, dimethyl sulfoxide, 1,4-dioxane, ethanol, 2-ethoxyethanol, ethyl acetate, ethyl nitrate, ethyleneglycol, hydrazine, isopropanol, methanol, methyl acetate, 2-methyl-1-butanol, 2-methyl-1-propanol, methylbutyl ketone, methylcyclohexane, methylethyl ketone, methylpyrrolidone, methyl tert-butyl ether, nitromethane, propanol, propyl acetate, sulfolane, propyleneglycol, tetrahydrofuran, tetralin, toluene, 1,1,2-tricholoroethane, triethylamine, xylene, benzyl benzoate, ethyl lactate, dimethyl isosorbide, dimethyl sulfoxide, glycofurol, diglyme, methyl tert-butyl ether, polyethylene glycol, 2-pyrrolidone, tetrahydrofurfuryl alcohol, trigylcerides, octyl acetate, ethanol, butanol, octanol, decanol, diglyme, tocopherol, octa-fluoropropane, (perfluorohexyl)octane, n-acetyl-tryptophan, trigylcerides, triglycerides of the fractionated plant fatty acids C8 and C10, propylene glycol diesters of saturated plant fatty acids C8 and C10, ethyl laurate, methyl caprylate, ethyl laurate, ethyl myristate, ethyl caprylate, methyl caprate, methyl myristate, methyl oleate, methyl linoleate, dimethyl adipate, dibutyl suberate, diethyl sebacate, ethyl macadamiate, trimethylolpropane triisosterate, isopropyl laurate, isopropyl myristate, diethyl succinate, polysorbate esters, ethanol amine, propanoic acid, triacetin, citral, anisole, anethol, benzaldehyde, linalool, caprolactone, phenol, thioglycerol, dimethylacetamide, ethyl formate, ethyl hexyl acetate, eugenol, clove bud oil, diethyl glycol monoether, dimethyl isosorbide, isopropyl acetate, methyl isobutyl ketone, methyl tert-butyl ether, N-methyl pyrrolidone, perfluorodecalin, 2-pyrrolidone, ethyl oleate, ethyl caprate, dibutyl adipate, hexanoic acid, octanoic acid, diethyl glycol monoether, gamma-butyrolactone, polyoxyl 40 hydrogenated castor oil, polyoxyl 35 castor oil, propylene carbonate, octanol, hexanol, sorbitan monooleate, n-acetyl-tryptophan, solketal, an alkyl acetate, an aryl acetate, an aryl alkyl acetate, tolyl acetate, benzyl acetate, polysorbate 80, phenethyl acetate, phenyl acetate, glycerol, or a combination thereof. In certain embodiments, the organic solvent is a Class III solvent as defined by the International Council for Harmonisation (ICH) guidelines.

In other embodiments, the organic solvent is benzyl alcohol, benzyl benzoate, castor oil, coconut oil, corn oil, cottonseed oil, fish oil, grape seed oil, hazelnut oil, hydrogenated palm seed oil, olive oil, peanut oil, peppermint oil, safflower oil, sesame oil, soybean oil, sunflower oil, vegetable oil, walnut oil, polyethylene glycol, glycofurol, acetone, diglyme, dimethylacetamide, dimethyl isosorbide, dimethyl sulfoxide, ethanol, methyl acetate, ethyl acetate, propyl acetate, butyl acetate, ethyl ether, ethyl lactate, isopropyl acetate, methyl acetate, methyl isobutyl ketone, methyl tert-butyl ether, N-methyl pyrrolidone, perfluorodecalin, 2-pyrrolidone, trigylcerides, tetrahydrofurfuryl alcohol, triglycerides of the fractionated plant fatty acids C8 and C10 (e.g., MIGLYOL® 810 and MIGLOYL® 812N), propylene glycol diesters of saturated plant fatty acids C8 and C10 (e.g., MIGLYOL® 840), ethyl oleate, ethyl caprate, dibutyl adipate, fatty acid esters, hexanoic acid, octanoic acid, triacetin, diethyl glycol monoether, gamma-butyrolactone, eugenol, clove bud oil, citral, limonene, hexanes, heptane, or a combination thereof.

In certain embodiments, the organic solvent is acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, or a combination thereof. In preferred embodiments, the organic solvent is methylacetate, ethylacetate, propylacetate, butylacetate, amylacetate, 2-ethylhexylacetate, heptane, or a combination thereof.

In some embodiments, the organic second liquid further comprises a carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, a surfactant, or a combination thereof. In preferred embodiments, the organic second liquid further comprises a surfactant.

In other embodiments, the surfactant is polysorbate, magnesium stearate, sodium dodecyl sulfate, TRITON™ N-101, glycerin, polyoxyethylated castor oil, docusate, sodium stearate, decyl glucoside, nonoxynol-9, cetyltrimethylammonium bromide, sodium bis(2-ethylhexyl) sulfosuccinate, lecithin, sorbitan ester, phosphatidylcholine, polyglycerol polyricinoleate, siloxanes, cetyl polyethylene glycol/polypropylene glycol-10/1 dimethicone triglyceride, bis-polyethylene glycol/polypropylene glycol-14/14 dimethicone, bis-(glyceryl/lauryl) glyceryl lauryl dimethicone and caprylic/capric triglyceride, cetyl polyethylene glycol/polypropylene glycol-10/1 dimethicone, phospholipids, or a combination thereof. In certain embodiments, the surfactant is polysorbate, docusate or lecithin. In certain other embodiments, the surfactant is polysorbate 20, polysorbate 60, or polysorbate 80, e.g., Tween 20, Tween 60, Tween 80. In still other embodiments, the surfactant is polysorbate 20 or polysorbate 80. In certain preferred embodiments, the fatty acid ester of sorbitol is a sorbitan ester, e.g., span 20, span 40, span 60, or span 80. In other preferred embodiments, the surfactant is an ionic surfactant. In preferred embodiments, the surfactant is polysorbate 80.

In some embodiments, the organic second liquid has a viscosity of less than about 200 mPa·s, less than about 150 mPa·s, less than about 125 mPa·s, less than about 100 mPa·s, less than about 75 mPa·s, less than about 75 mPa·s, less than about 70 mPa·s, less than about 65 mPa·s, less than about 60 mPa·s, less than about 55 mPa·s, less than about 50 mPa·s, less than about 45 mPa·s, less than about 40 mPa·s, less than about 35 mPa·s, less than about 30 mPa·s, less than about 25 mPa·s, less than about 20 mPa·s, less than about 19 mPa·s, less than about 18 mPa·s, less than about 17 mPa·s, less than about 16 mPa·s, less than about 15 mPa·s, less than about 14 mPa·s, less than about 13 mPa·s, less than about 12 mPa·s, less than about 11 mPa·s, less than about 10 mPa·s, less than about 9.5 mPa·s, less than about 9 mPa·s, less than about 8.5 mPa·s, less than about 8 mPa·s, less than about 7.5 mPa·s, less than about 7 mPa·s, less than about 6.5 mPa·s, less than about 6 mPa·s, less than about 5.5 mPa·s, less than about 5 mPa·s, less than about 4.5 mPa·s, less than about 4 mPa·s, less than about 3.5 mPa·s, less than about 3 mPa·s, less than about 2.5 mPa·s, less than about 2 mPa·s, less than about 1.5 mPa·s, less than about 1 mPa·s, less than about 0.5 mPa·s, less than about 0.1 mPa·s, less than about 0.05 mPa·s, or less than about 0.01 mPa·s (one millipascal-second). Methods of controlling viscosity include temperature regulation and viscosity modifying additives. Mixtures of liquids may also be used to control viscosity.

In other embodiments, the organic second liquid has a viscosity of less than about 50 mPa·s. In some embodiments, the organic second liquid has a viscosity of less than about 10 mPa·s. In certain other embodiments, the organic second liquid has a viscosity of less than about 5 mPa·s. In still other embodiments, the organic second liquid has a viscosity of less than about 2 mPa·s.

In other embodiments as described herein, step c) further comprises decreasing the temperature of the organic second liquid to a temperature within about 30° C. of the freezing point of the aqueous first liquid. In some embodiments, the boiling point of the organic second liquid at atmospheric pressure is from about 0 to about 200° C. In certain embodiments the temperature, pressure, and water content of the organic second liquid, in which the aqueous liquid droplets are dispersed can be regulated to control the dehydration kinetics.

In some embodiments, the continuous process of step b), comprises continuous membrane emulsification, continuous homogenization, continuous mechanical stirring, continuous mechanical shaking, continuous impinging jet mixing, continuous ultra-sound, continuous sonication, continuous micro-channel emulsification, continuous microsieve emulsification, continuous capillary extrusion, continuous static mixing, or a combination thereof. In certain embodiments, the continuous micro-channel emulsification is accomplished using a microfluidic chip based device. In other embodiments, the continuous process of step b), comprises continuous membrane emulsification, continuous homogenization, continuous impinging jet mixing, continuous static mixing, or a combination thereof. In certain other embodiments, the continuous membrane emulsification is conducted by rotating membrane emulsification, cross-flow membrane emulsification, or a combination thereof. In still other embodiments, the continuous homogenization is conducted by shear homogenization, pressure homogenization, rotor-stator homogenization, microfluidization, or a combination thereof. A person of ordinary skill in the field of this disclosure can readily assess the shear homogenization or pressure homogenization of the disclosed methods using routine and standard techniques for high or how shear homogenization, or high or low pressure homogenization. In certain embodiments, the continuous mechanical stirring is conducted by a turbulent stirred vessel, a magnetic stirring device, a mechanical stirring device, or a combination thereof. In certain preferred embodiments, the continuous static mixing comprises laminar flow, turbulent flow, transition flow, or a combination thereof.

Formation of Particles

The particles as described herein, can be formed by contacting the aqueous liquid droplets that include a therapeutic biologic and an aqueous first liquid with an organic second liquid that facilitates removal of the aqueous first liquid from the aqueous liquid droplets. In some embodiments, the aqueous liquid droplets are continuously formed in the organic second liquid. Particle formation begins to take place when at least a subset of the components of the aqueous liquid droplets begin to undergo precipitation or phase separation as the aqueous first liquid is removed. In preferred embodiments, the aqueous liquid droplets are dried after continuously contacting the aqueous liquid droplets comprising the therapeutic biologic with the organic second liquid.

In some embodiments, particles are formed after the aqueous first liquid disperses throughout the organic second liquid, e.g., through a diffusion process. In other embodiments the organic second liquid may have varying degrees of miscibility with the aqueous first liquid and represent a weakly or negligibly solubilizing medium in relation to the components of the particles or a subset of the components of the particles, e.g., the therapeutic biologic. The therapeutic biologic, e.g., antibody, antibody fragment, bovine serum albumin (BSA), or human serum albumin (HSA), is typically less soluble in the organic second liquid relative to the aqueous first liquid in the timeframe of or under the conditions of production, e.g., at least about 5, 10, 100, or about 1000 times less soluble. In preferred embodiments, the organic second liquid is an organic solvent. The organic second liquid can further include a carbohydrate, a pH adjusting agent, a salt, a chelator, a mineral, a polymer, a surfactant, an amino acid, an oligopeptide, a biologic excipient, a chemical excipient, an antiseptic, an antioxidant, a paraben, a bactericide, a fungicide, a vitamin, a preservative, an analgesic, a nutrient media, or a combination thereof. Exemplary aqueous first liquids may contain stabilizers, e.g., crowding agents. These solutions, in certain embodiments, include excipients such as a salt (e.g., sodium chloride), sugars and sugar alcohols (e.g., sorbitol, dextran 40, dextran 6000, or trehalose), polymers (e.g., PEG 3350, PEG 300, PEG 8000, PEG 20k, Ficoll 400, Ficoll 70, or polyvinylpyrrolidone, e.g., Povidone), a protein (e.g., bovine serum albumin (BSA), or human serum albumin (HSA)), or a combination thereof. In still other embodiments, where the aqueous first liquid is water, particles are obtained via osmotic drying of the aqueous liquid droplets. The organic second liquid that is used to continuously dry the particles, in certain embodiments, include a high concentration of a solute (therapeutic biologic and/or excipient, e.g., surfactant), e.g., at least about 0.03 osmol, at least about 0.2 osmol, at least about 1.0 osmol, or at least about 1.2 osmol.

In other embodiments, the surfactant in the organic second liquid helps to prevent coalescence of the aqueous liquid droplets. In certain embodiments, an oligopeptide excipient, a protein excipient, the therapeutic biologic(s) themselves, e.g., antibody, antibody fragment, bovine serum albumin (BSA), or human serum albumin (HSA), or a combination thereof, act as surfactants.

In some embodiments, the aqueous liquid droplets in the mixture of step c) are dehydrated after contact with the organic second liquid of step b). In other embodiments, the dehydration of the aqueous liquid droplets in the mixture of step c) occurs in a continuous drying tube, a continuous drying vessel, or a combination thereof. In certain other embodiments, the continuous drying tube is further connected to at least one continuous process. In still other embodiments, the continuous drying vessel is further connected to at least one continuous process. In certain embodiments, the continuous drying vessel comprises continuous mechanical stirring. In certain preferred embodiments, the continuous mechanical stirring is conducted by a turbulent stirred vessel, a magnetic stirring device, or a mechanical stirring device. In some embodiments, the average residence time T of the particles in the continuous drying vessel and the relationship between this time and the characteristic particle formation time t* is considered in the design and sizing of the continuous drying vessel. In some embodiments, the average residence time can be estimated as $\tau=V/Q$, where V is the volume of the continuous drying vessel and Q is the volumetric flow rate of product through it. In some embodiments, the particle resides in the continuous drying vessel for about 0 to about 10,000 seconds, e.g., about 0 to about 5,000 seconds, 1,000 seconds, 500 seconds, 400 seconds, 300 seconds, 200 seconds, 100 seconds, 90 seconds, 80 seconds, 70 seconds, 60 seconds, 50 seconds, 40 seconds, 30 seconds, 20 seconds, 10 seconds, 9 seconds, 8 seconds, 7 seconds, 6 seconds, 5 seconds, 4 seconds, 3 seconds, 2 seconds, or 1 second. In some embodiments, the ratio of the characteristic particle formation time to the average residence time $t^*/\tau$ is a figure of merit. In some embodiments, the ratio of the characteristic particle formation time to the average residence time is about 0 to about 100, e.g., 0 to about 100, 50, 25, 10, 5, 4, 3, 2, 1, 0.9, 0.8, 0.7, 0.6, 0.5, 0.4, 0.3, 0.2, or 0.1.

The actual continuous dehydration or desiccation time may vary as a function of the properties of the organic second liquid in addition to changes that take place in the drop as the concentration of the solutes, precipitation of solutes, and/or phase separation begin to take place. Relevant properties of the organic second liquid that influence the drying time include, e.g., the solubility of the first liquid in the organic second liquid, the saturation state of the organic second liquid, the diffusivity of the first liquid in the organic second liquid, and the polarity of the organic second liquid. The term "polarity" or "polarities" refer to the overall solvation capability (solvation power) of the aqueous first liquid, which in turn depends on the action of all possible, nonspecific and specific, intermolecular interactions between solute ions or molecules and solvent molecules, excluding, however, those interactions leading to definite chemical alterations of the ions of molecules of the solute (Chem. Rev., 1994, 94, 2319-2358). A prediction of liquid polarity may be made from their dielectric constant. Liquids with high dielectric constants are considered more polar and those with low dielectric constants are considered less polar or nonpolar (<~15). Depending on the chosen continuous process conditions, continuous dehydration of the aqueous liquid droplets to form particles may occur over a period of nanoseconds to days. In embodiments where the first liquid is aqueous and where the second liquid is an organic solvent, drying times can vary, e.g., between 1 μs and 1000 s depending on the solvent chemistry. In some embodiments, there characteristic particle formation time can be estimated as $t^* = \rho r^2/3 \, Dc \, (1-\beta)$, where p is the density of the first liquid, r is the initial radius of the droplet, D is the diffusivity of the first liquid in the second liquid, c is the solubility of the first liquid in the second liquid, and β is the fractional level of saturation of the second liquid with the first liquid at the start of the particle formation process.

The term "primary desiccation" refers to a step by which an aqueous liquid droplet comprising an aqueous first liquid is placed in continuous contact with an organic second liquid and continuously dehydrated or desiccated by the organic second liquid, e.g., through dispersal of the aqueous first liquid in the organic second liquid. The term "secondary desiccation" refers to a post-processing step, e.g., after the continuous removal of the aqueous first liquid and organic second liquid, by which the residual moisture and/or aqueous first liquid and organic second liquid content of the particles is modified. Exemplary methods of secondary desiccation include vacuum drying, air filter drying, with or without the application of heat, lyophilization, fluidized bed drying, tray drying, belt drying, or slurry spray drying. In preferred embodiments, the aqueous first liquid and/or organic second liquid is removed through centrifugation, sieving, filtration, magnetic collection, solvent exchange, decanting, hydrocyclone separation, or a combination thereof. In certain preferred embodiments, the filtration is tangential flow filtration or normal flow filtration.

In certain embodiments of the continuous dehydrating process, the organic second liquid includes or is in contact with a drying substance, i.e., a desiccant, to absorb the aqueous first liquid or otherwise sequester it, e.g., by reaction. Such substances can be useful for ensuring a uniform, steady-state degree of saturation of the aqueous first liquid in the organic second liquid during the continuous dehydrating process. Exemplary desiccants include, but are not limited to celite, molecular sieves, phosphorous pentoxide, magnesium sulfate, silica, calcium chloride, activated charcoal, potassium carbonate, activated alumina, or a combination thereof.

Post-Processing

In some embodiments, the methods as described herein, include removing the particles from the aqueous first liquid and organic second liquid through centrifugation, sieving, filtration, magnetic collection, filtration solvent exchange, decanting, hydrocyclone separation, or a combination thereof. In other embodiments, the aqueous first liquid and organic second liquid from the mixture of step d) are removed through centrifugation, sieving, filtration, magnetic collection, solvent exchange, decanting, or a combination thereof. In certain preferred embodiments, the filtration is tangential flow filtration or normal flow filtration.

In other embodiments, the methods as described herein, further comprise washing the particles after step d) with a washing fluid, e.g., an organic liquid, a supercritical fluid, a cryogenic liquid, or a combination thereof. In certain embodiments, the washing fluid is an organic liquid, a supercritical fluid, a cryogenic liquid, or a combination thereof.

The primary desiccation of the particles, e.g., removing the aqueous first liquid and organic second liquid from the mixture to produce particles, can be further processed through methods as described herein, e.g., secondary desiccation. These include, but are not limited to convective gas drying, forced gas drying, freeze drying, critical point drying, vacuum drying, emulsion solvent evaporation, emulsion solvent diffusion, or a combination thereof. In certain embodiments, the particles are further dried by lyophilization or vacuum desiccation, e.g., secondary desiccation. In certain other embodiments, residual quantities of the aqueous first liquid and organic second liquid in the particles after primary desiccation are less than about 10% by weight, e.g., less than about 5% by weight, less than about 3% by weight, or less than about 1% by weight. In certain embodiments, the particles are dried in vacuo.

In some embodiments, the particles are removed from the aqueous first liquid and organic second liquid from the mixture through a solvent exchange washing procedure. After removal of most of the aqueous first liquid and organic second liquid from the mixture (e.g., after centrifugation and supernatant decanting), a third liquid may be added which may be volatile, miscible with the aqueous first liquid and organic second liquid, and in which the particles are not soluble under the conditions of washing. In other embodiments, the third liquid is more volatile than the aqueous first liquid and organic second liquid, which may be easier to remove. Additional cycles of concentration, supernatant removal, and backfilling with the third liquid can lead to substantial reduction of the content of the aqueous first liquid and organic second liquid in the particle after the removal of most of the aqueous first liquid and organic second liquid. The third liquid can be subsequently removed, e.g., by application of heat and/or vacuum, or removed by lyophilization. In certain embodiments, the third liquid is an organic liquid. In certain other embodiments, the volatile third liquid is a supercritical fluid, e.g., supercritical $CO_2$, a cryogenic fluid, e.g., liquid nitrogen, or a mixture of one of these liquids and an organic liquid thereof. In still other embodiments, the boiling point of the volatile third liquid at atmospheric pressure is from about −200 to about 200° C., e.g., from about −200 to about 100° C., from about −200 to about 75° C., or from about −200 to about 50° C. In certain other embodiments, the methods described herein, further include washing the particles with a fourth liquid. In certain preferred embodiments, the fourth liquid is an organic solvent. The fourth liquid can also be removed through evaporation, vacuum desiccation or lyophilization, e.g., vacuum drying, with or without the application of heat, lyophilization, fluidized bed drying, tray drying, belt drying, or slurry spray drying. In preferred embodiments, the particles are further dried by lyophilization or vacuum desiccation. In certain embodiments, the particles are dried using house vacuum for up to about 15 h.

In other embodiments, gas is used to further dry the particles after primary desiccation. In some embodiments, the particles are further dried by contacting the particles with a stream of gas. In certain embodiments, the gas has a temperature from about −80 to about 200° C. In certain other embodiments, the gas has a temperature from about 10 to about 40° C. In certain other embodiments, the humid gas drying is conducted at temperatures less than about 35° C.

In certain embodiments, the gas has a relative humidity greater than about 0% to less than about 100%. In certain other embodiments, the gas has a relative humidity greater than about 30% to less than about 100%. In still other embodiments, the gas has a relative humidity greater than about 50% to less than about 100%. In certain preferred embodiments, the gas has a relative humidity greater than about 70% to less than about 100%. In preferred embodiments, the gas has a relative humidity greater than about 50% to less than about 80%. As disclosed herein, the humid gas can displace and/or remove the residual aqueous first liquid and/or organic second liquid in the particles with moisture. In some embodiments, the gas removes the aqueous first liquid, organic second liquid, or a combination thereof, from the particles. In other embodiments, the gas further adds moisture to the particles. In some embodiments, the gas comprises helium, air, nitrogen or argon. In certain embodiments, the drying gas comprises helium or air.

The particles as described herein, can be subjected to one or more desiccation steps after separation from the aqueous first liquid and organic second liquid, e.g., after primary desiccation. Such steps can be utilized to remove liquids, and/or to modulate residual quantities of the aqueous first liquid and organic second liquid in the particles. In certain embodiments, residual quantities of the aqueous first liquid and organic second liquid can persist in the particles after primary desiccation. In certain other embodiments, secondary desiccation or drying is useful for reducing quantities of the aqueous first liquid and/or organic second liquid to a desired level in the particles. Exemplary methods of secondary desiccation include vacuum drying with or without application of heat, lyophilization, fluidized bed drying, slurry spray drying, tray drying, belt drying, or air drying on a filter membrane.

In some embodiments, secondary desiccation is achieved by flowing a drying gas over a bed of particles atop a filtration element. In certain embodiments, the drying gas is helium, air, nitrogen or argon. In preferred embodiments, the drying gas is helium or air. The temperature, pressure, flow rate, or moisture content of the drying gas may be controlled during the drying time to achieve a desired rate of desiccation, a desired temperature difference relative to the glass transition temperature, or a desired equilibrium content of the aqueous first liquid or the organic second liquid at the conclusion of the secondary desiccation step. In other embodiments, the time required to achieve a desired level of desiccation is lower than that which corresponds to alternative secondary desiccation techniques, e.g., lyophilization, spray drying, or fluidized bed drying.

In other embodiments, the primary desiccation step, the washing step, and/or the secondary desiccation step are facilitated by modulating the temperature of particles relative to their glass transition temperature. Under certain conditions, quantities of the aqueous first liquid and the organic second liquid, the third liquid, and/or various components of the aqueous liquid droplets or particles, e.g., a surfactant, become trapped in a "glassy" matrix during particle formation (Richardson, H. et al., The European Physical Journal E, 12, no. 1 (2003): 87-91). In some embodiments, removal of various trapped liquids and particle components can be facilitated by bringing the temperature of the particle in proximity to the glass transition temperature for a period of time. Proximity to the glass transition enhances mobility within the particle and permits liberation of the trapped liquids and particle components at a substantially enhanced rate relative to what is typically seen at temperatures well below that of the transition temperature. With respect to the glass transition temperature, the temperature of the particles during step d) can be within about ±90° C., e.g., within about ±60° C., within about +30° C., within about +15° C., within about +10° C., or within about +5° C. The duration for which the particles are held in this proximity can vary as a function of the mobility of the liquid and particle component to be extracted and the conditions of extraction, e.g., the temperature, flow rate, and humidity of the drying gas, but can be from about 0 to about 24 hours, from about 0 to about 12 hours, from about 0 to about 6 hours, from about 0 to about 3 hours, from about 0 to about 1 hour, from about 0 to about 0.5 hours, from about 0 to about 0.25 hours, or from about 0 to about 0.1 hours.

As described herein, the particles have less than about 7% of moisture, e.g., water, by mass. In some embodiments, the particles have less than about 6% of moisture by mass. In other embodiments, the particles have less than about 5% of moisture by mass. In still other embodiments, the particles have less than about 3% of moisture by mass. In certain other embodiments, the particles have less than about 2% of moisture by mass. In preferred embodiments, the particles have less than about 1% of moisture by mass. In certain preferred embodiments, the particles are substantially free from any moisture by mass. In some embodiments, the particles have less than about 0.1% of moisture by mass. In some embodiments, the particles have less than about 0.01% of moisture by mass. Exemplary methods for the measurement of moisture content include chemical titration methods, e.g., Karl Fischer titration involving an oven. A variety of solvents, including water, may also be measured using weight loss methods involving thermal excitation. Exemplary methods include Thermogravimetric Analysis with Infrared Spectroscopy (TGA-IR) or Gas Chromatography Flame Ionization Detector Mass Spectrometry (GC-FID/MS).

Sterility is a critical facet of pharmaceutical compositions because it affects the safety with which the composition may be administered. For example, many particle formulations, particularly microparticle formulations, achieving sterility can be a challenge since common sterilization techniques, e.g., sterile filtration, are not compatible. Sterile filtration steps typically involve a membrane through which only those components of the filtered liquid which are, for example, 200 nm in size or smaller may pass. Particle formulations with solids greater than 200 nm in size are therefore filtered rather than sterilized. In some embodiments, formulations of the disclosure are subjected to an alternative process of terminal sterilization prior to use or administration. The effectiveness of these sterilization protocols and of the process in reducing bioburden may be assessed following regulatory guidelines, e.g., those listed in USP Chapter <71>, Ph. Eur. Chapter, Sterility: 2.6.1, 21 CFR 610.12, ICH Q4B ANNEX 8(R1), ICH Q5A, etc. Exemplary methods of demonstrating compliance include incubating about 1 mL of the drug product per container in an appropriate growth media (Soybean-Casein Digest Medium, Tryptic Soy Broth, Fluid Thioglycollate Medium)

for a period of about 14 days to ensure no microbial growth in about 1 in about 1000 million units of the drug product, or about 1 in about 1 million units of the drug product. As disclosed herein, a "sterile" formulation is aseptic or free from living microorganisms and their spores. In certain embodiments, the methods described herein, further comprises sterilization of the particles after the aqueous first liquid and organic second liquid is removed. In certain preferred embodiments, the sterilization occurs by irradiation, pasteurization, or freezing. In preferred embodiments, the irradiation is by gamma radiation. In certain preferred embodiments, the particles are produced aseptically.

In some embodiments, the terminal sterilization step involves gamma irradiation. In other embodiments, the sterilization step required to inactivate at least about 2-4 $\log_{10}$ of viral microbial contaminants is about 10 kGy, about 20 kGy, about 40 kGy, about 60 kGy, or about 100 kGy. In certain embodiments, the particles comprise an antioxidant or a scavenger to mitigate the harmful effects of any degradation products which are generated as a result of the sterilization step.

In other embodiments, the terminal sterilization step involves a transient thermal treatment. In some embodiments, the formulation is exposed to temperatures from about 60 to about 200° C., e.g., from about 60 to about 180° C., from about 60 to about 160° C., from about 60 to about 140° C., from about 60 to about 130° C., from about 60 to about 120° C., or from about 60 to about 110° C. In certain embodiments, the exposure occurs over a period from about 1 to about 144 hours, e.g., from about 1 to about 120 hours, from about 1 to about 100 hours, from about 1 to about 90 hours, from about 1 to about 72 hours, from about 1 to about 48 hours, from about 1 to about 36 hours, or from about 1 to about 24 hours. For example, dry heat sterilization can be performed at a temperature of about 80° C. for about 72 hours, about 160° C. for about two hours, or about 170° C. for about one hour. In certain other embodiments, pasteurization is performed at about 60° C. for about 10 hours.

In some embodiments, the sterilization is ensured by using beta radiation, X-ray sterilization, steam sterilization, solvent-detergent inactivation steps, supercritical $CO_2$ mediated sterilization, low pH holds, ultraviolet C exposure, or ethylene oxide mediated sterilization of the formulation. In other embodiments, the terminal sterilization step is performed at low temperatures from about −100 to about 60° C. In certain embodiments, the supercritical $CO_2$ further includes additives (e.g., hydrogen peroxide, water, acetic anhydride, and the like) intended to effectively inactivate microorganisms, including bacterial spores.

In other embodiments, the third liquid or fourth liquid is chosen such that its presence helps to facilitate process sterility. In some embodiments, the third liquid or fourth liquid is an antimicrobial or contains such a compound which is contained within the particle. This compound may persist inside the particles even after the secondary desiccation step. Organic liquids that can be used as a third liquid or fourth liquid with antimicrobial activity may include, but are not limited to acetates (e.g., ethyl acetate, butyl acetate) and alcohols (e.g., ethanol, phenol), or the like. The third liquid or fourth liquid may also contain antimicrobial excipients, e.g., phenolic substances, benzalkonium chloride, linalool, coumarin, peroxides, active chlorine, alkalis, or a combination thereof.

In some embodiments, the use of nano-filtration membranes for the inlet process streams, e.g., for use on the aqueous first liquid and organic second liquid prior to particle formation, may contribute to a reduction of the bio-burden on the process. In other embodiments, combinations of the preceding sterility measures are employed to reach appropriate bio-burden levels.

Control of Particle Properties

Properties of the particles can be controlled by modulating the drying rate of the aqueous liquid droplets, the Peclet numbers of the components of the aqueous liquid droplets, the concentrations of the components of the aqueous liquid droplets, or the particle formation. In certain embodiments, the modulation influences the size, morphology, density, porosity, composition, surface energy properties of the particles, and help to establish the distribution of components within the particles and to regulate important physicochemical properties which may be difficult to address when drying, e.g., in air, as with conventional spray drying.

The methods described herein, are generally provided for controlling the morphology of particles, the method comprising: a) providing an aqueous first liquid comprising a therapeutic biologic; b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic, wherein the Peclet number of the mixture determines the morphology of the particles; c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture.

In one aspect, the disclosure provides a method of controlling the morphology of particles, the method comprising: a) providing an aqueous first liquid comprising a therapeutic biologic; b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic, wherein the Peclet number of the mixture determines the morphology of the particles; c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture. As disclosed herein, the therapeutic biologic may be an antibody, antibody fragment, bovine serum albumin (BSA), or human serum albumin (HSA). In certain embodiments, the therapeutic biologic in the particles has an activity per unit of about 0.5 to about 1.0. In certain preferred embodiments, the therapeutic biologic is antibody. In preferred embodiments, the therapeutic biologic in the particles has an activity per unit of about 0.8 to about 1.0.

In certain embodiments, the particles include less than 10% internal void spaces, less than 5% internal void spaces, less than 1% internal void spaces, or less than 0.5% internal void spaces after removing the aqueous first liquid and organic second liquid from the mixture. In preferred embodiments, the particles are substantially free from any internal void spaces after removing the aqueous first liquid and organic second liquid from the mixture.

In other embodiments, the circularity of the particles is from about 0.85 to about 1.00 after removing the aqueous first liquid and organic second liquid from the mixture. In still other embodiments, the circularity of the particles is from about 0.90 to about 1.00 after removing the aqueous first liquid and organic second liquid from the mixture. In certain other embodiments, the circularity of the particles is from about 0.95 to about 1.00 after removing the aqueous first liquid and organic second liquid from the mixture. In preferred embodiments, the circularity of the particles is from about 0.98 to about 1.00 after removing the aqueous first liquid and organic second liquid from the mixture.

In some embodiments, the aqueous first liquid and organic second liquid further comprises a plasticizer that controls the morphology of the particles. Exemplary plasticizers include sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 80, diethyl phthalate and other phthalate derivatives, castor oil, triacetin, water, chlorpheniramine, 1-butyl-3-methyl imidazolium dioctyl sulfosuccinate, hexyl acetate, water, 2-ethylhexyl acetate, triethyl citrate, dibutyl sebacate, benzyl alcohol, benzyl benzoate, dimethylacetamide, various aqueous liquids, organic liquids, oils, ionic liquids, polysaccharides, sugars, diols, polyols, fatty acids, fatty acid esters, esters, surfactants, or a combination thereof. In certain embodiments, the plasticizer is sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 20, polysorbate 60, polysorbate 80, fatty acid ester of sorbitol, diethyl phthalate and other phthalate derivatives, castor oil, triacetin, water, chlorpheniramine, 1-butyl-3-methyl imidazolium dioctyl sulfosuccinate, hexyl acetate, 2-ethylhexyl acetate, triethyl citrate, dibutyl sebacate, benzyl alcohol, benzyl benzoate, dimethylacetamide, or a combination thereof. In preferred embodiments, the plasticizer is polysorbate 20, polysorbate 60, or polysorbate 80. In certain preferred embodiments, the plasticizer is polysorbate 20 or polysorbate 80. In certain other embodiments, the fatty acid ester of sorbitol is a sorbitan ester, e.g., span 20, span 40, span 60, or span 80.

The morphology of the particle can be an important factor for certain applications in particle formation, as described herein. For example, in order to minimize the viscosity of a suspension formulation at a given particle concentration, it can be advantageous to minimize the degree to which the particles comprise internal void spaces (e.g., porosity) or exhibit irregular shapes.

In some embodiments, the continuous process of step b), comprises continuous membrane emulsification, continuous homogenization, continuous mechanical stirring, continuous mechanical shaking, continuous impinging jet mixing, continuous ultra-sound, continuous sonication, continuous micro-channel emulsification, continuous microsieve emulsification, continuous capillary extrusion, continuous static mixing, or a combination thereof. In certain embodiments, the continuous micro-channel emulsification is accomplished using a microfluidic chip based device. In other embodiments, the continuous process of step b), comprises continuous membrane emulsification, continuous homogenization, continuous impinging jet mixing, continuous static mixing, or a combination thereof. In certain other embodiments, the continuous membrane emulsification is conducted by rotating membrane emulsification, cross-flow membrane emulsification, or a combination thereof. In still other embodiments, the continuous homogenization is conducted by shear homogenization, pressure homogenization, rotor-stator homogenization, microfluidization, or a combination thereof. In certain embodiments, the continuous mechanical stirring is conducted by a turbulent stirred vessel, a magnetic stirring device, a mechanical stirring device, or a combination thereof. In certain preferred embodiments, the continuous static mixing comprises laminar flow, turbulent flow, transition flow, or a combination thereof.

As described herein, the Peclet number of the mixture is regulated to control the particle morphology. The term "Peclet number" refers to the ratio of the rate of a solvent mass transport process outside of a droplet or particle to the rate of a solute mass transport process inside a droplet or particle. Exemplary Peclet numbers as described herein, during the drying period are about 1 or less, indicating a regime where transport of solutes within the drop is fast as compared to the radial velocity of the receding droplet surfaces. Such Peclet numbers tend to correlate with regular, circular particle morphologies. For Peclet numbers of about 1 or greater, the droplet surface tends to move fast in relation to the solutes, thereby leading to an enriched layer of solute near the surface of the drop. Situations of this type typically correlate with irregular particle morphologies, i.e., morphologies which are less smooth, less circular, and/or more porous than those associated with lower Peclet numbers. Such morphologies may comprise raisin-like features (high roughness) and/or increased internal void space. The Peclet number of the mixture can be regulated in several different ways using various properties of the aqueous first liquid and organic second liquid. Such properties include the solubility of the aqueous first liquid in the organic second liquid as well as the initial saturation level of the organic second liquid. Furthermore, the diffusivity of the aqueous first liquid and organic second liquid may be controlled. Parameters which influence these properties include the temperature, viscosity, and/or polarity of the aqueous first liquid and/or the organic second liquid, as well as the surface tension at the interface between the aqueous first liquid and the organic second liquid. In certain embodiments, the organic second liquid is a mixture of two or more liquids of different polarities.

As disclosed herein, each component of the droplet/particle method is defined by its own Peclet number. These tend to be smaller for smaller molecules, e.g., excipients, and larger for larger molecules, e.g., proteins. In some embodiments, the Peclet number of the mixture of step b) is less than about 500. In other embodiments, the Peclet number of the mixture of step b) is less than about 10. In certain embodiments, the Peclet number of the mixture of step b) is less than about 5. In still other embodiments, the Peclet number of the mixture of step b) is less than about 3. In certain other embodiments, the Peclet number of the mixture of step b) is less than about 2. In preferred embodiments, the Peclet number of the mixture of step b) is less than about 1. The Peclet number can be calculated by methods known to one skilled in the art.

In other embodiments, the aqueous liquid droplets in the mixture of step c) are dehydrated after contact with the organic second liquid of step b). In some embodiments, the dehydration of the aqueous liquid droplets in the mixture of step c) occurs in a continuous drying tube, a continuous drying vessel, or a combination thereof. In certain other embodiments, the continuous drying tube is further connected to at least one continuous process. In still other embodiments, the continuous drying vessel is further connected to at least one continuous process. In certain embodiments, the continuous drying vessel comprises continuous mechanical stirring. In certain preferred embodiments, the continuous mechanical stirring is conducted by a turbulent stirred vessel, a magnetic stirring device, or a mechanical stirring device. In some embodiments, the average residence time T of the particles in the continuous drying vessel and the relationship between this time and the characteristic particle formation time t* is considered in the design and sizing of the continuous drying vessel. In some embodiments, the average residence time can be estimated as τ=V/Q, where V is the volume of the continuous drying vessel and Q is the volumetric flow rate of product through it. In some embodiments, the particle resides in the continuous drying vessel for about 0 to about 10,000 seconds, e.g., about 0 to about 5,000 seconds, 1,000 seconds, 500 seconds, 400 seconds, 300 seconds, 200 seconds, 100 seconds, 90 seconds, 80 seconds, 70 seconds, 60 seconds, 50 seconds, 40 seconds, 30 seconds, 20 seconds, 10 seconds, 9 seconds, 8 seconds, 7 seconds, 6 seconds, 5 seconds, 4 seconds, 3 seconds, 2 seconds, or 1 second. In some embodiments, the ratio of the characteristic particle formation time to the average residence time t*/τ is a figure of merit. In some embodiments, the ratio of the characteristic particle formation time to the average residence time is about 0 to about 100, e.g., 0 to about 100, 50, 25, 10, 5, 4, 3, 2, 1, 0.9, 0.8, 0.7, 0.6, 0.5, 0.4, 0.3, 0.2, or 0.1.

In certain embodiments, the temperature of the aqueous first liquid and organic second liquid can be controlled. The aqueous first liquid and organic second liquid can may be kept at the same temperature or at different temperatures. In other embodiments, the temperature of each liquid is, independently, from about −100 to about 200° C., e.g., from about −20 to about 180° C., from about 0 to about 100° C., from about 0 to about 50° C., from about 0 to about 40° C., from about 0 to about 30° C., from about 0 to about 20° C., from about 0 to about 10° C., or from about 0 to about 5° C. In preferred embodiments, the temperature of each liquid is from about 0 to about 30° C., from about 0 to about 10° C., or from about 0 to about 5° C.

In some embodiments as described herein, step c) further comprises decreasing the temperature of the organic second liquid to a temperature within about 30° C. of the freezing point of the aqueous first liquid. In other embodiments, the boiling point of the organic second liquid at atmospheric pressure is from about 0 to about 200° C. In certain embodiments the temperature, pressure, and water content of the organic second liquid, in which the aqueous liquid droplets are dispersed can be regulated to control the dehydration kinetics.

In other embodiments, the viscosity of the aqueous first liquid and organic second liquid can be controlled. In some embodiments, the viscosity of the aqueous first liquid and organic second liquid affects a coefficient of diffusion or dispersal of the aqueous first liquid in the organic second liquid, thereby regulating the drying rate and Peclet number. The viscosity of each liquid may be, independently, from about 0.01 mPa·s to about 10,000 mPa·s, e.g., from about 0.01 to about 1,000 mPa·s, from about 0.01 to about 100 mPa·s, from about 0.01 to about 50 mPa·s, from about 0.01 to about 25 mPa·s, from about 0.01 to about 10 mPa·s, from about 0.01 to about 5 mPa·s, or from about 0.01 to about 1 mPa·s. Methods of controlling viscosity may include temperature regulation and viscosity modifying additives, e.g., polymers. Mixtures of liquids may also be used to control viscosity.

In some embodiments, the solvent polarity of the aqueous first liquid and organic second liquid is controlled. In other embodiments, the aqueous first liquid has a dielectric constant from about 1 to about 200, e.g., from about 1 to about 180, from about 10 to about 140, from about 30 to about 120, from about 50 to about 100, or from about 70 to about 80. In still other embodiments, the organic second liquid has a dielectric constant from about 1 to about 200, e.g., from about 1 to about 10, from about 1 to about 80, from about 1 to about 50, from about 1 to about 40, from about 1 to about 30, from about 1 to about 20, from about 1 to about 10, from about 1 to about 7, from about 1 to about 5, or from about 1 to about 3. Mixtures of various liquids may be used to control polarity.

In other embodiments, the surface tension at the interface between the aqueous first liquid and organic second liquid is controlled. In some embodiments, the surface tension is from about 0 to about 100 mN/m, e.g., from about 0 to about 70 mN/m, from about 0 to about 60 mN/m, from about 0 to about 50 mN/m, from about 0 to about 40 mN/m, from about 0 to about 30 mN/m, from about 0 to about 20 mN/m, from about 0 to about 10 mN/m, from about 0 to about 9 mN/m, from about 0 to about 8 mN/m, from about 0 to about 7 mN/m, from about 0 to about 6 mN/m, from about 0 to about 5 mN/m, from about 0 to about 4 mN/m, from about 0 to about 3 mN/m, from about 0 to about 2 mN/m, or from about 0 to about 1 mN/m.

In some embodiments, the organic second liquid is a mixture of two or more liquids. In other embodiments, the mixture is used to tune the viscosity and/or polarity of the organic second liquid. In certain embodiments, the mixture is used to tune the solubility of the aqueous first liquid in the organic second liquid. Since such properties can affect the rate and Peclet number associated with the continuous dehydrating process, they may be used to directly control various particle properties (e.g., size, morphology, density, etc.) through simple adjustment of the relative ratios of the liquids comprising the mixture. For example, a mixture for which the aqueous first liquid is more soluble in one component (Component A) than the other (Component B). In certain other embodiments, increasing the relative quantify of Component B can yield particles which are smoother, more spherical, and/or less porous than what would otherwise be achievable using only Component A. In still other embodiments, for mixtures, one liquid in the mixture has a concentration from about 0 to about 99.9999 vol %, e.g., from about 0 to about 99 vol %, from about 0 to about 95 vol %, from about 0 to about 90 vol %, from about 0 to about 75 vol %, from about 0 to about 50 vol %, from about 0 to about 25 vol %, from about 0 to about 10 vol %, from about 0 to about 5 vol %, from about 0 to about 1 vol %, or from about 0 to about 0.0001 vol %. Exemplary mixtures include, but are not limited to benzyl benzoate/acetone (e.g., about 5-30% benzyl benzoate, such as about 5:95, about 10:90, about 15:85, about 20:80, about 25:75, or about 30:70), isopropyl alcohol/sesame oil (e.g., about 35-65% isopropyl alcohol, such as about 35:65, about 40:60, about 45:55, about 50:50, about 55:45, about 60:40, or about 65:35), hexanes/ethanol (e.g., about 10-35% hexanes, such as about 10:90, about 15:85, about 20:80, about 25:75, about 30:70, or about 35:65), toluene/acetonitrile (e.g., about 10-35% toluene, such as about 10:90, about 15:85, about 20:80, about 25:75, about 30:70, or about 35:65), cottonseed oil/butyl acetate (e.g., about 10-35% cottonseed oil, such as about 10:90, about 15:85, about 20:80, about 25:75, about 30:70, or about 35:65), toluene/ethyl acetate (e.g., about 10-35% toluene, such as about 10:90, about 15:85, about 20:80, about 25:75, about 30:70, or about 35:65), diethyl ether/isopropanol (e.g., about 5-30% diethyl ether, such as about 5:95, about 10:90, about 15:85, about 20:80, about 25:75, or about 30:70), tetrahydrofuran/pentane (e.g., about 35-65% THF, such as about 35:65, about 40:60, about 45:55, about 50:50, about 55:45, about 60:40, or about 65:35), safflower oil/methanol (e.g., about 25-55% safflower oil, such as about 25:75, about 30:70, about 35:65, about 40:60, about 45:55, about 50:50, or about 55:45), and lime oil/acetone (about 5-30% lime oil, such as about 5:95, about 10:90, about 15:85, about 20:80, about 25:75, or about 30:70). As described herein, choosing the appropriate liquid combinations and ratios, e.g., components of the organic second liquid, can control the particle drying speed and Peclet number.

In other embodiments, the mixture comprising the organic second liquid further includes a surfactant. In some embodiments, the surfactant helps to establish an interface between the aqueous first liquid and organic second liquid, and in other embodiments, to regulate the continuous drying speed and Peclet number. In certain embodiments, the surfactant limits coalescence of the aqueous liquid droplets during the continuous drying process and/or mitigates damage to the therapeutic biologic, e.g., an antibody, antibody fragment, bovine serum albumin (BSA), or human serum albumin (HSA), at the interface between the aqueous first liquid and the organic second liquid. The concentration of the surfactant in the organic second liquid ranges from about 0 to about 100 vol %, e.g., from about 0 to about 50 vol %, from about 0 to about 25 vol %, from about 0 to about 10 vol %, from about 0 to about 5 vol %, from about 0 to about 1 vol %, from about 0 to about 0.1 vol %, from about 0 to about 0.01 vol %, from about 0 to about 0.001 vol %, or from about 0 to about 0.0001 vol %. Exemplary mixtures of organic second liquid and surfactant include, but are not limited to Polysorbate 80/ethyl acetate (e.g., about 0.5:99.5, such as about 0.1:99.9, about 1:99, about 2.5:97.5, about 5:95, about 10:90, about 20:80), Span 20/ethyl acetate (about 0.5:99.5, such as about 0.1:99.9, about 1:99, about 2.5:97.5, about 5:95, about 10:90, about 20:80), Polysorbate 20/ethyl acetate (e.g., about 0.5:99.5, such as about 0.1:99.9, about 1:99, about 2.5:97.5, about 5:95, about 10:90, about 20:80), Polysorbate 80/butyl acetate (e.g., about 0.5:99.5, such as about 0.1:99.9, about 1:99, about 2.5:97.5, about 5:95, about 10:90, about 20:80), Polysorbate 80/isopropanol (e.g., about 0.5:99.5, such as about 0.1:99.9, about 1:99, about 2.5:97.5, about 5:95, about 10:90, about 20:80), or Polysorbate 80/cottonseed oil/ethyl acetate (e.g., about 0.5:20:79.5, such as about 0.1:20:79.9, about 1:30:69, about 2.5:10:87.5, about 5:5:90, about 10:5:75, about 20:20:60).

Effective plasticization requires the use of a plasticizer in the aqueous first liquid or organic second liquid at a temperature at about or higher than the glass transition temperature of the particle or protoparticle during particle formation. Controlling the temperature of the particle or protoparticle during the continuous particle formation process can be achieved by controlling the temperature of the aqueous first liquid and organic second liquid. Effective plasticization can be achieved to obtain a smoother, more circular, and less porous particle morphology in instances where a component of the aqueous first liquid, e.g., a therapeutic biologic, is typified by a Peclet number greater than 1, and where the absence of effective plasticization would otherwise lead to particle morphologies which are more characteristic of high Peclet number processes.

In some embodiments, various aqueous liquids, organic liquids, oils, ionic liquids, polysaccharides, sugars, diols, polyols, fatty acids, fatty acid esters, esters, surfactants, or a combination thereof, are employed as effective plasticizers under appropriate processing conditions. Exemplary plasticizers include, but are not limited to sucrose, xylitol, sorbitol, fructose, triglyceride, pectin, glycerol, triethylcitrate, ethyl acetate, citric acid, oleic acid, hydroxypropyl cellulose, methyl pyrrolidone polyethylene glycol, polypropylene glycol, polysorbate 80, diethyl phthalate or other phthalate derivatives, castor oil, triacetin, water, chlorpheniramine, 1-butyl-3-methyl imidazolium dioctyl sulfosuccinate, hexyl acetate, water, 2-ethylhexyl acetate, triethyl citrate, dibutyl sebacate, benzyl alcohol, benzyl benzoate, dimethylacetamide, or a combination thereof.

Like plasticization, increasing the total solute load of the aqueous first liquid can be useful for achieving smoother, more spherical, and less porous particles in instances where the dynamics of continuous particle formation are such that surface roughness may be likely to prevail at the nominal solute concentration. Similarly, decreasing the solute load of the aqueous first liquid can be leveraged to induce or encourage buckling when it might not otherwise prevail at the nominal solute load.

Control of the methods described herein, may be useful for achieving low Peclet numbers even in instances where a component or components of the aqueous first liquid, e.g., the therapeutic biologic, are characterized by having low diffusivity. In some embodiments, low Peclet numbers is achieved when the diffusivity of the component is from about 0 to about 10,000 $\mu m^2/s$, e.g., from about 0 to about 1,000 $\mu m^2/s$, from about 0 to about 100 $\mu m^2/s$, from about 0 to about 50 $\mu m^2/s$, from about 0 to about 25 $\mu m^2/s$, from about 0 to about 10 $\mu m^2/s$, from about 0 to about 5 $\mu m^2/s$, from about 0 to about 2.5 $\mu m^2/s$, or from about 0 to about 1 $\mu m^2/s$.

The disclosure generically described, will be more readily understood by reference to the following examples, which are included merely for purposes of illustration of certain aspects and embodiments of the present disclosure, and are not intended to be limiting.

EXEMPLIFICATION

Abbreviations

A angstrom
aa amino acids
BA butylacetate
agg aggregation
AU arbitrary units
BIgG bovine IgG
BSA bovine serum albumin
° C. degrees Celsius
cm centimeter
conc. concentration
cP centipoise
CP continuous phase
d day
DI deionized
DP dispersed phase
EA ethylacetate
ELISA enzyme-linked immunosorbent assay
EO ethyloleate
eq. equivalent
Et ethyl
eV electron-volts
FDS filtered drug substance
g gram
GC gas chromatography
h hour
HDPE high-density polyethylene hIgG human IgG
HPLC high performance liquid chromatography
hr hour
HSA human serum albumin
ID internal diameter
IV intravenous
K thousand
KF Karl Fischer
kJ kilojoules
kPa kiloPascal
kV kilovolts
L liter
LC-MS liquid chromatograph mass spectrometry
LD laser diffraction
Lyo lyophilization
m meta
mAb monoclonal antibody
MALDI-MS matrix-assisted laser desorption ionization mass spectrometry
Me methyl
min minute
μg microgram
μL microliter
μm micrometer
μM micromolar
mg milligram
mL milliliter
mm millimeter
mM millimolar
MOC micro-orifice collector
mol mole
mPa·s milliPascal second
mTorr milliTorr
N newton
nBA n-butylacetate
nm nanometer
p para
PBS phosphate-buffered saline
PC phosphatidylcholines
PEG polyethylene glycol
PI pressure indicator
ppm parts per million
PS 80 polysorbate 80
PTFE polytetrafluoroethylene
ref relative centrifugal force
RH relative humidity
rpm revolutions per minute
rsm rotor-stator mixer
RT room temperature
s second
SC subcutaneous
sec second
SEM scanning electron microscopy
SLPM standard liter per minute
t tertiary
tert tertiary
UHMW ultrahigh molecular weight polyethylene
ug micrometer
UTW ultra thin wall
UOM unit of measure
UV ultraviolet
VIS visible

Materials

Human IgG (IRHUGGF-LY, >97%) and bovine IgG (IRBVGGF) were obtained from Innovative Research as a powder or as an aqueous solution. Bovine serum albumin (BSA) and human serum albumin (HSA) were purchased from Sigma-Aldrich. The monoclonal antibodies (mAb) were provided and received as an aqueous solution. A biosimilar of Roche's Rituximab was purchased from a vendor that provided the antibody in an aqueous composition consistent with the FDA-label defined as 10 mg/mL rituximab, 9 mg/mL sodium chloride, 7.35 mg/mL sodium citrate dihydrate, and 0.7 mg/mL polysorbate 80. A biosimilar of Roche's trastuzumab was purchased from Genscript Biotech Corporation that provided the antibody in an aqueous composition consistent with the FDA-label. Composition of custom "feed solutions" used for processing particles were produced through modifying the received formulation by desalting followed by concentrating and adding desired excipients or by direct buffer exchange. All excipients used in particle composition have been used in existing approved biologics injections. Concentration columns were procured from Millipore Sigma (Amicon® Ultra 15 mL Filters for Protein Purification and Concentration with a 3 kDa cut off) and used where necessary to: (i) reach the desired monoclonal antibody concentration, and (ii) exchange buffer/excipients before particle formation. Zeba desalting columns (Thermo Fisher Scientific 87773) were also used to remove salt from solutions in certain instances. Typically, the ratio of residual salt to therapeutic biologic in the desalted solutions (wt/wt) was <1% as determined form conductivity measurements and/or elemental analysis. All excipients were purchased from Sigma-Aldrich and used as received.

Desiccation liquids, e.g., organic second liquids or third liquids, including benzyl benzoate, various alcohols, various acetates, oils, ionic liquids, surfactants, and aqueous media comprising different forms of polyethylene glycol (PEG) were used as appropriate. All desiccation liquids, e.g., acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, except for the ionic liquids were purchased from Sigma Aldrich and used as received. The ionic liquids were purchased from TCI America and used as received.

Methods

Particle Formation:

Unless otherwise noted, membrane emulsification, homogenization, mechanical stirring, mechanical shaking, impinging jet mixer, ultra-sound, sonication, micro-channel emulsification, microsieve emulsification, capillary extrusion, static mixing, or a combination thereof, was used for continuous droplet formation and continuous dehydration. A Harvard Apparatus Model 33 dual-channel syringe pump was utilized for pumping the feed solution (DP). Peristaltic pumps and piston pumps have also been deployed. The aqueous liquid droplets generated in the organic second liquid were collected for desiccation by a vessel, typically under conditions of continuous stirring. In the case of a static mixer, the droplets underwent desiccation during flow in a 50 ft tube to produce particles that are collected on a filter. Thermal management of the organic second liquid was utilized in the preparation of select examples.

Image Analysis: Particle diameters and circularity were measured using ImageJ analysis on SEM images. The analysis was performed on, for example, at 500× or 1000× images. The ImageJ Particle Analysis tool was run on the image, identifying objects with a circularity of >0.8 and size >0.5 um with each object outlines. These outlines were visually inspected for good fit. Any mis-identified particles were manually rejected and any missed particles were manually included and measured using the ImageJ diameter tool. Select microscopy images were chosen for further analysis on the basis of (i) minimal particle overlapping, (ii) good contrast between the particles and the background, and (iii) a resolution providing for particle occupancies of at least 10 pixels. This allowed for particles to be easily identified and reduced resolution-based error. A binary threshold was applied to separate the particles from background, and a watershed segmentation algorithm was applied to ensure that individual particles were measured separately. The ImageJ tool "Analyze Particles" was then applied on the binary picture with the following parameters: circularity between 0.5 and 1.0; size between 5 and infinity square microns; exclude on edges; fill holes. The outlines of the identified particles were overlaid onto the original image. Particles which were misidentified, such as clusters that were identified as a single particle or particles whose outlines do not match the particle, were then discarded. Missing particles were measured by manually tracing the particle's outline and using ImageJ's Measure tool.

Accelerated Storage Protocol:

All samples were transferred to Wheaton E-Z ex-traction round-bottom glass vials for aging (typically 2 mL or 4 mL volume, depending on sample). The glass vials were sealed with parafilm, placed in an oven at 4° C., 25° C., or 40° C., and visually inspected over the aging period to ensure integrity and stability.

Particle Dissolution:

Phosphate-buffered saline (PBS) or water was added to dry particle samples to produce a final concentration of 10 mg/mL (particle mass/mL of solution). Samples were placed on a VWR angular rocker with a speed setting of "35" and angle setting of "15". At 1, 10, 20, 30, 40, 50, 60, 90, and 120 minutes a 10 µL aliquot was removed from the sample vial and the absorbance at 280 nm was measured and recorded. The mAb concentration was plotted against time for all samples.

Size Exclusion Chromatography (SEC) Measurements:

The quantification of size variants in select samples was determined by size exclusion chromatography. The analysis utilized an AdvanceBio SEC-3 column, 7.8 mm ID×30 cm, 3 µm (Agilent) run on an HPLC system (1260 Infinity II, Agilent). The mobile phases were 25 mM potassium phosphate and 0.25 M potassium chloride at pH 6.8. The chromatography was run isocratically at a flow rate of 1.0 mL/min for 15 minutes. The column temperature was maintained at ambient temperature and the eluent absorbance was monitored at 280 nm. Monoclonal antibodies were diluted with its respective formulation buffer to 1 mg/mL. The injection volume was 10 µL. 20 µL Injections of samples (1 mg/mL) were run at a flow rate of 1 mL/min in SEC buffer (25 mM phosphate, 250 mM NaCl pH 6.8) for 15 minutes on an Agilent AdvanceBio SEC (300 mm×2.7 um, 300 Å column). Peak analysis was performed by auto-integrating using the following parameters: slope sensitivity=0.5, peak width=0, height reject=0, area reject=0, shoulders off, area percent reject 0, standard tangent skim mode, advanced baseline correction, 0 for front peak skim height ratio, 0 for tail peak skim height ratio, 0 for peak to valley ratio, and 0 for skim valley ratio. Alternatively, 20 µL injections of samples (1 mg/mL) were run at a flow rate of 1 mL/min in SEC buffer (25 mM phosphate, 250 mM NaCl pH 6.8) for 15 minutes on an Agilent AdvanceBio SEC (300 mm×2.7 um, 300 Å column). Peak analysis was performed by auto-integrating using the following parameters: slope sensitivity=0.5, peak width=0, height reject=0, area reject=0, shoulders off, area percent reject 0, standard tangent skim mode, advanced baseline correction, 0 for front peak skim height ratio, 0 for tail peak skim height ratio, 0 for peak to valley ratio, and 0 for skim valley ratio.

Scanning Electron Microscopy (SEM):

Electron micrographs were collected for select samples with either a Hitachi TM3030Plus or a TM1000 tabletop microscope. The samples were immobilized on conductive tape and examined in a low-vacuum anti-charging environment, obviating the need for sample preparation.

Subvisible Particle (SvP) Analysis:

Subvisible particles (SvPs) were analyzed with a Fluid Imaging Technologies FlowCam PV-100 system. Samples for analysis were reconstituted in sterile centrifuge tubes with filtered water (Milli-Q) to the concentration of interest. Three sets of samples were investigated thereafter. These included (i) a sample of the diluent used for reconstitution, (ii) an aliquot of the feed solution used for the particle formation process, i.e., a sample of the aqueous first liquid, and (iii) the reconstituted material.

Dynamic Scanning Calorimetry (DSC):

Powdered samples were analyzed using dynamic scanning calorimetry. Masses of 5 to 10 mg of powdered samples were loaded into aluminum crucibles and sealed hermetically. Crucibles were loaded into the instrument, and the heat flow into the samples was monitored while the temperature was ramped from −80-200° C., optionally, from 20-180° C., at a constant rate of 5° C./minute.

USP <790>:

According to the USP <790> standard, samples of dissolved particles were visually observed against a white and black background under lighting conditions greater than 2000 lux. Matte-finished high density polyethylene sheets were selected for the background to reduce glare. The illuminance at the viewing point was confirmed with a lux meter (Dr. Meter, LX1330B). The samples were swirled before being held up to the backgrounds and viewed for 5 sec.

EXAMPLES

The methods disclosed herein, have been utilized in separate instances to prepare particles including at least one of several therapeutic biologics, e.g., whole human IgG or bovine IgG, or one of several monoclonal antibodies, e.g., Rituximab and Trastuzumab, or bovine serum albumin (BSA), or human serum albumin (HSA) and can be scaled to produce particles up to 20 grams. Various analytical techniques were applied to assess the physical characteristics of the particles themselves as well as the structural and functional properties of the processed therapeutic biologics.

Figure 3:
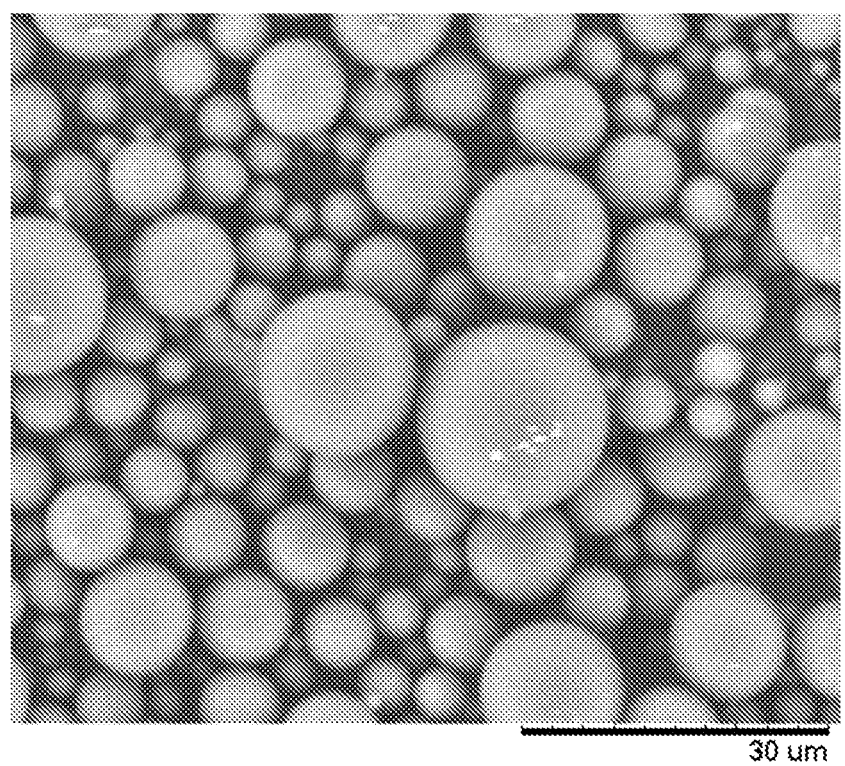
FIG. 3 shows an image of particles comprising bovine IgG and excipients that were obtained by rotor stator mixing using methods of the disclosure. Scale bar is 30 μm.

Scanning electron microscopy and associated image analysis were used to study the particle morphology and size distribution, respectively. Various morphologies and distributions of components were achieved by controlling the properties of the aqueous first liquid and organic second liquid. In some instances, the processing conditions conferred smooth particles of high sphericity and/or facile control of the mean particle size over a broad range with low dispersity. The functional properties of the therapeutic biologics were also preserved, as evidenced by ELISA and binding assays performed on reconstituted material. This was corroborated by size exclusion HPLC analysis indicating that the process had a minimal or even remedial effect on the degree of inter-antibody association. Finally, investigation of the insoluble particle populations upon reconstitution revealed very few insoluble artifacts, particularly as compared to alternative particle formation procedures.

Example 1

Continuous static mixing for droplet generation and dehydration was generally carried out using a ⅛" Kenics static mixer. The static mixer was connected downstream of a tee-connector (outlet). The two inlet ports connected to a line pumping the aqueous drug substance (first liquid, HIgG, excipients) and a line pumping the organic second liquid. The solvent used was tert-methyl butyl ether and this was pumped at a flow rate of 400 mL/min. The aqueous feed was pumped at 2 mL/min. The two liquids met in the tee-connector and flowed through the static mixer where droplets of aqueous drug substance formed. The droplet containing organic solvent was released into a beaker(s) where droplets continued to dehydrate. Particles could be collected by vacuum filtration thought a 1 micron PTFE filter. Particles were then dried in vacuo to remove residual moisture. SEM images revealed identifiable circular and smooth particulate matter with a scale bar at 30 μm as shown in FIG. 1. The average circularity was calculated to be approximately 0.92.

Example 2

Continuous static mixing for droplet generation and dehydration was generally carried out using a ⅛" Kenics static mixer. The static mixer was connected downstream of a tee-connector (outlet). The two inlet ports connected to a line pumping the aqueous drug substance (first liquid, HIgG, excipients) and a line pumping the organic second liquid. The solvent used was butyl acetate and this was pumped at a flow rate of 400 mL/min. The aqueous feed was pumped at 2.0 mL/min. The two liquids met in the tee-connector and flowed through the static mixer where droplets of aqueous drug substance formed. The droplet containing organic solvent flowed through a 50 ft tube (e.g., 3/16" inner and ¼" outer diameter) and exited as dehydrated particles. These particles were collected into a beaker and subsequently centrifuged out, or optionally directly on a filter. Once the supernatant was removed the particles were dried in vacuo for 24 hrs. SEM images revealed identifiable circular and smooth particulate matter similar to Example 1.

Example 3

A procedure similar to Example 1 was employed. A ⅜" X-grid static mixer was used and the protein in the aqueous first phase was bovine serum albumin (100 mg/mL) and optionally, excipients. The second organic phase was butyl acetate. The aqueous first phase had a flow rate of 7 mL/min and the organic second phase at 1400 ml/min. SEM images revealed identifiable circular and smooth particulate matter ~10 microns as shown in FIG. 2. The average circularity was calculated to be approximately 0.93.

Example 4

A procedure similar to Example 1 was employed. The aqueous first phase contained a monoclonal antibody at ~45 mg/mL, tween 80 surfactant (~0.5 mg/mL), histidine buffer (~1.5 mg/mL), and an amino acid (~20 mg/mL). The resulting particles were largely spherical and had a turbidity similar to that of the aqueous first liquid. SEC data demonstrated the percentage of aggregates to be within 1% of the aqueous first liquid and the morphology of the particles were similar to Example 1.

Example 5

A PEEK Y connector assembly (0.04 inch) from IDEX (USA) was connected with tubing to a aqueous first phase (containing human IgG, optionally, excipients surfactant, buffer, amino acid), a continuous phase (n-butyl acetate), and an outlet tube. The two phases were mixed in the Y-connector assembly by pumping for 30 seconds at a flow rate of: aqueous phase=0.5 mL/min:organic phase=200 mL/min. The resulting droplets was continuously made as long as the two liquids were fed into the system. The resulting emulsion was sprayed into a stirred beaker and the aqueous droplets dehydrated over ~20 s. Particles we continuously siphoned off and filtered using vacuum filtration. The resulting particles were then dried by flowing dry air over them at a flow rate of 2 SLPM for 2 hrs. SEM images revealed identifiable circular and smooth particulate matter similar to Example 1.

Example 6

An IKA T25 rotor stator mixer was inserted into a 2 L PTFE beaker containing butyl acetate. The mixer was set to 10000 (up to 25000) rpm. 10 mL of aqueous liquid containing the drug substance (HIgG, BSA, HSA or antibody) was added rapidly to the beaker. Optionally, the aqueous liquid contains one or more, surfactant (e.g., tween 80, PS80), buffer (e.g., histidine, acetate, phosphate), amino acid (e.g., arginine, proline), salt (e.g., NaCl), and carbohydrate (e.g., trehalose, HP-β-cyclodextrin, sucrose, mannitol, sorbitol). After 30 s of mixing droplets were formed with the appropriate size and dispersity. The droplets were allowed another 30 s to dehydrate further before the suspension was pumped out of the beaker onto a filtration membrane. The same beaker was then again primed with more butyl acetate and the process repeated in a semi-continuous process. Filtered particles were dried in vacuo for 24 hrs and had a D50 of ~10 microns according to laser diffraction and a span ~1.0. SEM image revealed identifiable circular and smooth particulate matter with a scale bar at 30 μm as shown in FIG. 3. The average circularity was calculated to be approximately 0.95 with low turbidity and no extrinsics observable by VP and SvP analysis.

Example 7

Particles were prepared as described in Example 6. However, particles were not filtered but spray dried from the wet organic second liquid using a bench top spray drier. SEM image revealed identifiable circular and smooth particulate matter similar to FIG. 3, with low turbidity and no extrinsics observable by VP and SvP analysis.

Example 8

Figure 4:
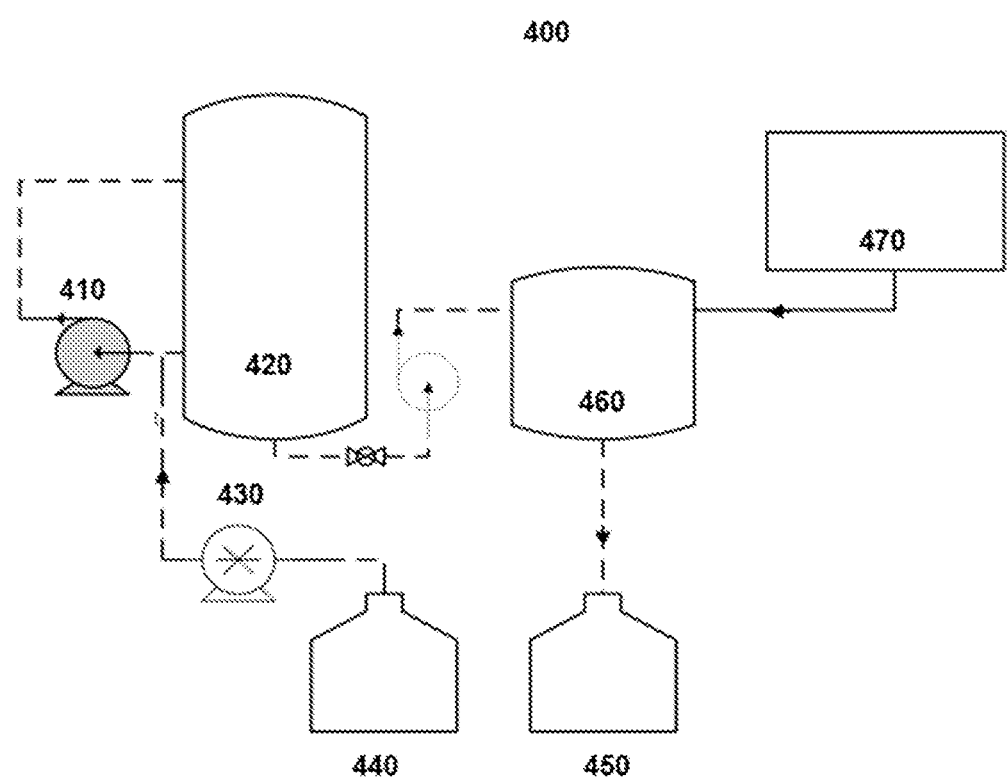
FIG. 4 shows a diagram of an exemplary inline homogenization system used to obtain particles comprising Ab and excipients through methods of the disclosure.
Figure 5:
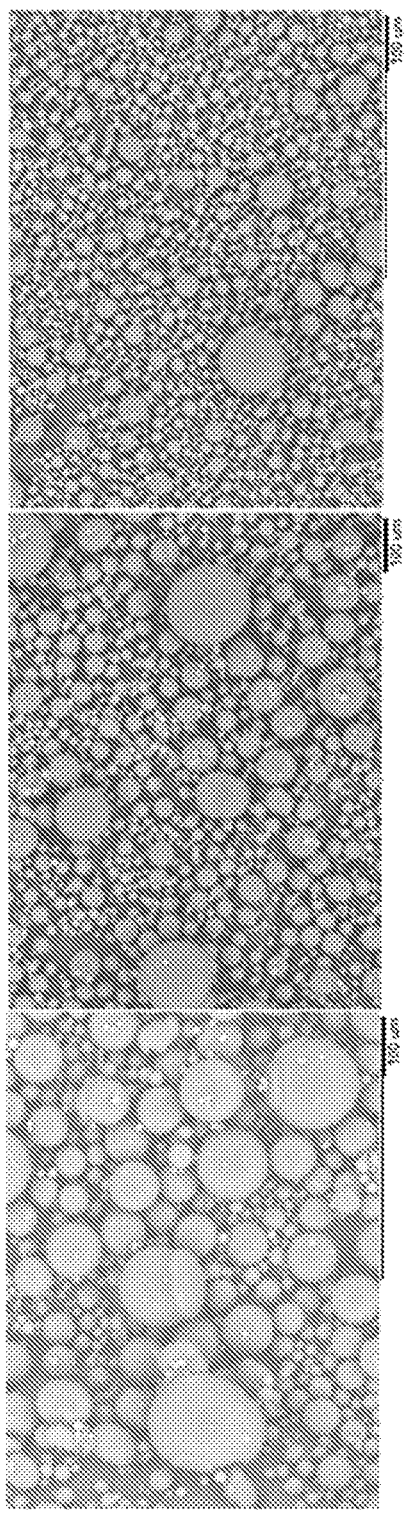
FIGS. 5A-5C show images of particles comprising bovine IgG and excipients that were obtained by inline homogenization using methods of the disclosure. Scale bar is 100 μm.

IgG microparticles were produced using inline homogenization 400 as shown in FIG. 4. Slurry vessel 420 was charged with second liquid. First liquid comprising IgG and excipients (e.g., aqueous feedstock 440) was pumped (430) and combined with second liquid in a tee immediately upstream of homogenizer 410 (Verso, Silverson, East Longmeadow, MA, USA). Following droplet formation and dehydration in the slurry vessel (420), the slurry was pumped (430) onto filter 460 to separate microparticles from waste 450, which were subsequently dried using air 470 at controlled flow rate and humidity. By varying the mixing speed, the particle size distribution (FIGS. 5A, 5B, 5C, with a scale bar at 100 um) was modulated accordingly: Verso speed (rpm) 2000:D50 (μm) 15.02 FIG. 5A; Verso speed (rpm) 4000:D50 (μm) 10.79 FIG. 5B; and Verso speed (rpm) 6000:D50 (μm) 6.84 FIG. 5C.

Example 9

Figure 6:
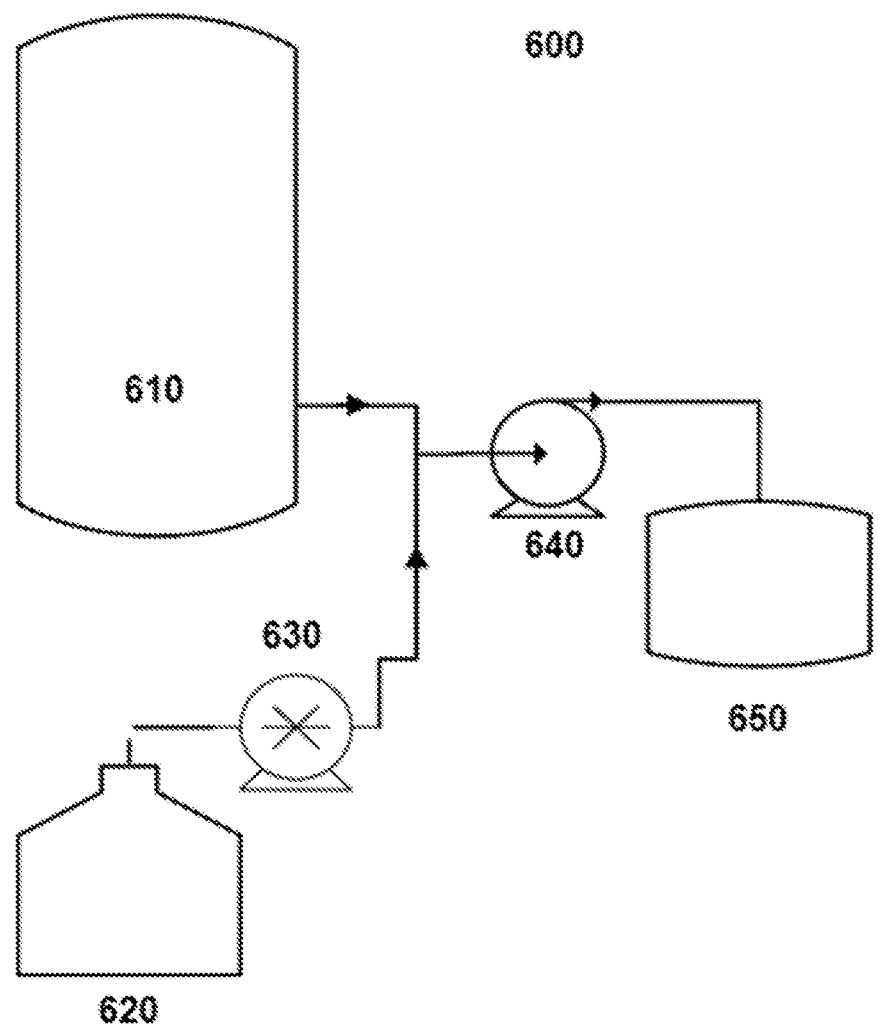
FIG. 6 shows a diagram of an exemplary inline homogenization system used to obtain particles comprising BSA and excipients through methods of the disclosure.
Figure 7:
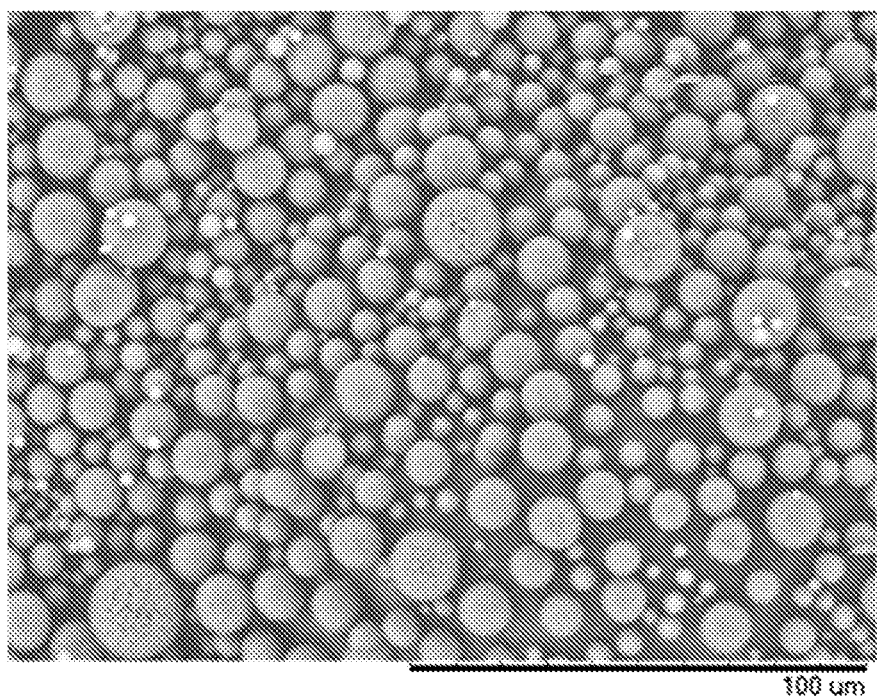
FIG. 7 shows an image of particles comprising BSA and excipients with a scale bar at 100 μm that were obtained by inline homogenization using methods of the disclosure.

BSA particles were produced using inline homogenization 600 as shown in FIG. 6. Solvent vessel 610 was charged with second liquid. First liquid comprising BSA 620 was pumped (630) and combined with second liquid in a tee immediately upstream of homogenizer 640 (Verso, Silverson, East Longmeadow, MA, USA) operating at 4000 rpm. Following droplet formation, dehydration occurred in receiving vessel 650. The resulting slurry was centrifuged at 500 RCF to separate the particles from the second liquid. The supernatant was decanted and the microparticles were then dried under vacuum at approximately 10 mbar for approximately 1 hour for additional drying. Dried microparticles had a mass median diameter of approximately 9 μm; size dispersity was quantified by a span of approximately 0.9. A SEM micrograph of the collected particles (with a scale bar at 100 um) is shown in FIG. 7.

Example 10

Figure 8:
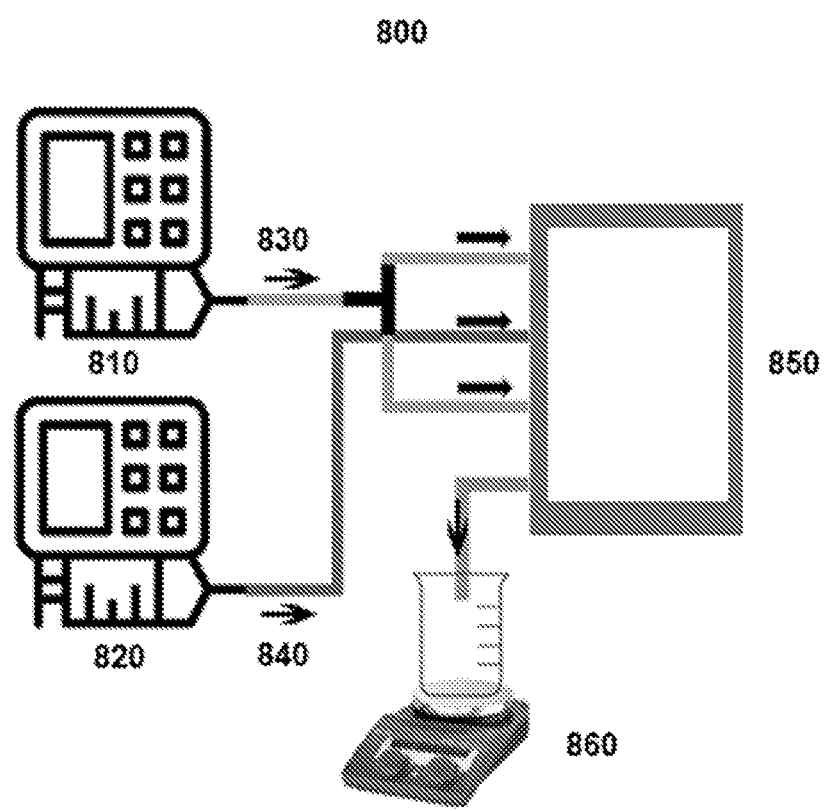
FIG. 8 shows a diagram of an exemplary microfluidic micromixing system used to obtain particles comprising mAb through methods of the disclosure.
Figure 9:
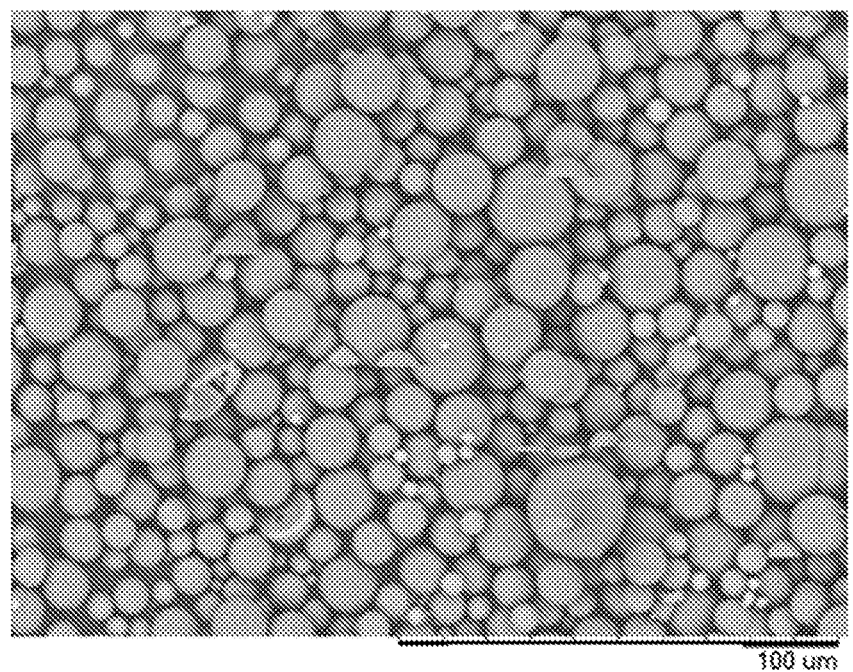
FIG. 9 shows an image of particles comprising Ab and excipients with a scale bar at 100 um that were obtained by microfluidic micromixing using methods of the disclosure.

Monoclonal antibody particles were produced using microfluidic micromixing 800 as shown in FIG. 8. First liquid comprising a monoclonal antibody and excipients 840 (DP) was combined (using first liquid pump 820 and second liquid pump 810) with second liquid 830 (CP) on microfluidic micromixer chip 850 to form droplets. Droplets were discharged into a stirred vessel for dehydration. The resulting microparticle slurry was centrifuged at 500 RCF and the supernatant decanted to recover microparticles 860 which were subsequently dried under vacuum at approximately 10 mbar for approximately 2 hours for additional removal of moisture and second liquid. The resulting microparticles had a mass median diameter of roughly 8 μm and a span of 0.8. Microparticles were imaged using SEM and displayed with a smooth spheroidal morphology with a scale bar at 100 um as shown in FIG. 9.

Example 11

Figure 10A:
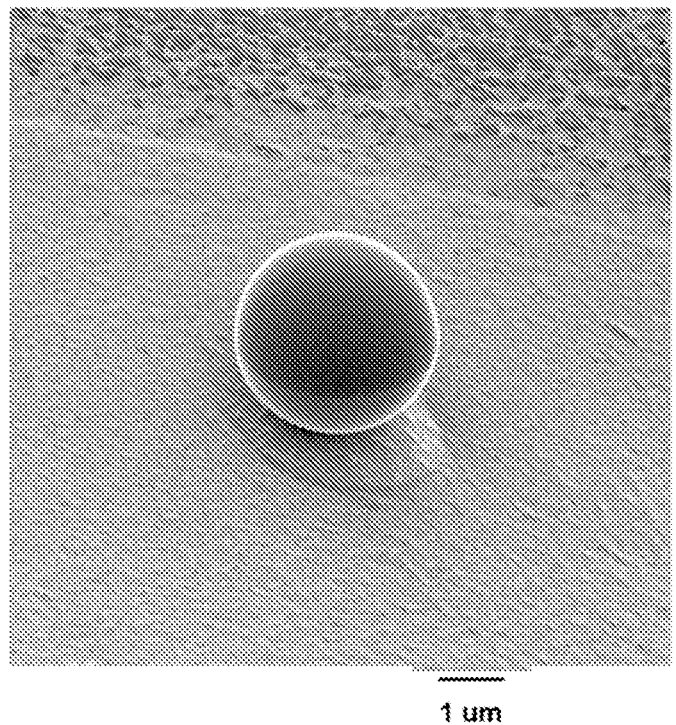
FIG. 10A shows an image of a human IgG particle surface formed through methods of the disclosure. Scale bar is 1 μm.
Figure 10B:
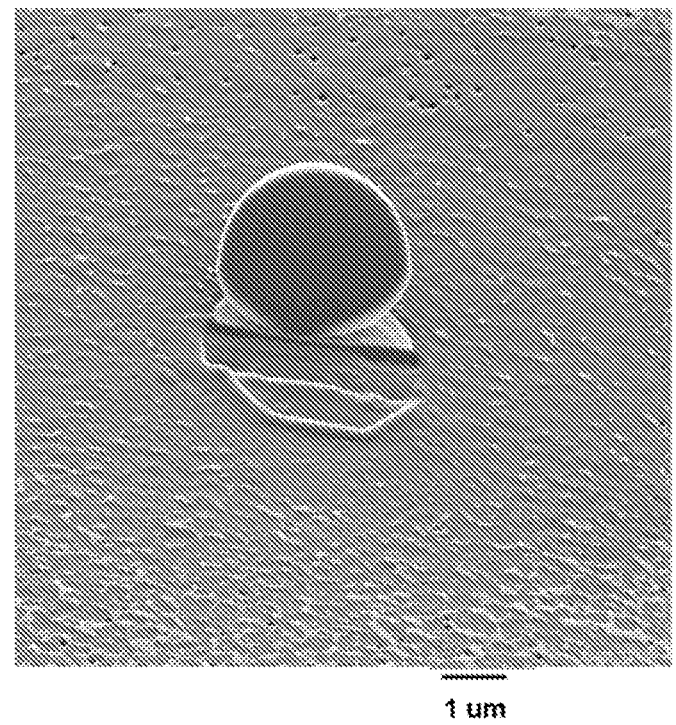
FIG. 10B shows an image of a human IgG particle sectioned to reveal the internal cross-section. Scale bar is 1 μm.

Internal Void Spaces:
Cross-sections of typical particles of the disclosure indicate an absence of pores (substantially free from any internal void spaces) and low particle porosity as shown by FIB-SEM with a scale bar at 1 um (FIGS. 10A-10B) or by gas pycnometry using helium at temperatures at about 22° C. to provide densities typically averaging about 1.3 g/cm$^3$ with standard deviations at about 0.0005 g/cm$^3$. The average circularity was calculated to be approximately 0.90 for the particle in FIG. 10A.

Example 12

Particle Quality Studies
Design:
The stability of the protein particles was assessed over the course of three months at 5, 25, and 40° C. to determine the stability of the particles in comparison to the protein liquid drug substance (LDS).
Buffer Exchange by Tangential Flow Filtration (TFF):
Protein feed solutions were prepared by diafiltration into the required buffer cocktails. A KrosFlow KR2i TFF system (Repligen) equipped with a hollow fiber filter module (MiniKros Sampler) was used to perform the feed preparation. A number of diafiltration volume exchanges were performed with the appropriate buffer for each formulation.
SEM Imaging:
The particles were imaged using a scanning electron microscope (Hitachi, TM-1000). A sample of the particles was mounted onto an adhesive stage for analysis. Images were captured at varying magnifications using an accelerating voltage of 15 kV.
Karl Fischer Coulometry:
Testing for moisture content was performed by Karl Fischer analysis using a MetroOhm (899 coulometer) equipped with an 860 KF Thermoprep oven. Particles were heated to 165° C. in an oven and the released water was determined coulometrically.
Particle Dissolution:
Water was added to dry particle samples to produce a final protein concentration. Samples are placed on a nutating mixer at 60 RPM for a period of time. The terminal dissolution concentration was recorded by removing an aliquot from the sample and measuring the absorbance at 280 nm (using the extinction coefficient E1%=1.69 L·g−1·cm−1).
Turbidity:
An aliquot of reconstituted particle solution was transferred to a 1-cm path length cuvette. The absorbance at 405 nm was recorded using a NanoDrop™ One UV-VIS spectrophotometer (Thermo Scientific).
Size-Exclusion Chromatography (SEC) Measurements:
Injections of redissolved particle samples were run at a flow rate of about 0.35 mL/min using a mobile phase comprised of 100 mM sodium phosphate monobasic and 200 mM L-arginine monohydrochloride, pH 6.5 for 10 minutes on a Tosoh TSKgel SuperSW mAb HTP (4.6 mm ID×15 cm L) column. Peaks were manually inspected to ensure accurate identification and analysis was performed by auto integration using parameters known in the art.
Strong Cation-Exchange Chromatography (SCEX):
Injections of redissolved particle samples were run at a flow rate of 0.4 mL/min using a gradient method that starts at 100% mobile phase pH gradient buffer A to 100% mobile phase pH gradient buffer B followed by washing and re-equilibration for a total run time of 40 minutes on a MAbPac™ SCX-10 RS Analysis Column, 2.1 mm ID×15 cm L, 5 μm column. Peaks were manually inspected to ensure accurate identification and analysis was performed by auto integration using parameters known in the art.

Hydrophobic Interaction Chromatography (HIC):

Injections of particle samples dissolved in diluent comprised of 750 mM Ammonium Sulfate, 50 mM Sodium Phosphate Monobasic Dihydrate, pH 6.0 (1 mg/mL) were run at a flow rate of 1 mL/min using a gradient method that starts at 50% mobile phase A comprised of 2M ammonium sulfate, 50 mM sodium phosphate monobasic dihydrate, pH 6.0 to 100% mobile phase B comprised of 50 mM sodium phosphate monobasic dihydrate, pH 6.0 followed by washing and re-equilibration using 50% mobile phase A for a total run time of 60 minutes on a MAbPac™ HIC-20 HPLC Column, 5 μm, 4.6 mm ID×25 cm L column. Peaks were manually inspected to ensure accurate identification and analysis was performed by auto integration using parameters known in the art.

Protein A Chromatography (ProA):

Injections of particle samples diluted in water to 1 mg/mL were run at a flow rate of 0.5 mL/min using a gradient method that starts at 100% mobile phase A comprised of 10 mM tris pH 7.0, 150 mM Sodium Chloride to 100% mobile phase B comprised of 20 mM sodium citrate pH 3.0, 150 mM sodium chloride followed by washing and re-equilibration using 100% mobile phase A for a total run time of 40 minutes on a POROS™ A column, 20 μm, 4.6 mm ID×5 cm L. Peaks were manually inspected to ensure accurate identification and analysis was performed by auto integration using parameters known in the art.

Particle Sizing (Laser Diffraction):

Particle size analysis was conducted via laser diffraction using a Horiba LA-960S. Dry particles were suspended in isopropyl alcohol at a concentration of approximately 0.1 mg/mL. The particle samples were sonicated within the particle measurement instrument to ensure homogeneity and then circulated and agitated by the Horiba particle size analyzer. Particle size analysis was conducted using a mobile phase of isopropyl alcohol and the volume average particle size distribution was calculated.

Microflow Imaging:

Flow imaging microscopy (FlowCam, Fluid Imaging Technologies) was performed to quantify subvisible particulates in protein LDS and the particle formulation. Particles were first redissolved using the particle dissolution method described above and diluted to 1 mg/mL with ultrapure water. For analysis, the aqueous sample was introduced at a flow rate of 0.15 mL/min. The resulting particle counts are recorded and reported per mg of protein.

Results:

The stability of dry particles were evaluated alongside the protein liquid drug substance (LDS). Stability was tracked at 5, 25, and 40° C. with data collected at 7, 14, 28, 60 and 90 days. Particle stability and protein stability were measured at each time and temperature. Analysis of the particles confirmed that protein quality remained constant as measured by the monomer profile (SEC), maintenance of charge variant profile (SCEX), isoforms/presumed oxidation (HIC, ProA), and colloidal stability (turbidity and subvisible particles). In each case, the protein feed solution and the LDS was measured against the particles. Particles stored as dry powder at 5, 25, and 40° C. showed a smooth, spherical morphology. Over the course of three months at these temperatures, no change in the particle morphology or the particle size distribution was observed. The moisture content of the particles remained constant for all storage temperatures and length of time. Analysis of protein aggregates were measured by SEC up to 90 days at 5, 25, and 40° C. The rate of aggregation for the particles demonstrated improved stability as compared to protein LDS. The charge variant profile of protein was measured by SCEX up to 90 days at 5, 25, and 40° C. No appreciable change was observed for particles, which demonstrated improved stability at 40° C. as compared to protein LDS. HIC and ProA were used to measure potential oxidation of protein. The degree of presumed global oxidation of protein was measured by HIC and ProA up to 90 days at 5, 25, and 40° C. No appreciable change was observed indicating that the particles demonstrated improved stability with respect to oxidative stress at 25 and 40° C. as compared to protein LDS at the same temperatures and times. To further probe the protein quality of the redissolved particles, visible and subvisible particulates were analyzed after storage at various temperatures. Upon dissolution, the protein solutions were essentially free of visible particulates and subvisible particulates after storage at 40° C. up to 90 days.

Example 13

Determination of Aggregation, Fragmentation and Change in Charge Variants

SEC:

Dry powder samples were dissolved to 5% (w/v) in ultrapure water and shaken at 60 RPM. After determining triplicate protein concentrations, the samples were diluted to 1 mg/mL with PBS and syringe filtered into HPLC vials. All samples were analyzed using an Agilent 1260 Infinity II Bio-inert LC System and TSKgel SuperSW HTP column (4 μm, 4.6 mmID×150 mmL) column equilibrated with 200 mM Arginine-HCl, 100 mM Sodium Phosphate pH 6.5. The autosampler and column compartment were maintained at 4° C. and 20° C., respectively, and UV absorbance was monitored at 280 nm. The run time was 10 minutes. The % areas of the integrated high molecular weight (aggregates), monomer and low molecular weight peaks were reported.

SCEX:

Dry powder samples were dissolved to 5% (w/v) in ultrapure water and shaken at 60 RPM. After determining triplicate protein concentrations, the samples were diluted with ultrapure water and syringe filtered into HPLC vials. All samples were analyzed using an Agilent 1260 Infinity II Bio-inert LC System and Thermo Scientific MAbPac™ SCX-10 RS column (5 μm, 2.1 mmID×150 mmL) equilibrated with 100% mobile phase A (Thermo Scientific 1X CX-1 pH Gradient Buffer A). The gradient is 0-20% mobile phase B (Thermo Scientific 1X CX-1 pH Gradient Buffer B). The autosampler and column compartment were maintained at 4° C. and 30° C., respectively, and UV absorbance was monitored at 280 nm. The % areas of the integrated acidic, neutral (main) and basic peaks were reported.

INCORPORATION BY REFERENCE

All publications and patents mentioned herein, are hereby incorporated by reference in their entirety as if each individual publication or patent was specifically and individually indicated to be incorporated by reference. In case of conflict, the present application, including any definitions herein, will control.

EQUIVALENTS

While specific aspects and embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:

1. A method of forming particles, the method comprising:

a) providing an aqueous first liquid comprising a therapeutic biologic;

b) contacting the aqueous first liquid comprising the therapeutic biologic with an organic second liquid by a continuous process, thereby forming a mixture comprising aqueous liquid droplets, wherein the aqueous liquid droplets comprise the therapeutic biologic;

c) dehydrating the aqueous liquid droplets in the mixture; and d) removing the aqueous first liquid and organic second liquid from the mixture, thereby forming particles comprising the therapeutic biologic, wherein the particles comprise less than about 10% internal void spaces and the circularity of the particles is from about 0.80 to about 1.00 after removing the aqueous first liquid and organic second liquid from the mixture, wherein the concentration of the therapeutic biologic in the aqueous first liquid is from about 10 mg/mL to about 500 mg/mL, wherein the aqueous first liquid has a viscosity of less than about 10 mPa-s, and wherein the continuous process of step b), comprises continuous membrane emulsification, continuous homogenization, continuous impinging jet mixing, continuous static mixing, or a combination thereof.

2. The method of claim 1, wherein the therapeutic biologic is an antibody, antibody fragment, bovine serum albumin (BSA), or human serum albumin (HSA).

3. The method of claim 1, wherein the aqueous first liquid is water, 0.9% saline, lactated Ringer's solution, a buffer, dextrose 5%, or a combination thereof.

4. The method of claim 1, wherein the aqueous first liquid further comprises a carbohydrate, a pH adjusting agent, a salt, a chelator, a mineral, a polymer, a protein stabilizer, an emulsifier, an antiseptic, an amino acid, an antioxidant, a protein, an organic solvent, a paraben, a bactericide, a fungicide, a vitamin, a preservative, a nutrient media, an oligopeptide, a biologic excipient, a chemical excipient, a surfactant, or a combination thereof.

5. The method of claim 1, wherein the organic second liquid is an organic solvent.

6. The method of claim 5, wherein the organic solvent is acetonitrile, chlorobenzene, chloroform, cyclohexane, cumene, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene, xylene, acetic acid, acetone, anisole, 1-butanol, 2-butanol, butylacetate, tert-butylmethyl ether, dimethyl sulfoxide, ethanol, ethylacetate, ethyl ether, ethyl formate, formic acid, heptane, isobutylacetate, isopropylacetate, methylacetate, 3-methyl-1-butanol, methylethyl ketone, 2-methyl-1-propanol, pentane, 1-pentanol, 1-propanol, 2-propanol, propylacetate, triethylamine, 1,1-diethoxypropane, 1,1-dimethoxymethane, 2,2-dimethoxypropane, isooctane, isopropyl ether, methylisopropyl ketone, methyltetrahydrofuran, petroleum ether, trichloroacetic acid, trifluoroacetic acid, decanol, 2-ethylhexylacetate, amylacetate, or a combination thereof.

7. The method of claim 1, wherein the continuous membrane emulsification is conducted by rotating membrane emulsification, cross-flow membrane emulsification, or a combination thereof.

8. The method of claim 1, wherein the continuous homogenization is conducted by shear homogenization, pressure homogenization, rotor-stator homogenization, microfluidization, or a combination thereof.

9. The method of claim 1, wherein the continuous static mixing comprises laminar flow, turbulent flow, transition flow, or a combination thereof.

10. The method of claim 1, wherein the aqueous liquid droplets in the mixture of step c) are dehydrated after contact with the organic second liquid of step b).

11. The method of claim 10, wherein the dehydration of the aqueous liquid droplets in the mixture of step c) occurs in a continuous drying tube, a continuous drying vessel, or a combination thereof.

12. The method of claim 11, wherein the continuous drying vessel comprises continuous mechanical stirring.

13. The method of claim 12, wherein the continuous mechanical stirring is conducted by a turbulent stirred vessel, a magnetic stirring device, or a mechanical stirring device.

14. The method of claim 1, wherein the aqueous first liquid and organic second liquid from the mixture of step d) are removed through centrifugation, sieving, filtration, solvent exchange, decanting, hydrocyclone separation, or a combination thereof.

15. The method of claim 1, further comprising washing the particles after step d) with a washing fluid.

16. The method of claim 15, wherein the washing fluid is an organic liquid, a supercritical fluid, a cryogenic liquid, or a combination thereof.

17. The method of claim 1, wherein the particles are further dried by lyophilization or vacuum desiccation.

18. The method of claim 1, wherein the particles are further dried by contacting the particles with a stream of gas.

* * * * *